US008232283B2

(12) United States Patent
Schoop et al.

(10) Patent No.: US 8,232,283 B2
(45) Date of Patent: Jul. 31, 2012

(54) RAF INHIBITORS

(75) Inventors: Andreas Schoop, Neuried (DE);
Alexander Backes, Kufstein (AT);
Joachim Vogt, Munich (DE); Lars Neumann, Kottgeisering (DE); Jan Eickhoff, Munich (DE); Stefan Hannus, Munich (DE); Kerrin Hansen, Gilching (DE); Peter Amon, Gilching (DE); Igor Ivanov, Markt Indersdorf (DE);
Matthias Borgmann, Stamberg (DE);
Chase Smith, Rutland, MA (US);
Arthur F. Kluge, Lincoln, MA (US);
Krishan Murthi, Andover, MA (US);
Rebecca Casaubon, Cambridge, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 13/105,957

(22) Filed: May 12, 2011

(65) Prior Publication Data

US 2011/0257207 A1    Oct. 20, 2011

Related U.S. Application Data

(63) Continuation of application No. 12/988,837, filed as application No. PCT/EP2009/002930 on Apr. 22, 2009.

(30) Foreign Application Priority Data

Apr. 22, 2008    (EP) .................................... 08103665

(51) Int. Cl.
C07D 471/04    (2006.01)
A61K 31/505    (2006.01)
A61P 35/00    (2006.01)

(52) U.S. Cl. ............. 514/264.1; 514/264.11; 514/235.2; 544/117; 544/279

(58) Field of Classification Search .................. 544/279, 544/117; 514/264.1, 264.11, 235.2
See application file for complete search history.

(56) References Cited

FOREIGN PATENT DOCUMENTS

| WO | WO 2005/011597 A | 2/2005 |
| WO | WO 2007/136465 A | 11/2007 |
| WO | WO 2008/034008 A | 3/2008 |
| WO | WO 2008/047307 A | 4/2008 |

*Primary Examiner* — Bruck Kifle
(74) *Attorney, Agent, or Firm* — Gearhart Law, LLC

(57) ABSTRACT

The present invention provides derivatives of pyrido[2,3-d]pyrimidin-7-one. These compounds are inhibitors or kinases such as Raf, including compounds that show anti-proliferative activity, including against tumor cells, and are useful in the treatment of diseases including cancer.

11 Claims, No Drawings

RAF INHIBITORS

CLAIM OF PRIORITY

This application is a continuation application of U.S. Ser. No. 12/988,837 filed on 10/21/2010 which is the national stage application pursuant to 35 U.S.C. 371 of International Patent Application No. PCT/EP2009/002930 filed Apr. 22, 2009 which claims the benefit of previously filed European Patent Application 08 103 665.9 filed Apr. 22, 2008 entitled "Improved RAF Inhibitors", all of which are incorporated herein by reference.

FIELD OF THE INVENTION

The present invention provides derivatives of pyrido[2,3-d]pyrimidin-7-one. These compounds are inhibitors of kinases such as Raf, including compounds that show anti-proliferative activity against cells, including against tumor cells, and are useful in the treatment of diseases including cancer.

BACKGROUND OF THE INVENTION

Kinases are important cellular enzymes that perform essential cellular functions such as regulating cell division and proliferation, and appear to play a decisive role in many disease states such as in disease states that are characterized by uncontrolled proliferation and differentiation of cells. These disease states encompass a variety of cell types and maladies such as cancer, atherosclerosis, and restenosis.

Drugs that target kinases, and especially drugs based on small-molecule chemical compounds that inhibit the activity of kinases, are important medicines that can significantly improve the health, lifespan or quality of life for people throughout the world, including patients suffering from highly debilitating diseases such as cancer. Indeed, the drug "imatinib" (GLEEVEC/GLIVEC; Novartis) is such a drug that inhibits a kinase and is used to successfully treat certain types of cancer including particular types of leukaemia (CML) and gastrointestinal cancer (GIST). Its improved efficacy compared to previous standard treatments for CML, and that it is generally very well tolerated, showing mild side-effects, has lead, among other reasons, for it to have made the cover of TIME magazine where it was described as a "bullet" to combat cancer.

Tyrosine kinases are essential for the propagation of growth factor signal transduction leading to cell cycle progression, cellular proliferation, differentiation, and migration. Tyrosine kinases include cell surface growth factor receptor tyrosine kinases (RTKs) such as FGFr and PDGFr as well as non-receptor tyrosine kinases including c-Src and Lck. Inhibition of these enzymes has been demonstrated to cause antitumor and antiangiogenesis activity (Hamby et al., Pharmacol. Ther, 1999; 82(2-3):169-193).

The molecular mechanisms and signaling pathways that regulate cell proliferation and survival are receiving considerable attention as potential targets for anticancer drug development. Recently, there has been a notable increase in efforts directed at targeting the MAPK pathway, which integrates proliferative signals that are initiated by a wide array of RTKs and G protein-coupled receptors.

The MAPK signal cascade includes a G protein, known as Ras, that works upstream of a core module consisting of three kinases: Raf, MEK1/2 and ERK1/2. In this signal cascade, Raf (a serine/threonine kinase) phosphorylates and thus activates MEK1/2, which in turn ultimately leads to the activation of ERK1/2. Understanding of Raf function in Ras signaling is complicated by the fact that in mammals Raf is encoded by a gene family consisting of three genes (A-raf, B-raf and C-raf (raf-1)) which encode highly conserved 68 to 74 kD proteins (Daum et al., Trends Biochem. Sci. 1994, 19: 474-480) sharing highly conserved amino-terminal regulatory regions and catalytic domains at the carboxyl terminus. Raf proteins are normally cytosolic but are recruited to the plasma membrane by the small G-protein Ras, with this being an essential step for Raf activation by growth factors, cytokines, and hormones. Raf activation at the membrane occurs through a highly complex process involving conformation changes, binding to other proteins, binding to lipids, and phosphorylation and dephosphorylation of some residues.

Raf kinases, and particularly B-Raf, have long been considered attractive targets for drug discovery and therapeutic intervention due to their importance as potential checkpoints for cancer-related signal transduction (Tuveson et al., Cancer Cell, 2003, 4: 95-98; Strumberg and Seeber, Onkologie, 2005, 28: 101-107; Beeram et al., J. Clin. Oncol. 2005, 23: 6771-6790).

The importance of the MAPK signalling cascade for the proliferation and survival of tumor cells has recently increased following the discovery of a number of activating mutations of B-Raf in human tumors. Activating Raf mutations have been identified in melanoma, thyroid, colon, and other cancers (Davies et al., Nature, 2002, 417: 949-954; Cohen et al., J. Natl. Cancer Inst., 2003, 95: 625-627; Mercer and Pritchard, Biochim Biophys Acta, 2003, 1653: 25-40; Oliveira et al., Oncogene, 2003, 22: 9192-9196; Pollock et al., Nat. Genet. 2003, 33: 19-20; Domingo et al., Genes Chromosomes Cancer 2004, 39: 138-142; Shih and Kurman, Am. J. Pathol., 2004, 164: 1511-1518). Therefore, in addition to a role in controlling tumors with Ras mutations or activated growth factor receptors, inhibitors of Raf kinases harbor therapeutic potential for tumors carrying a B-Raf oncogene (Sharma et al., Cancer Res. 2005, 65: 2412-2421).

A variety of agents have been discovered to interfere with Raf kinases, including antisense oligonucleotides and small molecules. These inhibitors prevent the expression of Raf protein, block Ras/Raf interaction, or obstruct its kinase activity. Down-regulation of B-Raf activity by siRNA led to decreased tumorigenic potential of 1205 Lu cells (Sharma et al., Cancer Research, 2005, 65: 2412-2421), and by the kinase inhibitor BAY43-9006 (Sorafenib) led to inhibition of the growth of melanoma cells (Panka et al., Cancer Research., 2006, 66: 1611-9). Raf inhibitors that are currently undergoing clinical evaluation show promising signs of anti-cancer efficacy with a very tolerable safety profile. Most advanced is the Raf inhibitor Sorafenib (Nexavar®), which has been in clinical testing for the treatment of metastatic renal cell carcinoma (Ratain et al., Proc. Am. Soc. Clin. Oncol. (ASCO Meeting Abstract), 2004, 23: Abstract 4501; Motzer et al., J. Clin. Oncol. 2006, 24: 16-24) and which was approved in 2007 by the EMEA for the treatment of patients with advanced renal cell carcinoma. (RCC), or kidney cancer, who have failed prior interferon alfa or interleukin-2 based therapy or are considered unsuitable for such therapy, and by the FDA for use in patients with a form of liver cancer known as hepatocellular carcinoma, when the cancer is inoperable.

The family of mitogen-activated protein (MAP) kinases are proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38a, p39ss, p38 or p38δ).

The p38 kinases are responsible for phosphorylating and activating transcription factors as well as other kinases, and are activated by physical and chemical stress, proinflammatory cytokines, and bacterial lipopolysaccharides.

More importantly, the products of the p38 phosphorylation have been shown to mediate the production of inflammatory cytokines, including TNF, IL-1, and cyclooxygenase-2. These cytokines have been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein Barr virus, human herpes virus-6 (HHV-6), human herpes virus-7(HHV-7), human herpes virus-8 (HHV-8), pseudorabies and rhiriotracheitis, among others.

Similarly, IL-1 is produced by activated monocytes and macrophages, and plays a role in many pathophysiological responses including rheumatoid arthritis, fever and reduction of bone resorption.

Additionally, p38 has been implicated in stroke, Alzheimer's disease, osteoarthritis, lung injury, septic shock, angiogenesis, dermatitis, psoriasis and atopic dermatitis, see, e.g., J. Exp. Opin. Ther. Patents, (2000) 10(1).

The inhibition of the above-mentioned cytokines by inhibition of the p38 kinase can be of benefit in controlling, reducing and/or alleviating one or more of these disease states.

Despite the progress that has been made, the search continues for low molecular weight kinase inhibitor compounds, especially compounds that inhibit Raf kinases, that are useful for treating a wide variety of diseases, including cancer, tumors and other proliferative disorders or diseases including restenosis, angiogenesis, diabetic retinopathy, psoriasis, surgical adhesions, macular degeneration, and atherosclerosis, or other disorders or diseases mentioned above. Thus, a strong need exists to provide compositions, pharmaceuticals and/or medicaments with kinase inhibitory activity, particularly inhibitory activity against one or more Raf kinases, or with anti-proliferative activity against cells such as tumour cells. Such compositions, pharmaceuticals and/or medicaments may possess not only such activity, but may also exert tolerable, acceptable or diminished side effects in comparison to other anti-proliferative agents. Furthermore, the spectrum of tumors or other diseases responsive to treatment with such compositions, pharmaceuticals and/or medicaments may be broad. The active ingredients of such compositions, pharmaceuticals and/or medicaments may be suitable in the mentioned indication as single agent, and/or in combination therapy, be it in connection with other therapeutic agents, with radiation, with operative/surgical procedures, heat treatment or any other treatment known in the mentioned indications.

It is known that specific classes of pyrido[2,3-d]pyrimidines, substituted in a specific manner, have pharmacologically useful properties. In particular, specific derivatives of pyrido[2,3-d]pyrimidin-7-one are known to possess anti-proliferative activity. These compounds however are structurally dissimilar from the compounds of the present invention.

WO 96/34867 discloses 2-substituted and 2,8-disubstituted 6-aryl-pyrido[2,3-d]pyrimidin -7-ones and 7-imino derivatives thereof, that are shown to inhibit tyrosine kinases and to have certain activity in tumor models (see also U.S. Pat. No. 5,620,981 and U.S. Pat. No. 5,733,914). WO 01/55147 discloses 5,6-disubstituted 2,7-diamino-pyrido[2,3-d]pyrimidines having similar activities. WO 01/70741 discloses substituted 2-amino-5-(alkyl,aryl)-pyrido[2,3-d]pyrimidin-7-ones, that are shown to have Cdk inhibitor activity. WO 02/18380 discloses 8-unsubstituted and 8-substituted 2-amino-6-aryl-pyrido[2,3-d]pyrimidin-7-ones, that are shown to inhibit protein kinases, including p38. WO 02/18380 and WO 03/088972 disclose 2,4,8-trisubstituted pyrido[2,3-d]pyrimidin-7-ones, that are shown to inhibit kinases and are thus are able to inhibit the production of various cytokines. WO 02/064594 discloses 8-unsubstituted and 8-substituted 2-amino-6-(amino,oxy)-pyrido [2,3-d]pyrimidin-7-ones and 7-imino derivatives thereof, that are shown to inhibit protein kinases, including p38. WO 03/062236 discloses 2-(pyrid-2-yl)amino-pyrido[2,3-d]pyrimidin-7-ones (optionally substituted at positions 5, 6 and/or 8), that are shown to be potent inhibitors of Cdk 4. WO 03/066630 discloses 6-(monocyclyl)-pyrido[2,3-d]pyrimidin-7-ones (optionally substituted at positions 2, 4 and/or 5), that are shown to be inhibitors of Cdks, and that showed activity in an ischemic stroke model. WO 2004/063195 discloses derivatives of 2-amino-8-methyl-6-phenyl-pyrido[2, 3-d]pyrimidin-7-one that are shown to inhibit Bcr-Abl kinase.

In particular, PCT publication WO 03/062236 discloses 2-(pyrid-2-yl)amino-pyrido[2,3-d]pyrimidin-7-ones and 2-(pyrid-2-yl)amino-dihydropyrido[2,3-d]pyrimidin-7-ones (optionally substituted at positions 5, 6 and/or 8), as potent and selective inhibitors of Cdk 4 (and Cdk 6), and compares certain such compounds to their C2-phenylamino analogues, as disclosed in WO 98/33798 and WO 01/70741. The generic Markush structure disclosed and claimed in WO 03/062236 includes, amongst other suggested substituents at the nitrogen in position 8, a generically described substituent being "$C_1$ to $C_8$ alkoxy". WO 07/136,465 discloses certain 6-(alkoxy-aminocarbonylphenyl)-pyrido[2,3-d]pyrimidin-7-ones for treating diseases and disorders associated with abnormal kinase activities. The generic Markush structure disclosed and claimed in WO 07/136,465 includes, amongst other suggested substituents at the nitrogen in position 8, a generically described substituent —O—$R^7$, with —$R^7$ including "$C_{1-8}$ alkyl".

SUMMARY OF THE INVENTION

We have invented a class of 8-substituted pyrido[2,3-d] pyrimidin-7-ones that includes compounds that exhibit surprising properties, including activity as inhibitors of a number of protein kinases such as C- and B-Raf, or p38, and anti-proliferative activity against cells such as tumour cells. Such derivatives of pyrido[2,3-d]pyrimidin-7-ones provide an opportunity to develop new and effective therapies for diseases associated with kinase de-regulation or cellular proliferation, such as cancer or inflammatory disorders.

Compounds of the present invention are specific derivatives of pyrido[2,3-d]pyrimidin-7-one, as discussed in greater detail below. In analogy to certain pyrido[2,3-d]pyrimidin-7-ones previously described, the compounds of the present invention are suitable for further pre-clinical or clinical research and development towards the treatment of a variety of disorders and diseases including cancer, proliferative, degenerative, inflammatory and other disorders and diseases. The present invention provides effective therapies and therapeutics for particularly debilitating diseases such as cancer and other diseases and disorders including those listed herein.

One aspect of the invention relates to 8-oxy-pyrido[2,3-d]pyrimidin-7-ones having a structure represented by formula (I) presented below, or tautomeric or stereoisomeric forms thereof, which are useful as kinase inhibitors and thus useful for treating disorders or diseases mentioned herein, including proliferative disorders or diseases such as cancer, and inflammatory disorders or diseases.

In another aspect, the invention relates to pharmaceutical compositions, including a pharmaceutically acceptable diluent, excipient or carrier and an amount, such as a therapeutically effective amount, of such kinase inhibitor, e.g., which is expected to ameliorate the effects of disorders or diseases mentioned herein, including proliferative disorders or diseases such as cancer, and inflammatory disorders or diseases.

Another aspect of the invention relates to a pharmaceutical package, including such pharmaceutical composition, and instructions which indicate that said pharmaceutical composition may be used for the treatment of a patient suffering from a disorder or disease mentioned herein, including proliferative disorders or diseases such as cancer, and inflammatory disorders or diseases.

In another aspect, the invention relates to methods that involve administering to or contacting a subject, a cell, a tissue, an organ or an organism with a therapeutically effective amount of a compound or pharmaceutical composition disclosed herein. These methods include, but are not limited to, prophylaxis and/or treatment of a disorder or disease mentioned herein, including proliferative disorders or diseases such as cancer, and inflammatory disorders or diseases.

In another aspect, the invention relates to uses of the compounds of the present invention for the preparation of a medicament for the treatment of a disorder or disease mentioned herein, including proliferative disorders or diseases such as cancer.

In another aspect, the invention relates to uses of the compounds of the present invention for the preparation of a medicament for the treatment of an inflammatory disorder or disease.

Another aspect of the invention relates to methods of synthesizing the compounds of the present invention, and to intermediates for such compounds.

Accordingly, the present invention provides compounds having a structure represented by the general formula (I)

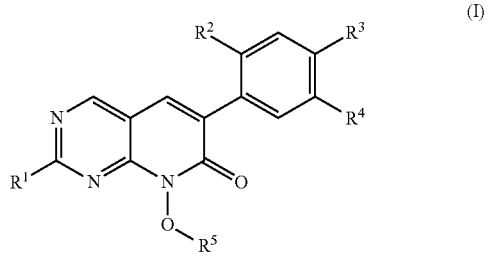

(I)

or any tautomeric form thereof, wherein $R^1$ is selected from hydrogen, —$NH_2$, and substituted or unsubstituted: —NH—$C_{1-6}$-alkyl, —NH-cycloalkyl, —NH-heterocycloalkyl, —NH-aryl, —NH-heteroaryl, —NH—$C_{1-6}$-alkylene-$OR^7$, and —NH—$C_{1-6}$-alkylene-$NR^7{}_2$;

$R^2$ is selected from hydrogen, -halogen, -methyl, —$CH_2F$, —$CHF_2$, —$CF_3$, —O-methyl, —O—$CH_2F$, —O—$CHF_2$, and —O—$CF_3$;

one of $R^3$ and $R^4$ is hydrogen, and the other is —NH—C(=O)—$(NH)_x$—$(CH_2)_y$—$R^6$, wherein x and y are independently selected from 0 and 1;

$R^5$ is selected from hydrogen, and substituted or unsubstituted: -alkyl, -alkenyl, -alkynyl, -cycloalkyl, -cycloalkenyl, —(C-linked heterocycloalkyl), —(C-linked heterocycloalkenyl), -aryl, and -heteroaryl;

$R^6$ is selected from substituted or unsubstituted aryl, and substituted or unsubstituted heteroaryl;

$R^7$ is independently selected from hydrogen and —$C_{1-6}$-alkyl;

or any pharmaceutically acceptable salt or N-oxide thereof;

provided, however, that (i) R1 is not substituted or unsubstituted —NH-phenyl; and that (ii) compound (A) is excluded:

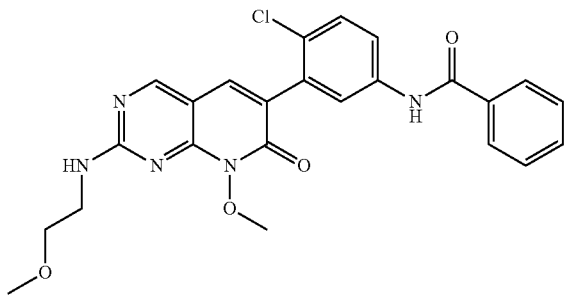

(A)

Other features and advantages of the invention will be apparent from the following detailed description and from the claims.

DETAILED DESCRIPTION OF THE INVENTION

Definitions

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, s-pentyl, and n-hexyl.

The term "alkenyl" refers to groups having 2 to about 20 carbon atoms, wherein at least one of the carbon-carbon bonds is a double bond, while other bonds may be single bonds or further double bonds. The term "alkynyl" herein refers to groups having 2 to about 20 carbon atoms, wherein at least one of the carbon-carbon bonds is a triple bond, while other bonds may be single, double or further triple bonds. Examples of alkenyl groups include ethenyl, 1-propenyl, 2-propenyl, 1-butenyl, 2-butenyl, 3-butenyl, 2-methyl-1-propenyl, 2-methyl-2-propenyl, and the like. Examples of alkynyl groups include ethynyl, 1-propynyl, 2-propynyl, and so forth.

As used herein, "cycloalkyl" is intended to refer to a ring being part of any stable monocyclic or polycyclic system, where such ring has between 3 and about 12 carbon atoms, but no heteroatom, and where such ring is fully saturated, and the term "cycloalkenyl" is intended to refer to a ring being part of any stable monocyclic or polycyclic system, where such ring has between 3 and about 12 carbon atoms, but no heteroatom, and where such ring is at least partially unsaturated (but excluding any aryl ring). Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl. For the sake of clarity, if a substituent is a polycyclic ring system as described above wherein one ring is a least partially unsaturated, then such substituent will be referred to as "cycloalkenyl", if substitution occurs via the at least partially unsaturated ring, and as "cycloalkyl", if substitution occurs via a fully saturated ring.

The term "$C_{x-y}$—", when used in combination with a group as defined herein, is intended to indicate the range of carbon atoms being present in the respective group, excluding substituents.

For example, the term "$C_{1-6}$-alkyl" refers to the alkyl groups having between one carbon atom (i.e. a methyl group) and six carbon atoms (e.g. n-hexyl); the term "$C_{3-6}$-cycloalkyl" refers to cycloalkyl groups having between three carbon atom (i.e. a cyclopropyl group) and six carbon atoms (i.e. cyclohexyl).

As used herein, the terms "heterocycloalkyl" and "heterocycloalkenyl", are intended to refer to a ring being part of any stable monocyclic or polycyclic ring system, where such ring has between 4 and about 12 atoms, and where such ring consists of carbon atoms and at least one heteroatom, particularly at least one heteroatom independently selected from the group consisting of N, O and S, with heterocycloalkyl referring to such a ring that is fully saturated, and heterocycloalkenyl referring to a ring that is at least partially unsaturated (but excluding any aryl or heteroaryl ring). For the sake of clarity, if a substituent is a polycyclic ring system wherein one ring contains at least one heteroatom as described herein, then such substituent will be referred to as "heterocycloalkyl/-alkenyl", if substitution occurs via the ring containing the heteroatom(s). Heterocycloalkyl and heterocycloalkenyl groups may be linked to other groups via a carbon ring atom ("C-linked heterocycloalkyl" and "C-linked heterocycloalkenyl", respectively), or via a nitrogen ring atom ("N-linked heterocycloalkyl" and "N-linked heterocycloalkenyl", respectively). Heteroatoms such as nitrogen and sulfur may optionally be oxidized to form N-oxides or sulfoxides and sulfones, respectively. In certain embodiments, a nitrogen in the heterocycle may be quaternized. In certain embodiments, where the total number of S and O atoms in the heterocycle exceeds 1, these heteroatoms are not adjacent to one another. In particular embodiments, the total number of S atoms in the heterocycle is not more than 1.

Examples of heterocycloalkyls include, but are not limited to, pyrrolidinyl, tetrahydrofuranyl, morpholinyl, thiomorpholinyl, piperazinyl, piperidinyl, and decahydroquinolinyl (when linked via the piperidinyl moiety). Examples of heterocycloalkenyls include, but are not limited to, pyrrolinyl, and indolenyl (when linked via the 5-membered ring). Also included are fused ring systems sand spiro compounds containing, for example, any of the above heterocycles, in each case when linked a heteratom-containing ring.

The term "aryl" is intended to mean a ring or ring system being part of any stable monocyclic or polycyclic system, where such ring or ring system has between 3 and about 20 carbon atoms, but has no heteroatom, and where the ring or ring system consists of an aromatic moiety as defined by the "(4n+2) π electron rule". For the sake of clarity, if a substituent is a polycyclic system wherein one ring or ring system comprised in said polycyclic system consists of an aromatic moiety as defined herein, then such substituent will be referred to as "aryl", if substitution occurs via said aromatic moiety. This includes, but is not limited to, phenyl and fused benzene ring systems, for example, naphthalene, anthracene, or phenanthrene ring systems, or, for example, a benzene ring fused to one or more cycloalkyl moieties to form, for example, indanyl, fluorenyl or tetrahydronaphthyl(tetralin), or fused to one or more heterocycloalklyl rings, e.g. as in indolenyl, provided, however, that in each such case, such fused system is linked as a substituent via the aromatic moiety.

As used herein, the term "heteroaryl" refers to a ring or ring system being part of any stable mono- or polycyclic system, where such ring or ring system has between 3 and about 20 atoms, which ring or ring system consists of an aromatic moiety as defined by the "(4n+2) π electron rule" and which contains carbon atoms and one or more nitrogen, sulfur, and/or oxygen heteroatoms. For the sake of clarity, if a substituent is a polycyclic system wherein one ring or ring system comprised in said polycyclic system consists of an aromatic moiety containing a heteroatom as defined herein, then such substituent will be referred to as "heteroaryl", if substitution occurs via the aromatic moiety containing the heteroatom. In certain embodiments, the total number of N, S and O atoms in the heteroaryl is between 1 and about 4. In certain embodiments, the total number of S and O atoms in the aromatic heteroaryl is not more than 1. In certain embodiments, a nitrogen in the heterocycle may be quaternized or oxidized to an N-oxide. Examples of heteroaryls include, but are not limited to, pyrrolyl, pyrazolyl, imidazolyl indolyl, benzimidazolyl, furanyl, benzofuranyl, thiophenyl, benzothiophenyl, pyridinyl, pyrimidinyl, pyrazinyl, triazinyl, quinolinyl, quinazolinyl Also included in the term heteroaryl are fused heteroaryls containing, for example, the above heteroaryls fused to cycloalkyls or heterocycloalkyls (provided, in each case, that such fused system is linked as a substituent via the aromatic moiety containing at least one heteroatom).

Wherever indicated herein, alkyl, alkenyl, alkynyl, cycloalkyl, cycloalkenyl, heterocycloalkyl, heterocycloalkenyl, aryl and heteroaryl groups as well as and any other substructure comprising at least one hydrogen in the substructure may be substituted by one or more substituents.

"Substituted" is intended to indicate that one or more hydrogens on the atom or group indicated in the expression using "substituted" is replaced with a selection from the indicated group(s), provided that the indicated atom's normal valency, or that of the appropriate atom of the group that is substituted, is not exceeded, and that the substitution results in a stable compound. The terms "substituted or unsubstituted" or "optionally substituted" are intended to mean that a given compound, or substructure of a compound, is either unsubstituted, or substituted, as defined herein, with one or more substituents, as indicated or as defined below.

In a substituted moiety, unless a specific list of substituents is explicitly provided, at least one hydrogen atom of the moiety "M" to be substituted is replaced by a substituent —[($R^{Sm}$)$_n$], wherein m is an integer running from 1 to n, wherein n is any value from 1 to about 15, wherein each $R^{Sm}$ is independently selected from the following lists (A) and (B):

(A): alkyl, alkenyl, alkynyl, cycloalkyl, cycloalkenyl, C-linked heterocycloalkyl, C-linked heterocycloalkenyl, aryl, C-linked heteroaryl, —O—$R^a$, —O—$N(R^a)_2$, —S—$R^a$, —S—$N(R^a)_2$, N-linked heterocycloalkyl, N-linked heteroaryl, —$N(R^a)$—$R^a$, —$N(R^a)$—$OR^a$, —$N(R^a)$—$SR^a$, —$N(R^a)$—$N(R^a)_2$, —F, —Cl, —Br, —I;

(B): —C(=O)—$R^a$, —C(=S)—$R^a$, —C(=$NR^a$)—$R^a$, —C(=N—$OR^a$)—$R^a$, —C(=N—$N(R^a)_2$)—$R^a$, —C(=O)—$OR^a$, —C(=S)—$OR^a$, —C(=O)—$N(R^a)_2$, —C(=S)—$N(R^a)_2$, —C(=$NR^a$)—$N(R^a)_2$, —C(=N—$OR^a$)—$N(R^a)_2$, —C(=N—$N(R^a)_2$)—$N(R^a)_2$, —C(=O)—$N(R^a)$—$N(R^a)_2$, —C(=S)—$N(R^a)$—$N(R^a)_2$, —C(=$NR^a$)—$N(R^a)$—$N(R^a)_2$, —CN, —O—N=$C(R^a)_2$, —O—C(=O)—$R^a$, —O—C(=S)—$R^a$, —O—C(=$NR^a$)—$R^a$, —O—C(=N—$OR^a$)—$R^a$, —O—C(=N—$N(R^a)_2$)—$R^a$, —O—C(=$NR^a$)—$OR^a$, —O—C(=$NR^a$)—$SR^a$, —O—C(=$NR^a$)—$N(R^a)_2$, —S—$N(R^a)$—$N(R^a)_2$, —S—N=$C(R^a)_2$, —S—N=$NR^a$, —SO—$R^a$, —SO—$OR^a$, —SO—$SR^a$, —SO—$N(R^a)_2$, —SO—$N(R^a)$—$N(R^a)_2$, —$SO_2$—$R^a$, —$SO_2$—$OR^a$, —$SO_2$—$SR^a$, —$SO_2$—$N(R^a)_2$, —$SO_2$—$N(R^a)$—$N(R^a)_2$, —$N(R^a)$—N=$C(R^a)_2$, —$N(R^a)$—C(=O)—$R^a$, —$N(R^a)$—C(=S)—$R^a$, —$N(R^a)$—C(=$NR^a$)—$R^a$, —$N(R^a)$—C(=N—$OR^a$)—$R^a$, —$N(R^a)$—C(=N—$N(R^a)_2$)—$R^a$, —$N(R^a)$—C(=O)—$OR^a$, —$N(R^a)$—C(=S)—$OR^a$, —$N(R^a)$—C(=$NR^a$)—$OR^a$, —$N(R^a)$—C(=N—$OR^a$)—$OR^a$, —$N(R^a)$—C(=N—$N(R^a)_2$)—$OR^a$, —$N(R^a)$—C(=O)—$N(R^a)_2$, —$N(R^a)$—C(=S)—$N(R^a)_2$, —$N(R^a)$—C(=$NR^a$)—$N(R^a)_2$, —$N(R^a)$—C(=N—$OR^a$)—$N(R^a)_2$, —$N(R^a)$—C(=N—$N(R^a)_2$)—$N(R^a)_2$, —$N(R^a)$—C(=O)—$N(R^a)$—$N(R^a)_2$, —$N(R^a)$—C(=S)—$N(R^a)$—$N(R^a)_2$, —$N(R^a)$—C(=$NR^a$)—$N(R^a)$—$N(R^a)_2$, —$N(R^a)$—C(=N—$OR^a$)—$N(R^a)$—$N(R^a)_2$, —$N(R^a)$—C(=N—$N(R^a)_2$)—$N(R^a)$—$N(R^a)_2$, —$N(R^a)$—$N(R^a)$—C(=O)—$R^a$, —$N(R^a)$—$N(R^a)$—C(=S)—$R^a$, —$N(R^a)$—$N(R^a)$—C(=$NR^a$)—$R^a$, —$N(R^a)$—$N(R^a)$—C(=N—$OR^a$)—$R^a$, —$N(R^a)$—$N(R^a)$—C(=N—$N(R^a)_2$)—$R^a$, —$N(R^a)$—$N(R^a)$—C(=O)—$OR^a$, —$N(R^a)$—$N(R^a)$—C(=S)—$OR^a$, —$N(R^a)$—$N(R^a)$—C(=$NR^a$)—$OR^a$, —$N(R^a)$—$N(R^a)$—C(=N—$OR^a$)—$OR^a$, —$N(R^a)$—$N(R^a)$—C(=N—$N(R^a)_2$)—$OR^a$, —$N(R^a)$—$N(R^a)$—C(=O)—$N(R^a)_2$, —$N(R^a)$—$N(R^a)$—C(=S)—$N(R^a)_2$, —$N(R^a)$—$N(R^a)$—C(=$NR^a$)—$N(R^a)_2$, —$N(R^a)$—$N(R^a)$—C(=N—$OR^a$)—$N(R^a)_2$, —$N(R^a)$—$N(R^a)$—C(=N—$N(R^a)_2$)—$N(R^a)_2$, —$N(R^a)$—$N(R^a)$—C(=O)—$N(R^a)$—$N(R^a)_2$, —$N(R^a)$—$N(R^a)$—C(=S)—$N(R^a)$—$N(R^a)_2$, —$N(R^a)$—$N(R^a)$—C(=$NR^a$)—$N(R^a)$—$N(R^a)_2$, —$N(R^a)$—$N(R^a)$—C(=N—$OR^a$)—$N(R^a)$—$N(R^a)_2$, —$N(R^a)$—$N(R^a)$—C(=N—$N(R^a)_2$)—$N(R^a)$—$N(R^a)_2$, —$N(R^a)$—$N(R^a)$—C(=$NR^a$)—N=$C(R^a)_2$, —$N(R^a)$—N(R^a)—C(=N—$OR^a$)—N=$C(R^a)_2$, —$N(R^a)$—$N(R^a)$—C(=N—$N(R^a)_2$)—N=$C(R^a)_2$, —$N(R^a)$—SO—$R^a$, —$N(R^a)$—SO—$OR^a$, —$N(R^a)$—SO—$N(R^a)_2$, —$N(R^a)$—SO—$NR^a$—$N(R^a)_2$, —$N(R^a)$—$SO_2$—$R^a$, —$N(R^a)$—$SO_2$—$OR^a$, —$N(R^a)$—$SO_2$—$N(R^a)_2$, —$N(R^a)$—$SO_2$—$NR^a$—$N(R^a)_2$, —$NO_2$, —$N_3$, —F, —Br, —I;

wherein each $R^a$ is independently selected from —H and $R^b$, with $R^b$ being independently selected from alkyl, alkenyl, alkynyl, cycloalkyl, cycloalkenyl, C-linked heterocycloalkyl, C-linked heterocycloalkenyl, aryl, and C-linked heteroaryl, and wherein alternatively two substituents $R^b$, when attached to the same nitrogen atom, can form together with the nitrogen atom they are attached to a heterocycloalkyl, heterocycloalkenyl, or heteroaryl group, and wherein $R^{S1}$ is attached to such moiety M, and wherein any additional $R^{Sx}$, if present, is substituting a hydrogen atom in a residue $R^b$ of a group $R^{Sy}$, with x>y.

A methylene group present in a ring of a cycloalkyl, cycloalkenyl, heterocycloalkyl, and heterocycloalkenyl moiety may as well be substituted by a substituent $R^S$ taken from the following list (C):

(C): =O, =S, =$NR^a$, =N—$OR^a$, and =N—$N(R^a)_2$, wherein for each such substituent both hydrogens on the methylene group of the unsubstituted moiety are being replaced.

Nitrogen-containing substructures, such as amines or nitrogen-containing heterocycles, may be substituted as well by formation of quaternary amines or N-oxides, wherein $R^S$ is alkyl or —O.

For example, a substituent —$CH_2$—O—$CH_2$—$CH_2$—F can be described as —$[(R^{Sm})_3]$ with $R^{S3}$ being —F that substitutes a hydrogen atom in $R^{S2}$ being —O—$C_2$-alkyl, where such $R^{S2}$ substitutes a hydrogen atom in $R^{S1}$ being $C_1$-alkyl. In this example, the individual elements $R^{Sm}$ in —$[(R^{Sm})_3]$ are arranged in a "linear" fashion, since every $R^{Sx}$ is linked to a $R^{Sy}$ with x=y+1 (i.e. $R^{S3}$ is linked to $R^{S2}$, and so on).

As a second example, the substituent —$CH_2$—O—$CH_2$—$CF_3$ can be described as —$[(R^{Sm})_5]$ with each of $R^{S3}$, $R^{S4}$, and $R^{S5}$ being a —F atom that substitutes a hydrogen atom in $R^{S2}$ being —O—$C_2$-alkyl, where such $R^{S2}$ substitutes a hydrogen atom in $R^{S1}$ being $C_1$-alkyl. In this example, the individual elements $R^{Sm}$ in —$[(R^{Sm})_6]$ are arranged in a "branched" fashion, since at least one $R^{Sx}$ (here, for example, $R^{S4}$ or $R^{S5}$) is linked to a $R^{Sy}$ (here $R^{S2}$) with x>y+1.

As will be readily apparent to anyone of ordinary skill in the art, there are manifold combinations of individual elements $R^S$ possible. However, as is apparent to one of ordinary skill in the art as well, there are certain combinations that result in are less favored arrangement and that will not be considered in the design and synthesis of compounds in accordance with the present invention, because of low stability, high reactivity, or unfavorable physicochemical properties, such as low solubility. Examples include, but are not limited to, semi-acetals or -ketals (—O—$CR_2$—OH), Michael systems (e.g. —C(=O)—CR=$CR_2$), α-halogen carbonyl compounds (e.g. —C(=O)—$CR_2$—Br), polycyclic aromatic systems, and the like.

In particular embodiments, the number of elements $R^S$ in a substituent —$[(R^{Sm})_n]$, that are selected from the lists (B) and (C) listed above, is not more than two. In particular embodiments, there is not more than one element $R^S$ in a substituent —$[(R^{Sm})_n]$, that is selected from the lists (B) or (C) listed above.

In particular embodiments, n in a substituent —$[(R^{Sm})_n]$ is any value from 1 to about 12, from 1 to about 10, from 1 to about 8, or from 1 to about 6.

In particular embodiments, n in a substituent —$[(R^{Sm})_n]$ for all substituents different from —F or —Cl is any value from 1 to about 6, from 1 to about 5, from 1 to about 4, or from 1 to about 3.

In particular embodiment, the number of atoms in a substituent —$[(R^{Sm})_n]$ is any value from 1 to about 80, from 1 to about 60, from 1 to about 50, from 1 to about 40, from 1 to about 30, from 1 to about 20, from 1 to about 15, or from 1 to about 10.

In particular embodiment, the combined molecular weight of all atoms in a substituent —$[(R^{Sm})_n]$ is any value from 1 to about 360, from 1 to about 300, from 1 to about 240, from 1 to about 180, from 1 to about 120, from 1 to about 90, or from 1 to about 60.

The term "halogen" or "halo" refers to fluoro, chloro, bromo and iodo substituents.

The terms "stereoisomer" and "tautomer" as used herein include all possible stereoisomeric and tautomeric forms of the compounds of the present invention. Where the compounds of the present invention contain one or more chiral centers, all possible enantiomeric and diastereomeric forms are included.

The present invention is intended to include all isotopes of atoms occurring on the present compounds. Isotopes are atoms having the same atomic number but different mass numbers. By way of general example and without limitation, isotopes of hydrogen include tritium and deuterium. Isotopes of carbon include $^{12}C$ and $^{14}C$.

The term "metabolite", as used herein, refers to any substance produced by the metabolism or by a metabolic process. Metabolism, as used herein, refers to the various physical/chemical/biochemical/pharmacological reactions involved in the transformation of molecules or chemical compounds occurring in the cell, tissue, system, body, animal, individual, patient or human therein.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

As used herein, an "individual" means a multi-cellular organism, for example an animal such as a mammal, including a primate. In addition to primates, such as humans, a variety of other mammals can be treated according to a method that utilizes one or more compounds of the present invention. For example, mammals including, but not limited to, cows, sheep, goats, horses, dogs, cats, guinea pigs, rats or other bovine, ovine, equine, canine, feline, rodent, or murine species can be used.

As used herein, a "proliferative disorder" or a "proliferative disease" includes a disease or disorder that affects a cellular growth, differentiation, or proliferation process.

As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic diseases or disorders.

As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a benign or malignant mass of tissue. Examples of cellular growth or proliferation disorders include, but are not limited to tumors, cancer, autoimmune diseases, viral diseases, fungal diseases, neurodegenerative disorders and cardiovascular diseases.

As used herein, the terms "anti-cancer agent" or "anti-proliferative agent" refer to compounds with anti-cancer and anti-proliferative properties, respectively. These compounds include, but are not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, picoplatin, LA-12, iproplatin, tetraplatin, lobaplatin, JM216, JM335, satraplatin, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, JM 118, etoposide, teniposide, vinblastine, vincristine, vinorelbine, procarbazine, asparaginase, pegaspargase, octreotide, estramustine, and hydroxyurea. Said terms also include, but are not limited to, non-small molecule therapeutics, such as antibodies, e.g., 1D09C3 and other anti-HLA-DR antibodies as described in WO 01/87337 and WO 01/97338, Rituxan as described in U.S. Pat. Nos. 5,736,137, 5,776,456, 5,843,437, 4D5, Mab225, C225, Daclizumab (Zenapax), Antegren, CDP 870, CMB-401, MDX-33, MDX-220, MDX-477, CEA-CIDE, AHM, Vitaxin, 3622W94, Therex, 5G1.1, IDEC-131, HU-901, Mylotarg, Zamyl (SMART M195), MDX-210, Humicade, LymphoCIDE, ABX-EGF, 17-1A, Trastuzumab (Herceptin®, rhuMAb), Epratuzumab, Cetuximab (Erbitux®), Pertuzumab (Omnitarg®, 2C4), R3, CDP860, Bevacizumab (Avastin®), tositumomab (Bexxar®), Ibritumomab tiuxetan (Zevalin®), M195, 1D10, Hu1D10 (Remitogen®, apolizumab), Danton/DN1924, an "HD" antibody such as HD4 or HD8, CAMPATH-1 and CAMPATH-1H or other variants, fragments, conjugates, derivatives and modifications thereof, or other equivalent compositions with improved or optimized properties, and proteins or peptides, e.g., those described in Trends in Biotechnology (2003), 21(12), p. 556-562.

As used herein, an "inflammatory disorder" or an "inflammatory disease" includes a disease or disorder that is caused or accompanied by inflammatory processes. This includes, but is not limited to, diseases or disorders such as arthritis, including but not limited to rheumatoid arthritis, spondyloarthropathies, gouty arthritis, osteoarthritis, systemic lupus erythematosus and juvenile arthritis, osteoarthritis, gouty arthritis and other arthritic conditions; pulmonary disorders or lung inflammation, including adult respiratory distress syndrome, pulmonary sarcoidosis, asthma, silicosis, and chronic pulmonary inflammatory disease; viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus; bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection; Alzheimer's disease, influenza, multiple sclerosis, cancer, diabetes, systemic lupus erythematosus (SLE), skin-related conditions such as psoriasis, eczema, burns, dermatitis, keloid formation, and scar tissue formation; gastrointestinal conditions such as inflammatory bowel disease, Crohn's disease, gastritis, irritable bowel syndrome and ulcerative colitis; ophthalmic diseases, such as retinitis, retinopathies, uveitis, ocular photophobia, and of acute injury to the eye tissue; angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma;

ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, EtOAc, ethanol, isopropanol, or acetonitrile are preferred. Lists of suitable salts are found in *Remington's Pharmaceutical Sciences*, 18th ed., Mack Publishing Company, Easton, Pa., 1990, p. 1445, the disclosure of which is hereby incorporated by reference.

Any salt that retains the desired biological activity of the compounds contained herein and that exhibits minimal or no undesired or toxicological effects is intended for inclusion here. Pharmaceutically acceptable salts include those derived from pharmaceutically acceptable organic or inorganic acids and bases. Non-pharmaceutically acceptable acids and bases also find use herein, as for example, in the synthesis and/or purification of the compounds of interest. Thus, all "salts" are also encompassed within the scope of the instant invention.

Non-limiting examples of suitable salts include those derived from inorganic acids, such as, for example, hydrochloric acid, hydrobromic acid, sulfuric acid, phosphoric acid, nitric acid, bicarbonic acid, carbonic acid; and salts formed with organic acids, such as, for example, formic acid, acetic acid, oxalic acid, tartaric acid, succinic acid, malic acid, malonic acid, ascorbic acid, citric acid, benzoic acid, tannic acid, palmoic acid, alginic acid, polyglutamic acid, toric acid, methanesulfonic acid, naphthalenesulfonic acid, naphthalenedisulfonic acid, α-ketoglutaric acid, β-glycerophosphoric acid and polygalacturonic acid. Suitable salts include those derived from alkali metals such as lithium, potassium and sodium, from alkaline earth metals such as calcium and magnesium, as well as from other acids well known to those of skill in the pharmaceutical art. Other suitable salts include those derived from metal cations such as zinc, bismuth, barium, or aluminum, or with a cation formed from an amine, such as ammonia, N,N-dibenzylethylenediamine, D-glucosamine, tetraethylammonium, or ethylenediamine. Moreover, suitable salts include those derived from a combination of acids and bases, such as, for example, a zinc tannate salt.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "prodrug", as used herein, refers to an agent that is converted into a pharmacologically active parent drug in vivo, such as a compound as defined herein. The term "prodrug" includes any covalently bonded carriers that release an active parent drug of the present invention in vivo when such prodrug is administered to an animal. Since prodrugs are known to enhance numerous desirable qualities of pharmaceuticals (e.g., solubility, bioavailability, manufacturing, transport, pharmacodynamics, etc.), the compounds of the present invention may be delivered in prodrug form. Prodrugs, for instance, may be bioavailable by oral administration even when the parent drug is not. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

From among the voluminous scientific literature devoted to prodrugs in general, the foregoing examples are cited: Gangwar et al., "Prodrug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984) 45-56 (Elsevier); Bundgaard et al. Int. J. of Pharmaceutics 29

(1986) 19-28 (Elsevier); Bundgaard et al. J. Med. Chem. 32 (1989) 2503-2507 Chem. Abstracts 93, 137935y (Bundgaard et al.); Chem. Abstracts 95, 138493f (Bundgaard et al.); Chem. Abstracts 95, 138592n (Bundgaard et al.); Chem. Abstracts 110, 57664p (Alminger et al.); Chem. Abstracts 115, 64029s (Buur et al.); Chem. Abstracts 115, 189582y (Hansen et al.); Chem. Abstracts 117, 14347q (Bundgaard et al.); Chem. Abstracts 117, 55790x (Jensen et al.); and Chem. Abstracts 123, 17593b (Thomsen et al.).

The terms "administered", "administration", or "administering" a compound will be understood to mean providing any compound of the invention to an individual, including an animal, in need of treatment by bringing such individual in contact with, or otherwise exposing such individual to, such compound.

The term "in vitro" refers to a biological entity, a biological process, or a biological reaction outside the body in artificial conditions. For example a cell grown in vitro is to be understood as a cell grown in an environment outside the body, e.g., in a test tube, a culture tray or a microtiter plate.

The term "therapeutically effective amount" means the amount of the subject compound that will elicit the biological, physiological, pharmacological, therapeutic or medical response of a cell, tissue, system, body, animal, individual, patient or human that is being sought by the researcher, scientist, pharmacologist, pharmacist, veterinarian, medical doctor, or other clinician, e.g., lessening of the effects/symptoms of a disorder or disease, such as a proliferative disorder or disease, for example, a cancer or tumor, or killing or inhibiting growth of a proliferating cell, such as a tumor cell. The therapeutically effective amount can be determined by standard procedures, including those described below in the section "Dosages".

The term "further treated", "further administer", or "further administered" means that different therapeutic agents or compounds may be administered together, alternatively or intermittently. Such further administration may be temporally or spatially separated, for example, at different times, on different days or via different modes or routes of administration.

Certain Compounds of the Present Invention

One aspect of the invention relates to a compound having a structure represented by formula (I) or any tautomeric or stereoisomeric form thereof, wherein one or more hydrogen atoms in moieties indicated as being "substituted or unsubstituted" in one or more of $R^1$, $R^5$ and/or $R^6$ may be independently substituted by one or more substituents —[($R^{Sm}$)$_n$], as described above.

Table 4 shows a selection of exemplary compounds of the present invention having a substituted aryl or heteroaryl as $R^6$, i.e. a group —$R^6$—[($R^{Sm}$)$_n$], and how the substituent —[($R^{Sm}$)$_n$] can be dissected in each case.

One aspect of the invention relates to a compound having a structure represented by formula (I) or any tautomeric or stereoisomeric form thereof as defined above, wherein R1 is not substituted or unsubstituted —NH-pyrid-2-yl.

One aspect of the invention relates to a compound having a structure represented by formula (I) or any tautomeric or stereoisomeric form thereof, wherein R1 is selected from hydrogen, —NH$_2$, and substituted or unsubstituted: —NH—C$_{1-6}$-alkyl, —NH-cycloalkyl, —NH-heterocycloalkyl, —NH—C$_{1-6}$-alkylene-OR$^7$, and —NH—C$_{1-6}$-alkylene-NR$^7_2$ and wherein $R^2$, $R^3$, $R^4$, $R^5$, and $R^7$ are as defined above.

One further aspect of the invention relates to a compound having a structure represented by formula (I) or any tautomeric or stereoisomeric form thereof, wherein $R^1$ is substituted or unsubstituted —NH—C$_{1-6}$-alkylene-NR$^7_2$, and wherein $R^2$, $R^3$, $R^4$, $R^5$, and $R^7$ are as defined above.

Another aspect of the invention relates to a compound having a structure represented by formula (I) or any tautomeric or stereoisomeric form thereof, wherein $R^2$ is selected from hydrogen and chlorine, and wherein $R^1$, $R^3$, $R^4$, and $R^5$ are as defined above. In certain embodiments, $R^2$ is -chlorine.

Another aspect of the invention relates to a compound having a structure represented by formula (I) or any tautomeric or stereoisomeric form thereof, wherein $R^3$ is hydrogen and $R^4$ is —NH—C(=O)—(NH)$_x$—(CH$_2$)$_y$—$R^6$, wherein x any y are independently selected from 0 and 1, and wherein $R^1$, $R^2$, $R^5$ and $R^6$ are as defined above. In a particular embodiment, y is 0.

Another aspect of the invention relates to a compound having a structure represented by formula (I) or any tautomeric or stereoisomeric form thereof, wherein $R^4$ is hydrogen and $R^3$ is —NH—C(=O)—(NH)$_x$—(CH$_2$)$_y$—$R^6$, wherein x any y are independently selected from 0 and 1, and wherein $R^1$, $R^2$, $R^5$ and $R^6$ are as defined above. In certain embodiments, x is 0. In other embodiments, y is 0. In particular embodiments, x and y are 0.

Another aspect of the invention relates to a compound having a structure represented by formula (I) or any tautomeric or stereoisomeric form thereof, wherein $R^5$ is selected from substituted or unsubstituted: -alkyl and -cycloalkyl, and wherein $R^1$, $R^2$, $R^3$, and $R^4$ are as defined above. In certain embodiments, $R^5$ is selected from substituted or unsubstituted: —C$_{1-6}$-alkyl and —C$_{3-8}$-cycloalkyl. In certain embodiments, $R^5$ is substituted or unsubstituted —C$_{1-6}$-alkyl, and in particular embodiments, $R^5$ is methyl.

Those skilled in the art will recognize that all specific combinations of the individual possible residues of the variable regions of the compounds as disclosed herein, i.e. $R^1$, $R^2$, $R^3$, $R^4$, and $R^5$ are within the scope of the invention.

In one embodiment of the present invention, compounds of the invention have a molecular weight of between 350 and 1000, particularly between 400 and 800, more particularly between 400 and 600, and even more particularly between 400 and 550. In certain embodiments, compounds of the invention have one or more of the following characteristics: (i) not more than 5 hydrogen bond donors, (ii) not more than 10 hydrogen bond acceptors, and (iii) not more than 10 rotatable bonds (excluding bonds to terminal atoms). In certain embodiments, the compounds of formula (I) are in accordance with Lipinski's "Rule of Five" (Lipinski, Adv. Drug Del. Rev. 1997; 23: 3), by having a molecular weight below 500, not more than 5 hydrogen bond donors, not more than 10 hydrogen bond acceptors, and a cLogP value between −2 and 5.

In one embodiment of the present invention, compounds of the invention are inhibitors of the activity of B-Raf. In certain embodiments, the compounds of the present invention inhibit B-Raf activity with IC$_{50}$ values below 1 µM, such IC$_{50}$ value being determined in accordance with the B-Raf inhibition assay described in the examples shown below. In certain embodiments, the IC$_{50}$ value is below 0.5 µM, below 0.2 µM, below 0.1 µM, or below 0.01 µM.

In another embodiment of the present invention, compounds of the invention are inhibitors of the activity of p38. In certain embodiments, the compounds of the present invention inhibit p38 activity with IC$_{50}$ values below 1 µM. In certain embodiments, the IC$_{50}$ value is below 0.5 µM, below 0.2 µM, below 0.1 µM, or below 0.01 µM.

In one embodiment of the present invention, compounds of the invention have a purity of more than 90%, more than 95%, more than 98%, or more than 99%. Such compounds may exist in one or more crystalline forms, including two or more polymorphic forms, and may exist as dry solids or as solvates including defined amounts of solvents, including hydrates including defined amounts of water.

In another embodiment, compounds of the invention are the planned and deliberate products of a synthetic chemistry scheme, i.e., produced by specific and planned chemical processes conducted in reaction vessels, and not by degradation, metabolism or fermentation, or produced as impurities or by-products in the synthesis of other compounds.

In certain embodiments, compounds of the invention are purified or isolated, e.g., to have a purity of at least 80%, preferably at least 90%, more preferably at least 95%, such as at least 97%, at least 98% or even at least 99%. Purity, as used herein, can refer to either absolute or relative purity. Absolute purity refers to the amount of a compound of the invention obtained as the product of a synthetic chemistry scheme, either before or after one or more purification steps. Relative purity refers to the amount of a compound of the invention relative to one or more impurities such as by-products, degradation products (e.g., metabolites, products of oxidation or hydrolysis, etc.) and/or compounds that degrade to form a compound of the invention (e.g., precursors or prodrugs), e.g., that may be present in the product of a synthetic chemistry scheme. Thus, absolute purity refers to the amount of a compound relative to all others, while relative purity is generally unaffected by the addition of unrelated compounds, such as excipients, stabilizers, or other medicaments for conjoint administration. Purity can be assessed based upon weight, volume or molar ratios of one compound relative to others. Purity can be measured by a variety of analytical techniques, including elemental abundance, UV-visible spectrometry, HPLC, GC-MS, NMR, mass spectrometry, and thin layer chromatography, preferably by HPLC, GC-MS, or NMR.

Yet another aspect of the invention relates to prodrugs of a compound described above.

Particular Embodiments

In a particular aspect, the invention relates to a compound represented by a structure of formula (Ia)

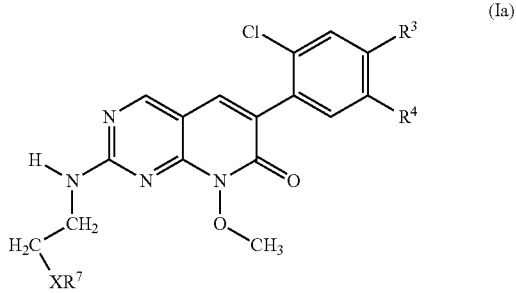

(Ia)

or any tautomeric or stereoisomeric form thereof, wherein X is selected from —O— and —NR$^7$—, and wherein R$^3$, R$^4$, and R$^7$ are as defined above, provided, however, that compound (A) is excluded:

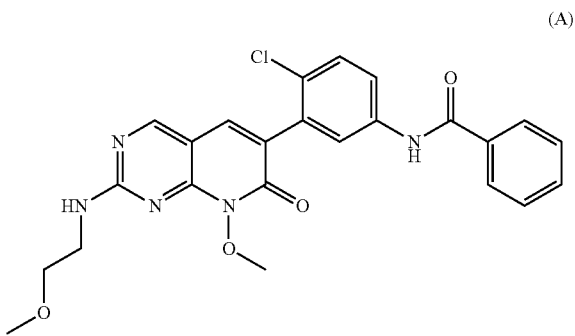

(A)

In certain embodiments, X is —NR$^7$—. In particular such embodiments, both R$^7$ are methyl.

In other certain embodiments, R$^3$ is hydrogen and R$^4$ is —NH—C(=O)—(NH)$_x$—(CH$_2$)$_y$—R$^6$, wherein x any y are independently selected from 0 and 1, and R$^6$ is as defined above. In a particular embodiment, y is 0.

In other certain embodiments, R$^4$ is hydrogen and R$^3$ is —NH—C(=O)—(NH)$_x$—(CH$_2$)$_y$—R$^6$, wherein x any y are independently selected from 0 and 1, and R$^6$ is as defined above. In certain embodiments, x is 0. In other embodiments, y is 0. In particular embodiments, x and y are 0.

In certain embodiments of Formula I, the compound is selected from:

4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-3-trifluoromethyl-benzamide 5-tert-Butyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide 3,4-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide 5-tert-Butyl-2-methyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide N-{4-Chloro-3-[2-(2-dimethylamino-ethylamino)-8-methoxy-7-oxo-7,8-dihydro-pyrido[2,3-d]pyrimidin-6-yl]-phenyl}-3-fluoro-4-trifluoromethyl-benzamide 1-Methyl-1H-indole-2-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide N-{4-Chloro-3-[2-(2-dimethylamino-ethylamino)-8-methoxy-7-oxo-7,8-dihydro-pyrido [2,3-d]pyrimidin-6-yl]-phenyl}-2-methoxy-5-trifluoromethyl-benzamide N-{4-Chloro-3-[2-(2-dimethylamino-ethylamino)-8-methoxy-7-oxo-7,8-dihydro-pyrido [2,3-d]pyrimidin-6-yl]-phenyl}-2-methoxy-4-trifluoromethyl-benzamide N-{4-Chloro-3-[2-(2-dimethylamino-ethylamino)-8-methoxy-7-oxo-7,8-dihydro-pyrido [2,3-d]pyrimidin-6-yl]-phenyl}-2-(4-chloro-3-trifluoromethyl-phenyl)-acetamide N-{4-Chloro-3-[2-(2-dimethylamino-ethylamino)-8-methoxy-7-oxo-7,8-dihydro-pyrido [2,3-d]pyrimidin-6-yl]-phenyl}-4-fluoro-3-trifluoromethyl-benzamide 3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide 5-tert-Butyl-N-{4-chloro-3-[2-(2-dimethylamino-ethylamino)-8-methoxy-7-oxo-7,8-dihydro-pyrido[2,3-d]pyrimidin-6-yl]-phenyl}-2-methoxy-benzamide N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-4-trifluoromethyl-benzamide 3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-4-methoxy-benzamide 3,5-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-5-trifluoromethyl-benzamide N-{4-Chloro-3-[2-(2-dimethylamino-ethylamino)-8-methoxy-7-oxo-7,8-dihydro-pyrido [2,3-d]pyrimidin-6-yl]-phenyl}-3-trifluoromethyl-benzamide N-{4-Chloro-3-[2-(2-dimethylamino-ethylamino)-8-methoxy-7-oxo-7,8-dihydro-pyrido [2,3-d]pyrimidin-6-yl]-phenyl}-2-(3-trifluoromethyl-phenyl)-acetamide
N-{4-Chloro-3-[2-(2-dimethylamino-ethylamino)-8-methoxy-7-oxo-7,8-dihydro-pyrido [2,3-d]pyrimidin-6-yl]-phenyl}-2-morpholin-4-yl-isonicotinamide
N-{4-Chloro-3-[2-(2-dimethylamino-ethylamino)-8-methoxy-7-oxo-7,8-dihydro-pyrido [2,3-d]pyrimidin-6-yl]-phenyl}-4-phenoxy-benzamide
N-{4-Chloro-3-[2-(2-dimethylamino-ethylamino)-8-methoxy-7-oxo-7,8-dihydro-pyrido [2,3-d]pyrimidin-6-yl]-phenyl}-3-fluoro-5-trifluoromethyl-benzamide
2-Chloro-N-{4-chloro-3-[2-(2-dimethylamino-ethylamino)-8-methoxy-7-oxo-7,8-dihydro-pyrido [2,3-d]pyrimidin-6-yl]-phenyl}-5-trifluoromethyl-benzamide
4-Chloro-N-{4-chloro-3-[2-(2-dimethylamino-ethylamino)-8-methoxy-7-oxo-7,8-dihydro-pyrido [2,3-d]pyrimidin-6-yl]-phenyl}-3-trifluoromethoxy-benzamide
5-tert-Butyl-2-phenyl-2H-pyrazole-3-carboxylic acid {4-chloro-3-[2-(2-dimethylamino-ethylamino) -8-methoxy-7-oxo-7,8-dihydro-pyrido[2,3-d]pyrimidin-6-yl]-phenyl}-amide
3-Chloro-N-{4-chloro-3-[2-(2-dimethylamino-ethylamino)-8-methoxy-7-oxo-7,8-dihydro-pyrido [2,3-d]pyrimidin-6-yl]-phenyl}-4-(3-fluoro-benzyloxy)-benzamide
N-{4-Chloro-3-[2-(2-dimethylamino-ethylamino)-8-methoxy-7-oxo-7,8-dihydro-pyrido [2,3-d]pyrimidin-6-yl]-phenyl}-benzamide
N-{4-Chloro-3-[2-(2-dimethylamino-ethylamino)-8-methoxy-7-oxo-7,8-dihydro-pyrido [2,3-d]pyrimidin-6-yl]-phenyl}-4-trifluoromethyl-benzamide
N-{4-Chloro-3-[2-(2-dimethylamino-ethylamino)-8-methoxy-7-oxo-7,8-dihydro-pyrido [2,3-d]pyrimidin-6-yl]-phenyl}-3,5-bis-trifluoromethyl-benzamide
2-Chloro-N-{4-chloro-3-[2-(2-dimethylamino-ethylamino)-8-methoxy-7-oxo-7,8-dihydro-pyrido [2,3-d]pyrimidin-6-yl]-phenyl}-benzamide
4-tert-Butyl-N-{4-chloro-3-[2-(2-dimethylamino-ethylamino)-8-methoxy-7-oxo-7,8-dihydro-pyrido[2,3-d]pyrimidin-6-yl]-phenyl}-benzamide
4-Chloro-N-{4-chloro-3-[2-(2-dimethylamino-ethylamino)-8-methoxy-7-oxo-7,8-dihydro-pyrido [2,3-d]pyrimidin-6-yl]-phenyl}-benzamide
N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-3-trifluoromethyl-benzamide
6-Fluoro-1H-benzoimidazole-2-carboxylic acid {4-chloro-3-[2-(2-dimethylamino-ethylamino) -8-methoxy-7-oxo-7,8-dihydro-pyrido[2,3-d]pyrimidin-6-yl]-phenyl}-amide
1-{4-Chloro-3-[2-(2-dimethylamino-ethylamino)-8-methoxy-7-oxo-7,8-dihydro-pyrido [2,3-d]pyrimidin-6-yl]-phenyl}-3-(3-chloro-4-methoxy-phenyl)-urea
1-{4-Chloro-3-[2-(2-dimethylamino-ethylamino)-8-methoxy-7-oxo-7,8-dihydro-pyrido [2,3-d]pyrimidin-6-yl] phenyl}-3-(4-trifluoromethyl-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-fluoro-3-trifluoromethyl-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(3-chloro-phenyl)-urea
1-(4-tert-Butyl-phenyl)-3-{4-chloro-3-[2-(2-dimethylamino-ethylamino)-8-methoxy-7-oxo-7,8-dihydro-pyrido[2,3-d]pyrimidin-6-yl]-phenyl}-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-phenoxy-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-chloro-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-methyl-3-trifluoromethyl-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(2-fluoro-3-trifluoromethyl-phenyl)-urea
1-{4-Chloro-3-[2-(2-dimethylamino-ethylamino)-8-methoxy-7-oxo-7,8-dihydro-pyrido [2,3-d]pyrimidin-6-yl]-phenyl}-3-(2-fluoro-5-trifluoromethyl-phenyl)-urea
1-(3,5-Bis-trifluoromethyl-phenyl)-3-{4-chloro-3-[2-(2-dimethylamino-ethylamino)-8-methoxy-7-oxo-7,8-dihydro-pyrido[2,3-d]pyrimidin-6-yl]-phenyl}-urea
4-Chloro-N-{3-chloro-4-[2-(2-dimethylamino-ethylamino)-8-methoxy-7-oxo-7,8-dihydro-pyrido [2,3-d]pyrimidin-6-yl]-phenyl}-3-trifluoromethyl-benzamide
N-{3-Chloro-4-[2-(2-dimethylamino-ethylamino)-8-methoxy-7-oxo-7,8-dihydro-pyrido [2,3-d]pyrimidin-6-yl]-phenyl}-2-methoxy-4-trifluoromethyl-benzamide
4-Chloro-N-{3-chloro-4-[2-(2-dimethylamino-ethylamino)-8-methoxy-7-oxo-7,8-dihydro-pyrido [2,3-d]pyrimidin-6-yl]-phenyl}-3-trifluoromethoxy-benzamide
N-{3-Chloro-4-[2-(2-dimethylamino-ethylamino)-8-methoxy-7-oxo-7,8-dihydro-pyrido [2,3-d]pyrimidin-6-yl]-phenyl}-4-(4-methyl-piperazin-1-ylmethyl)-benzamide
N-{3-Chloro-4-[2-(2-dimethylamino-ethylamino)-8-methoxy-7-oxo-7,8-dihydro-pyrido [2,3-d]pyrimidin-6-yl]-phenyl}-2-morpholin-4-yl-isonicotinamide
3-Chloro-N-{3-chloro-4-[2-(2-dimethylamino-ethylamino)-8-methoxy-7-oxo-7,8-dihydro-pyrido [2,3-d]pyrimidin-6-yl]-phenyl}-4-(3-fluoro-benzyloxy)-benzamide
5-tert-Butyl-2-phenyl-2H-pyrazole-3-carboxylic acid {3-chloro-4-[2-(2-dimethylamino-ethylamino) -8-methoxy-7-oxo-7,8-dihydro-pyrido[2,3-d]pyrimidin-6-yl]-phenyl}-amide
N-{3-Chloro-4-[2-(2-dimethylamino-ethylamino)-8-methoxy-7-oxo-7,8-dihydro-pyrido [2,3-d]pyrimidin-6-yl]-phenyl}-2-(4-chloro-3-trifluoromethyl-phenyl)-acetamide
2,6-Dichloro-N-(4-chloro-3-(2-(2-(dimethylamino)ethylamino)-8-methoxy-7-oxo-7,8-dihydropyrido[2,3-d]pyrimidin-6-yl)phenyl)-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-pyrrolidin-1-yl-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-dimethylamino-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-pyperidin-1-yl-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-morpholin-4-yl-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(4-methyl-piperazin-1-yl)-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-diethylamino-isonicotinamide
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-ethylamino-isonicotinamide 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-isopropylamino-isonicotinamide 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(2-dimethylaminoethylamino)-isonicotinamide 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-1-methyl-piperidine-4-ylamino)-isonicotinamide 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(4-(4-methylpiperazin-1-yl)-benzylamino)-isonicotinamide N-(4-chloro-3-(8-methoxy-2-(2-methoxy-ethylamino)-7-oxo-7,8-dihydropyrido[2,3-d]pyrimidin-6-yl)-phenyl)-benzamide N-(4-chloro-3-(2-ethylamino-8-methoxy-7-oxo-7,8-dihydropyrido[2,3-d]pyrimidin-6-yl)phenyl)-3-trifluormethyl-benzamide N-(3-(2-amino-8-methoxy-7-oxo-7,8-dihydropyrido[2,3-d]pyrimidin-6-yl)-4-chloro-phenyl) -3-trifluormethyl-benzamide N-(4-chloro-3-(8-methoxy-7-oxo-7,8-dihydropyrido[2,3-d]pyrimidin-6-yl)-phenyl)-3-trifluormethyl-benzamide N-{4-Chloro-3-[2-(3-dimethylamino-propylamino)-8-methoxy-7-oxo-7,8-dihydro-pyrido [2,3-d]pyrimidin-6-yl]-phenyl}-3-trifluoromethyl-benzamide;

where such compounds have the structures as disclosed in Table 1 below. In case of a discrepancy between the chemical name given above and the corresponding structure shown in Table 1, the structure should be regarded as correct, and the name amended accordingly.

Formulations, Dosages and Applications

The present invention further provides a pharmaceutical composition including a compound as described above, or prodrug thereof, and a pharmaceutically acceptable diluent, excipient or carrier, including pharmaceutical compositions including a therapeutically effective amount of such compound or prodrug.

Formulations

The compositions of this invention can be formulated and administered to treat individuals in need by any means that produces contact of the active ingredient with the agent's site of action, such as a cell, in the body of an individual. They can be administered by any conventional means available for use in conjunction with pharmaceuticals, either as individual therapeutic active ingredients or in a combination of therapeutic active ingredients. They can be administered alone, but are generally administered with a pharmaceutically acceptable diluent, excipient or carrier selected on the basis of the chosen route of administration and standard pharmaceutical practice.

A pharmaceutical composition comprising less than a therapeutically effective amount of any of the compounds described above, or a prodrug thereof, may also be used, such as when used in combination with another pharmaceutical composition, such as an anti-cancer agent, so that such combination is therapeutically effective, or may be useful for prophylactic treatment.

Pharmaceutical compositions for use in accordance with the present invention may be formulated in conventional manner using one or more pharmaceutically acceptable diluents, excipients or carriers. The pharmaceutical compositions of the invention can be formulated for a variety of routes of administration, including systemic and topical or localized administration. Techniques and formulations generally may be found in Remington's Pharmaceutical Sciences, Meade Publishing Co., Easton, Pa. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, capsules, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments, the pharmaceutical preparations may be non-pyrogenic, i.e., do not substantially elevate the body temperature of a patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

For systemic administration, injection is preferred, including intramuscular, intravenous, intraperitoneal, and subcutaneous (i.m., i.v., i.p., and s.c. respectively). The phrases "systemic administration", "administered systemically", "peripheral administration", and "administered peripherally" as used herein mean the administration of a compound, drug or other material other than directly into the central nervous system, such that it enters the patient's system and, thus, is subject to metabolism and other like processes, for example, subcutaneous administration.

For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

Pharmaceutical compositions of the invention may be formulated to be suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In formulating the pharmaceutical compositions of the invention in solid dosage forms for oral (p.o.) administration (capsules, tablets, pills, dragees, powders, granules and the like), a compound of the invention as active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, high molecular weight polyethylene glycols, and the like.

Gelatin capsules contain a compound of the present invention as active ingredient and powdered carriers, such as lactose, starch, cellulose derivatives, magnesium stearate, stearic acid, and the like. Similar carriers can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol, or Capmul, in a soft gelatin capsule. Antioxidants may be added to prevent long-term degradation as appropriate.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor moistened with an inert liquid diluent.

The tablets and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the pharmaceutical compositions of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the pharmaceutical compositions for oral administration can also include adjuvants such as wetting agents, emulsifying and suspending agents, sweetening, flavoring, coloring, perfuming, and preservative agents.

Suspensions, in addition to the pharmaceutical composition of the present invention, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For buccal administration the pharmaceutical compositions may take the form of tablets or lozenges formulated in a conventional manner.

For administration by inhalation, the pharmaceutical compositions of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the therapeutic agents and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more inhibitors of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents that delay absorption such as aluminum monostearate and/or gelatin.

In addition to the formulations described previously, the pharmaceutical compositions may also be formulated as a depot preparation. Such long acting formulations may be administered by implantation (for example subcutaneously or intramuscularly) or by intramuscular injection. Thus, for example, the pharmaceutical compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the pharmaceutical compositions of the invention are formulated into ointments, salves, gels, or creams as generally known in the art. A wash solution can be used locally to treat an injury or inflammation to accelerate healing.

In some cases, in order to prolong the therapeutic effect of an inhibitor, it is desirable to slow the absorption of the inhibitor from subcutaneous or intramuscular injection. This may be accomplished by the use of a liquid suspension of crystalline or amorphous material having poor water solubility. The rate of absorption of the inhibitor then depends upon its rate of dissolution which, in turn, may depend upon crystal size and crystalline form. Alternatively, delayed absorption of a parenterally administered inhibitor form is accomplished by dissolving or suspending the inhibitor in an oil vehicle.

Pharmaceutical compositions of the invention may be formulated for rectal or vaginal administration as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the pharmaceutical compositions of the present invention, which are suitable for vaginal administration, also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. Such compound may be mixed under sterile conditions with a pharmaceutically acceptable carrier, and with any preservatives, buffers, or propellants which may be required.

The ointments, pastes, creams and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing an inhibitor of the present invention in the proper medium. Absorption enhancers can also be used to increase the flux of the drug across the skin. The rate of such flux can be controlled by either providing a rate controlling membrane or dispersing the compound of the present invention in a polymer matrix or gel.

Ophthalmic formulations, eye ointments, powders, solutions and the like, are also contemplated as being within the scope of this invention.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In other embodiments, the pack or dispenser may be further packaged in an outer carton.

A pharmaceutical composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydroxypropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

Injectable depot forms are made by forming microencapsuled matrices of the subject inhibitors in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds of the present invention are administered as pharmaceuticals, to individuals, such as humans and animals, they can be given per se or as a pharmaceutical composition containing, for example, 0.1 to 99.5% (in certain embodiments, 0.5 to 90%) of active ingredient in combination with a pharmaceutically acceptable carrier.

The present invention provides new methods of treating proliferative, degenerative and other disorders or diseases, including cancer, by administering an amount such as a therapeutically effective amount of at least one of the compounds disclosed herein or a prodrug, tautomeric, pharmaceutically acceptable salt, N-oxide or stereoisomeric form thereof. The present invention further provides methods of treating proliferative, degenerative or other disorders or diseases, including cancer, by administering a therapeutically effective combination of at least one of these compounds and another anticancer or anti-proliferative agent.

A compound of the present invention may be administered as a salt or prodrug that, upon administration to the individual, is capable of providing directly or indirectly the parent compound, such as a compound as defined herein, or that exhibits activity itself. Nonlimiting examples include a pharmaceutically acceptable salt, alternatively referred to as a "physiologically acceptable salt". In addition, modifications made to a compound can affect its biological activity, in some cases increasing the activity over the parent compound. This activity can be assessed by preparing a salt or prodrug form of the compound, and testing its activity by using methods described herein or other methods known to those of skill in the art.

As will be apparent to a person skilled in the art, through the use of a prodrug of a given subject compound, an individual such as an animal administered or treated with such prodrug will be exposed to, and hence indirectly administered with, the subject compound. Such a procedure may expose those cells associated with a disease, such as a proliferative disease or disorder including cancer, to the subject compound.

The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated. All processes used to prepare compounds of the present invention and intermediates made therein are considered to be part of the present invention.

Dosages

A dosage administered that will be a therapeutically effective amount of the compound sufficient, or reasonably expected by a health-care professional such as a physician, pharmacist or nurse, to result in amelioration of symptoms of, for example, the cancer or tumor will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The subject compounds may also be administered in prophylactic treatment. If the compound is administered prior to clinical manifestation of the unwanted condition (e.g., disease or other unwanted state of the host animal) then the treatment is prophylactic (i.e., it protects the individual against initiating, developing or further developing the unwanted condition). The subject compounds may also be administered to prevent a condition, disorder or diseases, such as cancer, or a syndrome complex, such as heart failure or any other medical condition. This includes administration of a compound the intent of which is to reduce the frequency of, or delay the onset of, symptoms of a medical condition in an individual relative to an individual which does not receive the compound. Thus, prevention of cancer includes, for example, reducing the number of detectable cancerous growths, tumors, or malignancies in a population of patients receiving a prophylactic treatment relative to an untreated control population, delaying the appearance of detectable cancerous growths in a treated population versus an untreated control population, and/or delaying disease progression and/or improving the quality of patient life, e.g., by a statistically and/or clinically significant amount.

Toxicity and therapeutic efficacy of pharmaceutical compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful for many circumstances. In certain circumstances, even therapeutic compositions that appear to exhibit debilitating or toxic side effects may be used, including circumstances where care is taken to design a delivery system that targets such therapeutic agents to the site of affected tissue in order to minimize potential damage to unaffected cells and, thereby, reduce or localize side effects.

The data obtained from cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized. For any agents used in the method of the invention, the therapeutically effective dose can be estimated initially from cell culture assays. A dose may be formulated in animal models to achieve a circulating plasma concentration range that includes the $IC_{50}$ (i.e., the concentration of the test therapeutic agent which achieves a half-maximal inhibition of symptoms or inhibition of biochemical activity) as determined in cell culture. Such information can be used to more accurately determine useful doses in humans. Levels in plasma may be measured, for example, by high performance liquid chromatography.

It is understood that appropriate doses of therapeutic agents depends upon a number of factors known to those or ordinary skill in the art, e.g., a physician. The dose(s) of the subject compounds will vary, for example, depending upon the identity, size, and condition of the subject or sample being treated, further depending upon the route by which the composition is to be administered, if applicable, and the effect which the practitioner desires the therapeutic to have upon the therapeutic target of targets, such as cells, nucleic acid or polypeptides, through with the disease causes, symptoms or effects are mediated.

Exemplary doses include milligram or microgram amounts of the compounds of the present invention per kilogram of subject or sample weight, e.g., about 1 microgram per kilogram to about 500 milligrams per kilogram, about 100 micrograms per kilogram to about 50 milligrams per kilogram, or about 1 milligram per kilogram to about 5 milligrams per kilogram.

A person skilled in the art will appreciate that doses can also be calculated on a body surface basis. A person of 70 kg has an approximate body surface area of 1.8 square meter, and doses can be expressed as milligram or microgram amounts of the compound per body surface area of subject or sample, e.g. about 50 microgram per square meter to about 15 grams per square meter, about 5 milligrams per square meter to about 1.5 grams per square meter, or about 50 milligram per square meter to about 150 milligrams per square meter.

Applications

The present invention further provides the compounds as described above for therapy. In other aspects, the invention provides the compounds of the present invention for prophylatic uses.

In certain embodiments, said therapy or prophylactic use is the treatment or prevention of a proliferative disorder or disease, such as a tumor or cancer. In certain embodiments, said treatment is the treatment of a cancer that can be treated by the inhibition of the activity of a protein kinase or mutant thereof, such as the inhibition of the activity of B-Raf or mutants thereof.

In certain other embodiments, said therapy or prophylactic use is the treatment or prevention of an inflammatory disorder or disease. In certain embodiments, said treatment is the treatment of an inflammatory disorder or disease that can be treated by the inhibition of the activity of a protein kinase or mutant thereof, such as the inhibition of the activity of p38 or an isoform thereof.

Thus, the present invention additionally provides a method for treating an individual, such as a mammal, having a disease-state selected from the group of proliferative disorders or diseases, or inflammatory disorders or diseases, comprising administering to said individual a therapeutically effective amount of a compound, a prodrug, or a pharmaceutical composition of the invention as described above. In certain embodiments, said individual is a human. In certain embodiments, said proliferative disorder or disease is cancer. In certain embodiments, said treatment is the treatment of a cancer that can be treated by the inhibition of the activity of a protein kinase or mutant thereof, such as the inhibition of the activity of B-Raf or mutants thereof. In certain embodiments, said treatment is the treatment of the treatment of an inflammatory disorder or disease that can be treated by the inhibition of the activity of a protein kinase or mutant thereof, such as the inhibition of the activity of p38 or an isoform thereof.

The present invention also provides a method for prophylactic treatment of an individual such as an animal, including a mammal, particularly a human, the intent of which is to reduce the frequency of, delay the onset of, or the symptoms of a medical condition, such as cancer, in a subject relative to a subject which does not receive the composition.

In a further aspect, the invention provides methods of treating or preventing an individual suffering from a disease, such as a mammal, including a domestic mammal, cat, dog, horse, sheep, cow, rodent, and human, comprising the step of exposing said individual to an amount, including a therapeutically effective amount, of a subject compound. In certain embodiments, the disease is a proliferative disorder or disease, such as a cancer or tumour. In yet another embodiment, cells associated with said proliferative disorder or disease, including tumour cells included in a cancer, are exposed to the subject compound. In certain embodiments, said compound, or a prodrug thereof, is administered to said individual. In certain embodiments, said treatment is the treatment of a cancer that can be treated by the inhibition of the activity of a protein kinase or mutant thereof, such as the inhibition of the activity of B-Raf or mutants thereof. In certain embodiments, the disease is an inflammatory disorder or disease. In yet another embodiment, cells associated with said inflammatory disorder or disease are exposed to the subject compound. In certain embodiments, said compound, or a prodrug thereof, is administered to said individual. In certain embodiments, said treatment is the treatment of an inflammatory disease or disorder that can be treated by the inhibition of the activity of a protein kinase or mutant thereof, such as the inhibition of the activity of p38 or an isoform thereof.

In a further aspect, the invention provides a method of killing or inhibiting proliferation or growth of a cell, comprising contacting the cell with a compound of the invention. In one embodiment, the cell is cultured in-vitro, while in an alternative embodiment the cell is present in an individual. In a particular embodiment the cell is a cancer cell, for example a cell from a tumour cell line or a cell included in a tumour, including cancer cells from a tumour that can be treated by the inhibition of the activity of a protein kinase or mutant thereof, such as the inhibition of the activity of B-Raf or mutants thereof.

Yet another aspect of the invention relates to the use of a compound as described above, or a prodrug thereof, for the preparation of a medicament for the treatment or prevention of a proliferative disorder or disease, including cancer, including cancers that can be treated by the inhibition of the activity of a protein kinase or mutant thereof, such as the inhibition of the activity of B-Raf or mutants thereof. Additionally, the invention relates to a pharmaceutical composition comprising a compound as described above, or a prodrug thereof, and a pharmaceutically acceptable diluent, excipient or carrier, for the treatment of a proliferative disorder or disease, including cancer, including cancers that can be treated by the inhibition of the activity of a protein kinase or mutant thereof, such as the inhibition of the activity of B-Raf or mutants thereof.

Yet another aspect of the invention relates to the use of a compound as described above, or a prodrug thereof, for the preparation of a medicament for the treatment or prevention of an inflammatory disorder or disease, including inflammatory disorders or diseases that can be treated by the inhibition of the activity of a protein kinase or mutant thereof, such as the inhibition of the activity of p38 or an isoform thereof. Additionally, the invention relates to a pharmaceutical composition comprising a compound as described above, or a prodrug thereof, and a pharmaceutically acceptable diluent, excipient or carrier, for the treatment of an inflammatory disorder or disease, including cancers that can be treated by the inhibition of the activity of a protein kinase or mutant thereof, such as the inhibition of the activity of p38 or an isoform thereof.

The subject compounds are useful to treat various disorders or diseases, including proliferative disorders or diseases, and inflammatory disorders or diseases. The term "proliferative disorder or disease" is also art recognized and includes a disorder or disease affecting an individual, such as an animal, in a manner which is marked by aberrant, or otherwise unwanted, proliferation of a subset of cells of an individual. Cancer and tumors are proliferative disorders or diseases. Cells comprising or derived from a tumor will generally be understood to be a proliferating cell, typically a hyper-proliferating cell, and in other circumstances, a tumor cell may be dysplastic, or may have proliferated. In certain embodiments, said treatment is the treatment of a cancer that can be treated by the inhibition of the activity of a protein kinase or mutant thereof, such as the inhibition of the activity of B-Raf or mutants thereof.

It will be apparent to a person skilled in the art, on reading the disclosure of the instant invention, that the methods, pharmaceutical compositions and packaged pharmaceuticals comprising the subject compounds will be useful for the treatment of other proliferative disorders or diseases, or for killing or inhibiting proliferating cells including tumor cells.

Compounds of the present invention may be useful in the treatment of disease processes which feature abnormal cellular proliferation, such as hyperproliferative diseases, including cancer, benign prostate hyperplasia, familial adenomatosis polyposis, neurofibromatosis, psoriasis, fungal infections, endotoxic shock, hypertrophic scar formation, inflammatory bowel disease, transplant rejection, vascular smooth muscle cell proliferation associated with atherosclerosis, psoriasis, pulmonary fibrosis, arthritis, glomerulonephritis, restenosis following angioplasty or vascular surgery, and other post-surgical stenosis and restenosis. See, for example, U.S. Pat. Nos. 6,114,365 and 6,107,305.

The compounds disclosed herein are expected to be useful in the therapy of proliferative or hyperproliferative disorders or diseases such as cancer, autoimmune diseases, viral diseases, fungal diseases, neurodegenerative disorders and cardiovascular disease.

In certain embodiments, tumors may be solid tumors, which are cancer of body tissues other than blood, bone marrow, or the lymphatic system. In other embodiments, tumors may be hematological tumors, such as leukemia and lymphomas. Leukemia is a collective term for malignant diseases characterized by a proliferation of malignantly changed white blood cells. Diseases arising from lymphatic tissue are called lymphomas.

Solid tumors may be selected from: liver cancer, stomach cancer, colon cancer, breast cancer, pancreas cancer, prostate cancer, skin cancer, renal cancer, bone cancer, thyroid cancer, skin cancer, including squamous cell carcinoma, esophagus cancer, kidney cancer, bladder cancer, gall cancer, cervical cancer, ovarian cancer, lung cancer, bronchial, small and non-small-cell lung cancer, gastric, and head and neck cancer.

Hematological tumors may be leukemia, such as Acute Myelogenous Leukemia (AML), Acute Lymphoblastic Leukemia (ALL), Acute Lymphocytic Leukemia, Acute Leukemia, Acute Promyelocytic Leukemia, Chronic Granulocytic Leukemia (CGL), Chronic Leukemia, Chronic Lymphocytic Leukemia (CLL), Chronic Myelogenous Leukemia (CML), Chronic Myelomonocytic Leukemia, Common-type Acute Lymphoblastic Leukemia, Eosinophilic Leukemia, Erythroleukemia, Extranodal Lymphoma, Follicular Lymphoma, Hairy Cell Leukemia, Monocytic Leukemia, Prolymphocytic Leukemia.

Hematological tumors may also be lymphoma, such as B Cell Lymphomas, Burkitt Lymphoma, Cutaneous T Cell Lymphoma, High-Grade Lymphoma, Hodgkin's Lymphoma, Non-Hodgkin's Lymphoma, Low-grade Lymphoma, Lymphoblastic Lymphoma, Mantle Cell Lymphoma, Marginal Zone Lymphoma, Mucosa-Associated Lymphoid Tissue (MALT) Lymphomas, T Cell Lymphomas, peripheral T cell lymphoma, multiple myeloma, Essential Thrombocythemia, Hairy Cell Lymphoma, Extramedullary myeloma, Granulocytic Sarcomae.

Hematological tumors may also be tumors of myeloid lineage, including acute and chronic myelogenous leukemias, myelodysplastic syndrome, and promyelocytic leukaemia.

Tumors may also be of mesenchymal origin, such as fibrosarcoma and rhabdomyosarcoma. Furthermore, tumors may be tumors of the central and peripheral nervous system, such as astrocytoma, neuroblastoma, glioma, and schwannomas; and tumors may be other tumors, such as melanoma, seminoma, teratocarcinoma, osteosarcoma, xenoderoma pigmentosum, keratoctanthoma, thyroid follicular cancer, and Kaposi's sarcoma.

Tumors that are resistant or refractory to treatment with other anti-cancer or anti-proliferative agents may also benefit from treatment with the methods and pharmaceutical compositions of the present invention.

Compounds disclosed herein may also be useful in the chemoprevention of cancer. Chemoprevention is defined as inhibiting the development of invasive cancer by either blocking the initiating mutagenic event or by blocking the progression of pre-malignant cells, such as by blocking growth of the tumor, that have already suffered an insult or inhibiting tumor relapse.

Compounds disclosed herein may also be useful in inhibiting tumor angiogenesis and metastasis.

The compounds of this invention may also be useful in combination (administered together or sequentially) with known anti-cancer treatments such as radiation therapy or with anti-cancer, anti-proliferative, cytostatic or cytotoxic agents. Other anti-cancer and anti-proliferative agents which may be used in combination with the compounds of the present invention include those described herein. In combination treatment, the compounds of the present invention may be further administered with any other anti-cancer and anti-proliferative agent disclosed herein.

If formulated as a fixed dose, such combination products employ the compounds of this invention within the dosage range described herein and the other pharmaceutically active agent or treatment within its approved dosage range. For example, the cdc2 inhibitor olomucine has been found to act synergistically with known cytotoxic agents in inducing apoptosis (J. Cell Sci., 108, 2897 (1995)). Compounds described herein may also be administered sequentially with known anti-cancer or anti-proliferative agents when a combination formulation is inappropriate. The invention is not limited in the sequence of administration; compounds described herein may be administered either prior to or after administration of the known anti-cancer or anti-proliferative agent. For example, the cytotoxic activity of the cyclin-dependent kinase inhibitor flavopiridol is affected by the sequence of administration with anticancer agents (Cancer Research, 57, 3375 (1997)).

Further Aspects of the Invention

Another aspect the invention provides a pharmaceutical package, wherein said package includes a compound of any of the formulae of the present invention. In certain embodiments, the package comprises instructions which indicate that said composition may be used for the treatment of an individual in need thereof, including a human. In certain other embodiments, the pharmaceutical package includes one or more compounds of the present invention formulated together with another pharmaceutical ingredient such as an anti-cancer or anti-proliferative agent. In this case, the compound(s) of the present invention and the other pharmaceutical ingredient may be formulated separately and in individual dosage amounts.

Other pharmaceutical ingredients that may be formulated together or separately with the compounds of the present invention include but are not limited to other anti-cancer and anti-proliferative agents such as described above. In certain still further embodiments, the pharmaceutical package comprises instructions to treat a patient in need of such treatment. In yet another aspect the invention provides a pharmaceutical package for treating an individual suffering from a proliferative disorder or disease, such as a tumor or a cancer, wherein said package includes at least one compound of the present invention. In certain still further embodiments, the pharmaceutical package comprises instructions to treat the disorder.

As used herein the term "pharmaceutical package" or "pharmaceutical pack" refer to any packaging system for storing and dispensing individual doses of medication. Preferably the pharmaceutical package contains sufficient daily dosage units appropriate to the treatment period or in amounts which facilitate the patient's compliance with the regimen. In certain embodiments, the pharmaceutical pack comprises one or more vessels that include the active ingredient, e.g., a compound of the present invention. Such vessel can be a container such as a bottle, vial, syringe, or capsule, or may be a unit dosage form such as a pill. The active ingredient may be provided in the vessel in a pharmaceutically acceptable form or may be provided, for example, as a lyophilized powder. In further embodiments, the pharmaceutical pack may further include a solvent to prepare the active ingredient for administration. In certain embodiments, the active ingredient may be already provided in a delivery device, such as a syringe, or a suitable delivery device may be included in the pack. The pharmaceutical package may comprise pills, liquids, gels, tablets, dragees or the pharmaceutical preparation in any other suitable form. The package may contain any number of daily pharmaceutical dosage units. The package may be of any shape, and the unit dosage forms may be arranged in any pattern, such as circular, triangular, trapezoid, hexagonal or other patterns. One or more of the doses or subunits may be indicated, for example to aid the doctor, pharmacist or patient, by identifying such dose or subunits, such as by employing color-coding, labels, printing, embossing, scorings or patterns. The pharmaceutical package may also comprise instructions for the patient, the doctor, the pharmacist or any other related person.

Some embodiments comprise the administration of more than one active ingredient, including compounds as disclosed herein. Such administration may occur concurrently or sequentially. The active ingredients may be formulated together such that one administration delivers both components. Alternatively the active ingredients may be formulated separately. The pharmaceutical package may comprise the compound of the present invention and the other pharmaceutical ingredient in a single formulation, i.e., they are formulated together, or the compound of the present invention and the other pharmaceutical ingredient in individual formulations, i.e., they are formulated separately. Each formulation may comprise the compound of the present invention and the other pharmaceutical ingredient in individual dosage amounts (in approximately equal or unequal amounts). Administration of the compound of the present invention and the other pharmaceutical ingredient results in a concentration that results in a therapeutically effective amount of the combination.

As used herein, the term "instructions" means a product label and/or documents or other information describing relevant materials or methodologies pertaining to assembly, preparation or use of a kit or packaged pharmaceutical. These materials may include any combination of the following: background information, steps or procedures to follow, list of components, proposed dosages, warnings regarding possible side effects, instructions for administering the drug, technical support, and any other related documents. Instructions can be supplied in printed form, such as a package label or a package insert. Instructions for a packaged pharmaceutical or a pharmaceutical composition can be inserted in a delivery carton or finished package, e.g., as a package insert, and the text of such has been approved by a competent regulatory authority such as the Food and Drug Administration (FDA) of the United States. Alternatively or complementarily, instruction may also be stored in electronic form, e.g., on a computer-readable storage medium such as a computer-readable memory device, a centralized database, magnetic media such as hard disks, floppy disks, and magnetic tape; optical media such as compact discs, CD-ROMs and holographic devices; magneto-optical media such as floptical disks; and hardware devices that are specially configured to store and execute program code, such as application-specific integrated circuits (ASICs), programmable logic devices (PLDs) and ROM (read only memory) and RAM (random access memory) devices. Instructions may comprise a web address of an internet website from which more detailed instructions may be downloaded, or a recorded presentation. Instructions can contain one or multiple documents or future updates.

Thus, in one aspect the invention relates to a pharmaceutical package, including a pharmaceutical composition of the present invention, and instructions which indicate that said pharmaceutical composition may be used for the treatment of an individual in need thereof.

In certain embodiments of such pharmaceutical package, said instructions indicate that said pharmaceutical composition may be used for the treatment of a human.

In certain embodiments of such pharmaceutical package, said instructions indicate that said pharmaceutical composition may be used for the treatment of an individual suffering from a disorder or disease.

In certain embodiments of such pharmaceutical package, said instructions indicate that said pharmaceutical composition may be used for the treatment of a human suffering from a disorder or disease.

In another aspect the invention relates to a method for treating a disorder or disease in an individual, comprising exposing cells included in said a disorder or disease to a compound of the present invention.

In certain embodiments of such method, said compound, or a prodrug thereof, is administered to said individual.

In certain embodiments of such method, said individual is a mammal is selected from: domestic mammal, cat, dog, horse, sheep, cow, rodent, and human.

In certain embodiments of such method, said mammal is a human.

In another aspect the invention relates to a method for inhibiting cell proliferation, comprising contacting a cell with a compound of the present invention.

In another aspect the invention relates to a use of a compound of the present invention, for the preparation of a medicament for the treatment of a disorder or disease.

In another aspect the invention relates to a pharmaceutical composition comprising a compound of the present invention, and a pharmaceutically acceptable carrier, diluent or excipient, for the treatment of a disorder or disease.

In certain embodiments of such a pharmaceutical composition, the pharmaceutical package, method, or use of the present invention, the disorder or disease is a proliferative disorder or disease.

In certain such embodiments, said proliferative disorder or disease is a cancer.

In certain such embodiments, said disorder or disease is an inflammatory disorder or disease.

EXAMPLES

A selection of compounds within the scope of the present invention are listed in Table 1. The compounds in Table 1 were synthesized according to examples 1 to 8 below, and the surprising inhibitory activities in biochemical assays, and anti-proliferative activities in cellular assays of these compounds are shown in Tables 2 and 3, respectively, as determined according to examples 9 to 11.

A: Synthesis of 8-hydroxy-pyrido[2,3-d]pyrimidin-7-one derivatives (Examples 1-8)

Compounds of the invention may be prepared by the synthetic sequence shown in Scheme 1. For example, examples 1-8 show in detail the synthesis steps of Scheme 1. As depicted in Scheme 1,8-oxy pyrido[2,3-d]pyrimidones may be formed in one step from phenylacetic acid hydroxylamide derivatives and 6-chloro-5-formyl-2-methylthiopyrimidine. A skilled artisan will appreciate that other routes of synthesis may be employed as well. In particular, other routes of synthesis may in fact be applied to certain aspects of the present invention. The skilled artisan is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

Scheme 1

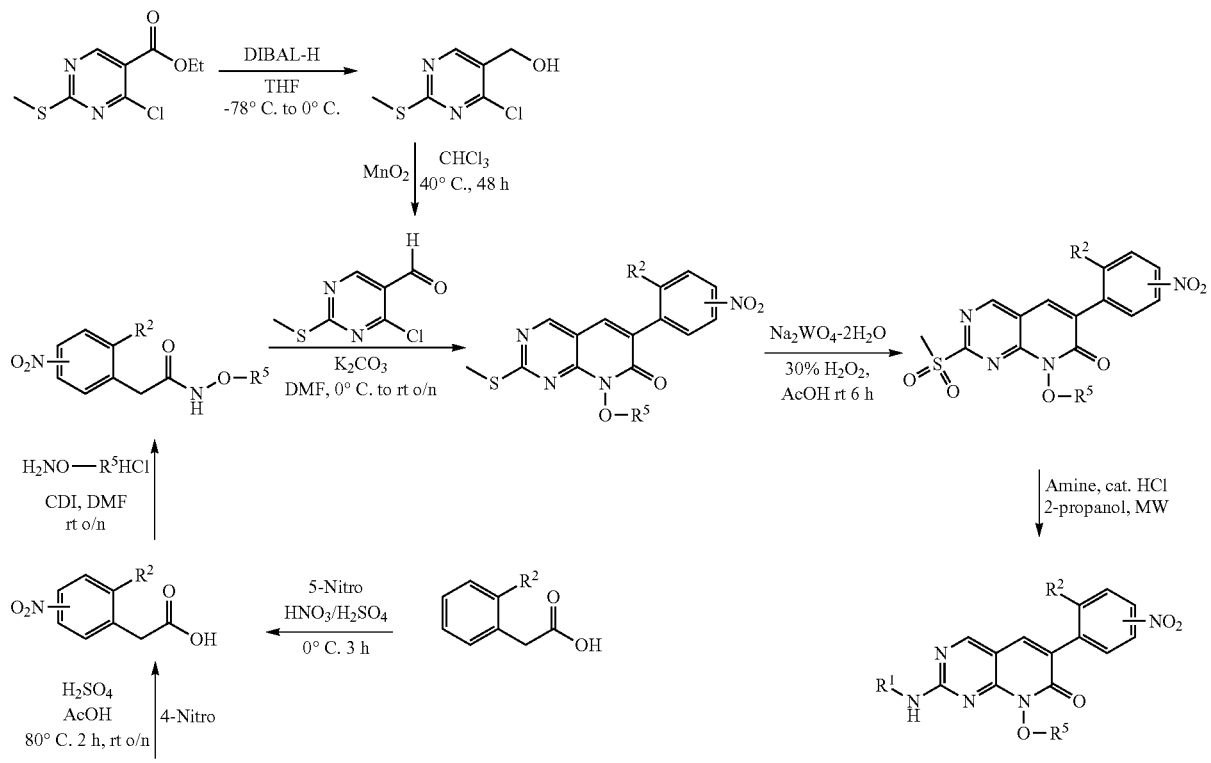

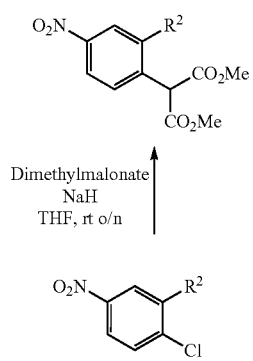
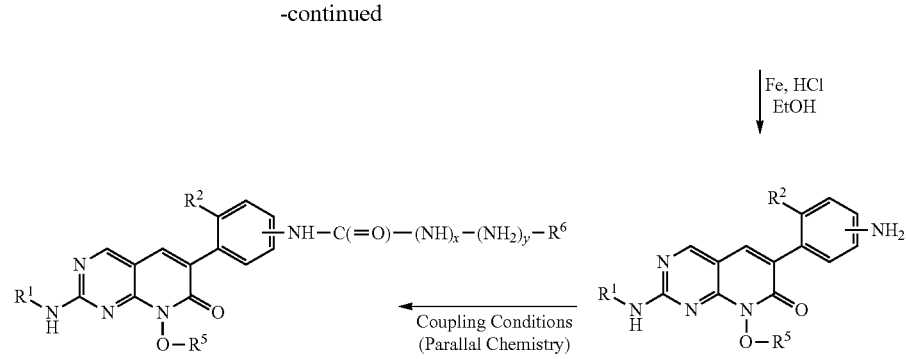

General:

Analytical LCMS:

System 1: Agilent 1200/Agilent 6120 Quadrupole API-ESI-MS/MWD detection at 215, 254, 310 nm Method A: solvent A water with 1% MeCN, 0.1% formic acid, 0.2% 1M aq. ammonium formate; solvent B MeCN with 1% water, 0.1% formic acid, 0.2% aq. ammonium formate; column Agilent ZORBAX SB-Aq Narrow-Bore RR 2.1×50 mm 3.5 μM.

Gradient (0.8 mL/min):

| 0 to 0.5 min | 5% solvent B |
| 0.5 to 6 min | 5 to 95% solvent B |
| 6 to 8 min | 95% solvent B |
| 8.0 to 8.1 min | 100% solvent B |
| 8.1 to 10 min | 100% solvent B |
| 10.0 to 10.1 min | 5% solvent B |
| 10.1 to 12 min | 5% solvent B |

Method B: solvent A water with 1% MeCN, 0.1% formic acid, 0.2% 1M aq. ammonium formate; solvent B MeCN with 1% water, 0.1% formic acid, 0.2% aq. ammonium formate; column Agilent ZORBAX Bonus-RP 4.6×75 mm 3.5 μM.

Gradient (0.8 mL/min):

| 0 to 0.5 min | 5% solvent B |
| 0.5 to 6 min | 5 to 95% solvent B |
| 6 to 8 min | 95% solvent B |
| 8.0 to 8.1 min | 100% solvent B |
| 8.1 to 10 min | 100% solvent B |
| 10.0 to 10.1 min | 5% solvent B |
| 10.1 to 13 min | 5% solvent B |

System 2: Agilent 1100/Micromass ZQ API-ESI-MS/DAD detection 200-800 nm

Method C: solvent A 0.1% aq. formic acid; solvent B MeCN with 0.1% formic acid; column Waters XTerra C18 MS 4.6×50 mm 5 μM.

Gradient (0.8 mL/min):

| 0 to 5 min | 3 to 100% solvent B |
| 5.0 to 5.5 min | 100% solvent B |
| 5.50 to 5.51 min | 3% solvent B |
| 5.51 to 6.1 min | 3% solvent B |

Method D: solvent A 0.1% aq. formic acid; solvent B MeCN with 0.1% formic acid; column Waters XTerra C18 MS 4.6×50 mm 5 μM.

Gradient (0.8 mL/min):

| 0 to 1.5 min | 3% solvent B |
| 1.5 to 8.5 min | 3 to 70% solvent B |
| 8.5 to 8.6 min | 70 to 100% solvent B |
| 8.6 to 10.6 min | 100% solvent B |
| 10.6 to 10.7 min | 3% solvent B |
| 10.7 to 12 min | 3% solvent B |
| 5.0 to 5.5 min | 100% solvent B |

Preparative LCMS System:

Agilent 1100/Agilent 6120 Quadrupole API-ESI-MS/MWD detection at 215, 254, 310 nm Solvent A water; solvent B MeCN; column Phenomenex Axia Gemini C18 Prep 21.2×100 mm 5 μM.

Example 1

4-Chloro-2-(methylthio)pyrimidine-5-carbaldehyde

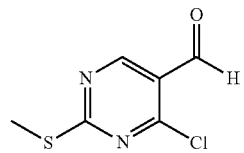

Ethyl 4-chloro-2-(methylthio)pyrimidine-5-carboxylate (67 mmol) was dissolved in THF (900 mL) to give a yellow solution. The mixture was cooled in a −78° C. bath under nitrogen atmosphere (internal temp. about −70° C.). DIBAL-H (1 M in THF; 200 mmol) was added over 45 min. via syringe. The reaction was warmed to −60° C. after the addition, and then allowed to warm slowly to 0° C. overnight. The reaction was quenched by slow addition of saturated aqueous ammonium chloride (200 mL). The mixture was then warmed to room temperature. Ether (400 mL) and saturated aqueous sodium potassium tartrate (200 mL) were added. The mixture was stirred vigorously for 30 min. After separation of the layers, the aqueous layer was extracted with ether and the combined organics washed with brine, dried with sodium sulfate, filtered and concentrated under vacuum to give (4-chloro-2-(methylthio)pyrimidin-5-yl)methanol as a solid (84%).

LCMS (method B) 6.07 min; mass M+H⁺ 191; UV 230, 265, 315 nm.

(4-Chloro-2-(methylthio)pyrimidin-5-yl)methanol (105 mmol) was dissolved in CHCl₃ (500 mL) to give a yellow suspension. Manganese(IV) oxide (546 mmol) was added in 0.5 g portions over 15 min. The mixture was stirred at room temperature for 6 h. Further Manganese(IV) oxide (210 mmol) was added. The mixture was stirred at room temperature for 18 h. Again, manganese(IV) oxide (210 mmol) was added. The mixture was stirred at room temperature for 20 h, then at 40° C. for 4 h, and then overnight at room temperature. The mixture was then stirred at 40° C. for 6 h, allowed to cool to room temperature, filtered though Celite, washed with 400 mL CHCl$_3$ and concentrated under reduced pressure to give 4-chloro-2-(methylthio)pyrimidine-5-carbaldehyde as a solid (72%).

LCMS (method B) 3.72 min; mass M+H$^+$ 193; UV 310 nm.

Example 2

6-(5-Amino-2-chlorophenyl)-2-(2-(dimethylamino)ethylamino)-8-methoxypyrido[2,3-d]pyrimidin-7(8H)-one

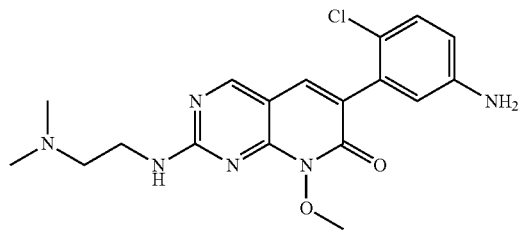

A solution of 2-(2-chlorophenyl)acetic acid (500 mmol) in conc. sulfuric acid (0.7 mL/mmol) was cooled to −10° C. A freshly prepared mixture of fuming nitric acid fuming (809 mmol) and conc. sulfuric acid (1.6 mol) was slowly added at −10° C. The mixture was allowed to warm to 0° C. over 1 h and was stirred for 4 h at 0° C. The solution was slowly poured onto crushed ice/water (3 L). The mixture was stirred vigorously and the formed precipitate was isolated by filtration. The white solid residue was washed with an excess of water (4 L) and dried, giving 2-(2-chloro-5-nitrophenyl)acetic acid (80%).

LCMS (method A) 7.98 min; mass M−H− 214; UV 230, 275, 310 nm.

2-(2-Chloro-5-nitrophenyl)acetic acid (49.9 mmol) and CDI (59.9 mmol) were dissolved in DMF (300 mL) to give a yellow solution. O-Methylhydroxylamine hydrochloride (59.9 mmol) was added. The mixture was stirred at room temperature for 4 h. The reaction mixture was then concentrated under reduced pressure to approximately 50 mL and diluted with 300 mL of ethyl acetate. The organic layer was washed twice with 250 mL of water. The aqueous layer was then saturated with brine and back-extracted with ethyl acetate. The organic layers were combined and subsequently washed with 300 mL of 1 M aq. HCl, 300 mL of sat. aq. NaHCO$_3$, and 300 mL of brine. The organic layer was separated, dried over anhydrous sodium sulfate, filtered and concentrated under vacuum to give 2-(2-chloro-5-nitrophenyl)-N-methoxyacetamide as a solid (69%).

LCMS (method A) 7.98 min; mass M−H− 214; UV 235, 270, 305 nm.

4-Chloro-2-(methylthio)pyrimidine-5-carbaldehyde (90 mmol) and 2-(2-chloro-5-nitrophenyl)-N-methoxyacetamide (98 mmol) were dissolved in DMF (1 L) to give a brown solution. The reaction mixture was cooled to 0° C. Potassium carbonate (197 mmol) was added. The mixture was stirred at 0° C. for 2 h and then allowed to warm to room temperature over night. Potassium carbonate was filtered off and the filtrate was concentrated to approximately 100 mL. The residue was diluted with water (1 L) and filtered. The filter cake was washed with 350 mL of EtOH to give a brown solid that was dried in vacuum. The by-product (Z)-6-(2-chloro-5-nitrophenyl)-2-(methylthio)-7H-pyrano[2,3-d]pyrimidin-7-one O-methyl oxime was separated by reflux of the mixture for 4 h in EtOH and hot filtration of the suspension through a sintered glass funnel. Evaporation of the filtrate and drying gave 6-(2-chloro-5-nitrophenyl)-8-methoxy-2-(methylthio)pyrido[2,3-d]pyrimidin-7(8H)-one as a solid (52%).

LCMS (method A) 5.20 min; mass M+H$^+$ 379; UV 220, 240, 290, 345 nm.

To a colorless suspension of sodium tungstate dihydrate (5.26 mmol) in acetic acid (400 mL) were added 6-(2-chloro-5-nitrophenyl)-8-methoxy-2-(methylthio)pyrido[2,3-d]pyrimidin-7(8H)-one (52.3 mmol) and 30% aq. hydrogen peroxide (160 mmol) at room temperature under an atmosphere of nitrogen. The reaction mixture was stirred at room temperature for 18 h. The mixture was then concentrated to approximately 60 mL under reduced pressure. 500 mL of water were added under rapid stirring. The precipitate was filtered and washed with an excess of water. The remaining solid was dried in vacuum overnight to give 6-(2-chloro-5-nitrophenyl)-8-methoxy-2-(methylsulfonyl)pyrido[2,3-d]pyrimidin-7(8H)-one as a solid (78%).

LCMS (method A) 4.95 min; mass M+H$^+$ 411; UV 220, 275, 325 nm.

6-(2-Chloro-5-nitrophenyl)-8-methoxy-2-(methylsulfonyl)pyrido[2,3-d]pyrimidin-7(8H)-one (4.87 mmol), N,N-dimethylethane-1,2-diamine (11.3 mmol), and conc. aq. hydrochloric acid (2.0 mL) were placed in a microwave vessel and dissolved in 2-propanol (18 mL). The mixture was heated with microwave irradiation in a sealed vessel at 100° C. for 15 min. The reaction mixture was concentrated under reduced pressure and extracted with EtOAc. The organic layer was washed with water and aqueous buffer (aq. KH$_2$PO$_4$ and NaOH. pH 7.0). The aqueous layer was backextracted with EtOAc (4×50 mL). The organic layer was dried over Na$_2$SO$_4$, filtered and concentrated under reduced pressure to give solid 6-(2-chloro-5-nitrophenyl)-2-(2-(dimethylamino)ethylamino)-8-methoxypyrido[2,3-d]pyrimidin-7(8H)-one that was used without furoom temperatureher purification (53%).

LCMS (method A) 4.53 min; mass M+H+ 419; UV 215, 320, 375 nm.

To an solution of 6-(2-chloro-5-nitrophenyl)-2-(2-(dimethylamino)ethylamino)-8-methoxypyrido[2,3-d]pyrimidin-7(8H)-one (73.2 mmol) in EtOH (700 mL) were added conc. aq. hydrochloric acid (170 mL) and iron powder (732 mmol), and the mixture was stirred at 80° C. for 6 h. The mixture was allowed to cool to room temperature and filtered through a pad of Celite. The filtrate was diluted with EtOAc (700 mL) and washed with sat. aq. NaHCO$_3$ (700 mL). The aqueous layer was backextracted with EtOAc (8×300 mL). The organic layers were combined and washed with sat. aq. NaCl (1×700 mL). Drying of the organic layer over Na$_2$SO$_4$, followed by evaporation of the solvent gave crude product that was purified by column chromatography on silica gel (dichloromethane/triethylamine 95:5, followed by dichloromethane/MeOH/triethylamine 90:5:5). The collected fractions were dissolved in dichloromethane and washed with water to remove triethylamine salts. The aqueous layer was backextracted with dichloromethane, the organic layers were combined, dried over Na$_2$SO$_4$, filtered and evaporated to give 6-(5-amino-2-chlorophenyl)-2-(2-(dimethylamino)ethylamino)-8-methoxypyrido[2,3-d]pyrimidin-7(8H)-one as a solid (32%).

LCMS (method B) 4.90 min; mass M+H⁺ 389; UV 225, 295, 345 nm.

Example 3

Representative Preparation of 4-chloro-N-(4-chloro-3-(2-(2-(dimethylamino)ethylamino)-8-methoxy-7-oxo-7,8-dihydropyrido[2,3-d]pyrimidin-6-yl)phenyl)-3-(trifluoromethyl)benzamide

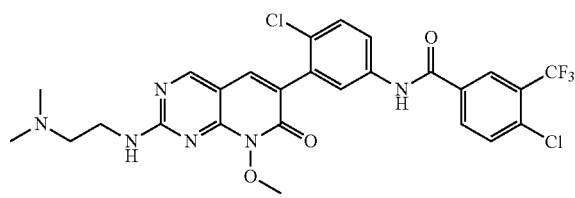

In a 3 ml vial equipped with a small triangular magnetic stirring bar was placed 6-(5-amino-2-chlorophenyl)-2-(2-(dimethylamino)ethylamino)-8-methoxypyrido[2,3-d]pyrimidin -7(8H)-one (348 µmol). Triethylamine (344 µmol) was added, followed by aliquots of DMF stock solutions of HATU (320 µmol) and 4-chloro-3-(trifluoromethyl)benzoic acid (129 µmol), and the mixture was stirred at room temperature over night. The solution was transferred to maximum recovery HPLC vials and purified by prep. HPLC-MS. The collected fractions were transferred to centrifuge vials and lyophilized, giving 4-chloro-N-(4-chloro-3-(2-(2-(dimethylamino)ethylamino)-8-methoxy-7-oxo-7,8-dihydropyrido[2,3-d]pyrimidin-6-yl)phenyl) -3-(trifluoromethyl)benzamide as a solid (70%).

LCMS (method B) 6.81 min; mass M+H⁺ 595; UV 240, 290, 340 nm.

Example 4

Representative Preparation of 1-(4-chloro-3-(2-(2-(dimethylamino)ethylamino)-8-methoxy-7-oxo-7,8-dihydropyrido[2,3-d]pyrimidin-6-yl)phenyl)-3-(3-chloro-4-methoxyphenyl)urea

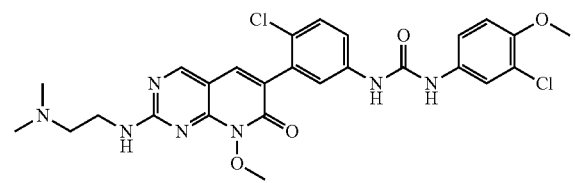

In a 3 ml vial equipped with a small triangular magnetic stirring bar was placed 6-(5-amino-2-chlorophenyl)-2-(2-(dimethylamino)ethylamino)-8-methoxypyrido[2,3-d]pyrimidin -7(8H)-one (165 µmol). A solution of 2-chloro-4-isocyanato-1-methoxybenzene in THF (2 mL, 129 mmol) was added, and the mixture was stirred at room temperature over night. The solvent was allowed to evaporate over night, and the remaining solid was dissolved in DMSO, transferred to maximum recovery HPLC vials and purified by prep. HPLC-MS. The collected fractions were transferred to centrifuge vials and lyophilized, giving 1-(4-chloro-3-(2-(2-(dimethylamino)ethylamino)-8-methoxy-7-oxo-7,8-dihydropyrido[2,3-d]pyrimidin-6-yl)phenyl) -3-(3-chloro-4-methoxyphenyl) urea as a solid (56%).

LCMS (method B) 6.56 min; mass M+H⁺ 572; UV 230, 260, 345 nm.

Example 5

6-(4-Amino-2-chlorophenyl)-2-(2-(dimethylamino)ethylamino)-8-methoxypyrido[2,3-d]pyrimidin-7(8H)-one

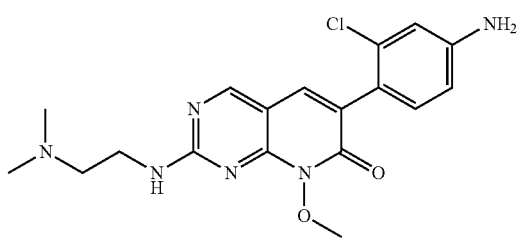

NaH (288 mmol) was suspended in DMF (370 mL) at 0° C. under an atmosphere of nitrogen. Dimethyl malonate (261 mmol) in DMF (30 mL) was added dropwise over a period of 20 min. at 0° C. and stirring was continued at 0° C. for 30 min. Then 1,2-dichloro-4-nitrobenzene (130 mmol) in DMF (35 mL) was added dropwise at 0° C. over a period of 20 min. The mixture was stirred at 70° C. for 15 h. The reaction mixture was cooled to room temperature and quenched with NH4Cl. The solution was successively washed with EtOAc (1×100 mL, 1×250 mL) and water (2×150 mL). To facilitate separation of the layers, sat. aq. NaCl (20 mL) was added. The organic layer was separated and washed with sat. aq. NaCl (2×100 mL). The aqueous layer was backextracted with EtOAc (2×50 mL). The organic layer was dried over Na2SO4, filtered and concentrated under reduced pressure. The crude material was recrystallized from EtOH to give dimethyl 2-(2-chloro-4-nitrophenyl)malonate as a solid (74%).

LCMS (method C) 4.08 min; mass M+H+ 288; UV 210, 270 nm.

Dimethyl 2-(2-chloro-4-nitrophenyl)malonate (96 mmol) was suspended in acetic acid (175 mL). Conc. sulfuric acid (3.5 mL) was added and the mixture was stirred at 80° C. over night. Water (30 mL) was added and the mixture was stirred at 100° C. for 2 h. after which conc. sulfuric acid (1 mL) was added. The mixture was stirred at room temperature over night. The formed precipitate was filtered off and washed with water. The remaining solid was dried under reduced pressure to give 2-(2-chloro-4-nitrophenyl)acetic acid as a solid (80%).

LCMS (method C) 5.87 min; mass (M−H)2−429; UV 210, 280 nm.

2-(2-Chloro-4-nitrophenyl)acetic acid (67.2 mmol) was dissolved in DMF (500 mL) to give a colorless solution. CDI (87 mmol) was added in one portion. The mixture was stirred at room temperature until bubbling of the solution ceased. Methoxylamine hydrochloride (87 mmol) was added poroom temperatureion wise, and the resulting mixture was stirred at room temperature over night. The resulting suspension was concentrated under reduced pressure to 100 mL and then diluted with EtOAc (1200 mL). The resulting solution was washed with water (2×700 mL) and the aqueous layer was extracted back with EtOAc (2×600 mL). The organic layers were combined and washed with sat. aq. NaHCO₃ (1×1200 mL) and sat. aq. NaCl (1×1200 mL). The organic layer was dried over Na₂SO₄, filtered and concentrated under reduced pressure to give 2-(2-chloro-4-nitrophenyl)-N-methoxyacetamide as a solid (85%).

LCMS (method C) 3.03 min; mass M+H$^+$ 245; UV 210, 270 nm.

2-(2-Chloro-4-nitrophenyl)-N-methoxyacetamide (49.3 mmol) and 4-chloro-2-(methylthio)pyrimidine-5-carbaldehyde (41.2 mmol) were dissolved in DMF (600 mL). The solution was cooled to 0° C., and K2CO3 (91 mmol) was added in one poroom temperatureion. The mixture was stirred at 0° C. for 2 h and then at room temperature for 48 h. The reaction mixture was filtered and the filtrate was concentrated under reduced pressure to 60 mL. Water (600 mL) was added. The precipitate was filtered, washed twice with EtOH and dried. The by-product (Z) -6-(2-chloro-4-nitrophenyl)-2-(methylthio)-7H-pyrano[2,3-d]pyrimidin-7-one O-methyl oxime was separated by reflux of the mixture for 4 h in EtOH and hot filtration of the suspension through a sintered glass funnel. Evaporation of the filtrate and drying gave 6-(2-chloro-4-nitrophenyl)-8-methoxy-2-(methylthio)pyrido[2,3-d]pyrimidin-7(8H)-one as a solid (63%).

LCMS (method A) 5.22 min; mass M+H+ 379; UV 215, 255, 340 nm.

Sodium tungstate dihydrate (0.633 mmol) was suspended in conc. acetic acid (55 mL). 6-(2-chloro-4-nitrophenyl)-8-methoxy-2-(methylthio)pyrido[2,3-d]pyrimidin-7(8H)-one (6.33 mmol) was added, followed by 30% aq. hydrogen peroxide (2 mL). The mixture was stirred at room temperature over night. The reaction mixture was concentrated under reduced pressure to 5 mL. The solution was diluted with water (100 mL) and the precipitate isolated by filtration, washed with water and dried in vacuum to give 6-(2-chloro-4-nitrophenyl)-8-methoxy-2-(methylsulfonyl)pyrido[2,3-d]pyrimidin-7(8H)-one as a solid (77%).

LCMS (method A) 4.97 min; mass M+H+ 411; UV 215, 265, 320 nm.

To a suspension of 6-(2-chloro-4-nitrophenyl)-8-methoxy-2-(methylsulfonyl)pyrido[2,3-d]pyrimidin-7(8H)-one (4.74 mmol) in 2-propanol (15 mL) was added N,N-dimethylaminoethylamine (47.4 mmol), followed by conc. hydrochloric acid (300 µL). The mixture was heated with microwave irradiation in a sealed vessel at 100° C. for 15 min. Dichloromethane was added to the reaction mixture until solution. The solution was then concentrated under reduced pressure to give 6-(2-chloro-4-nitrophenyl)-2-(2-(dimethylamino)ethylamino)-8-methoxypyrido[2,3-d]pyrimidin-7(8H)-one as a solid (95%).

LCMS (method A) 4.47 min; mass M+H+ 419; UV 245, 340 nm.

To a solution of 6-(2-chloro-4-nitrophenyl)-2-(2-(dimethylamino)ethylamino)-8-methoxypyrido[2,3-d]pyrimidin-7(8H)-one (8.36 mmol) in EtOH (300 mL) and conc. hydrochloric acid (20 mL), iron powder (91 mmol) was added and the mixture was stirred at 80° C. for 2 h. The mixture was then allowed to cool to room temperature and filtered through a pad of Celite. The filtrate was diluted with EtOAc (300 mL) and washed with sat. aq. NaHCO₃ (300 mL). The aqueous layer was backextracted with EtOAc (8×150 mL). The organic layers were combined and washed with brine (1×300 mL). Drying of the organic layer over Na₂SO₄, filtration and evaporation of the solvent gave 6-(4-amino-2-chlorophenyl)-2-(2-(dimethylamino)ethylamino)-8-methoxypyrido[2,3-d]pyrimidin-7(8H)-one as a solid (43%).

LCMS (method B) 5.09 min; mass M+H$^+$ 389; UV 220, 245, 290, 345 nm.

Example 6

Representative Preparation of 4-chloro-N-(3-chloro-4-(2-(2-(dimethylamino)ethylamino)-8-methoxy-7-oxo-7,8-dihydropyrido[2,3-d]pyrimidin-6-yl)phenyl)-3-(trifluoromethyl)benzamide

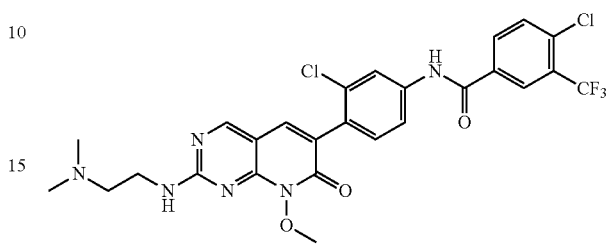

In a 6 ml maximum recovery HPLC vial equipped with a small triangular magnetic stirring bar was placed 6-(5-amino-2-chlorophenyl)-2-(2-(dimethylamino)ethylamino)-8-methoxypyrido[2,3-d]pyrimidin-7(8H)-one (347 µmol). Triethylamine (344 µmol) was added, followed by aliquots of DMF stock solutions of HATU (320 µmol) and 4-chloro-3-(trifluoromethyl)benzoic acid (129 µmol), and the mixture was stirred at room temperature over night. The solutions were purified by prep. HPLC-MS. The collected fractions were transferred to centrifuge vials and lyophilized, giving 4-chloro-N-(3-chloro-4-(2-(2-(dimethylamino)ethylamino)-8-methoxy-7-oxo-7,8-dihydropyrido[2,3-d]pyrimidin-6-yl)phenyl) -3-(trifluoromethypbenzamide as a solid (85%).

LCMS (method B) 6.86 min; mass M+H$^+$ 595; UV 235, 300, 350 nm.

Example 7

2,6-Dichloro-N-(4-chloro-3-(2-(2-(dimethylamino)ethylamino)-8-methoxy-7-oxo-7,8-dihydropyrido[2,3-d]pyrimidin-6-yl)phenyl)-isonicotinamide

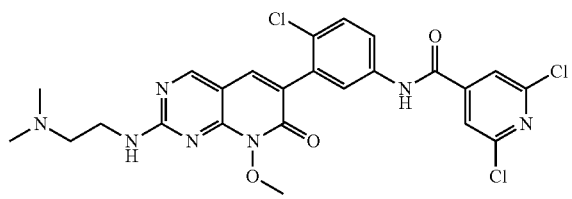

To a solution of 2,6-dichloroisonicotinic acid (0.37 g) in 10 ml THF was added diisopropylethylamine (0.449 ml) followed by HATU (0.733 g). After 10 min 1 ml DCM and 2 ml DMF were added. Then 6-(5-amino-2-chlorophenyl)-2-(2-(dimethylamino)ethylamino)-8-methoxypyrido[2,3-d]pyrimidin-7(8H)-one (0.5 g) was added as solution in THF (10 ml) with 1 ml DCM and 2 ml DMF. The reaction was stirred at r.t. for 1 h. The reaction mixture was diluted with 10 ml DCM, treated with 5 ml methanol and evaporated on 15 g alox (neutral).

The crude mixture was chromatographed on silica using a flashmaster system staroom temperatureing with 90/10/1 (DCM/MeOH/TEA) going to 80/20/1 (DCM/MeOH/TEA) to give 1.09 g crude product.

50 mg of crude product were purified on prep HPLC-MS in MeCN/water (0.1% formic acid) to give 25 mg purified final compound.

Example 8

2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-diethylamino-isonicotinamide

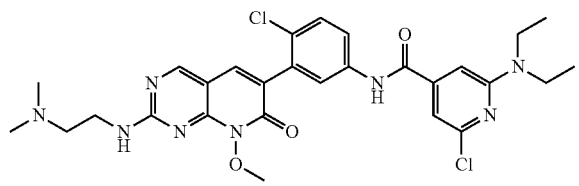

40 mg 2,6-dichloro-N-(4-chloro-3-(2-(2-(dimethylamino)ethylamino)-8-methoxy-7-oxo-7,8-dihydropyrido[2,3-d]pyrimidin-6-yl)phenyl)-isonicotinamide and 50 µl diethylamine were dissolved in 5 ml DMSO and heated at 100° C. in the microwave for 10 min. Addition of further diethylamine and heating in the microwave was repeated multiple times until the reaction was complete. The reaction mixture was purified on HPLC-MS in MeCN/water (1% formic acid) to yield 23 mg.

B: Biological Activity Assays (Examples 9-12)

The biological activity and utility of the compounds of the invention can be demonstrated by one or more assays including those described in more detail below.

Example 9

Determination of $IC_{50}$ Values for Inhibition of Kinase Activity

The in vitro inhibitory activity against protein kinases of compounds of the present invention can be characterized by determining their $IC_{50}$ values.

a) C-Raf (MAPH Assay).

| | |
|---|---|
| Kinase: | C-Raf Raf-1 (truncated), active (Upstate; cat. no. 14-352) |
| Reaction Volume: | 40 µl |
| Reaction Time: | 60 min |
| Reaction Temperature: | room temperature |
| Assay Plate: | 96 well U bottom plate (Greiner, 650161) |
| MultiScreen-PH Plate: | 96 well MAPH Filter Plates (Millipore, MAPHNOB50) |
| Filter Washing Solution: | 0.75% $H_3PO_4$ |
| Scintillation Liquid: | Supermix Liquid Scintillator (PerkinElmer, 1200-439) |
| Controls: | |
| Negative Control (C−): | 100 mM EDTA, no inhibitor |
| Positive Control (C+): | no inhibitor |
| Reaction Buffer (final concentration): | |

20 mM Tris, pH 7.5
2 mM $MnCl_2$
1 mM DTT
0.01% Tween20
Final Assay Concentrations:

| | |
|---|---|
| Kinase: | Use kinase conc. yielding 10% ATP turnover as determined in titration experiment. |
| ATP: | 5.78 µM |
| Adenosine 5′-[γ-$^{33}$P]triphosphate: | 12.5 µCi/ml (Amersham Biosciences, BF1000) |
| Substrate: | Myelin Basic Protein 57.8 µM (Invitrogen, 13228-010) |

Pipetting Sequence:
1) Add 10 µl 4-fold concentrated substrate+4-fold concentrated ATP in 3-fold concentrated reaction buffer to each well of assay plate
2) Add 10 µl 4-fold concentrated inhibitor in 4% DMSO in $H_2O$ to each well except to C− and C+ wells (starting point: final inhibitor concentration 10 µM; $IC_{50}$ determination based on dilution series)
3) Add 10 µl 4% DMSO in $H_2O$ to C− and C+ wells
4) Add 10 µl 500 mM EDTA in $H_2O$ to C− wells
5) Add 10 µl 50 µCi/ml adenosine 5′[γ-$^{33}$P]triphosphate in $H_2O$ to each well
6) Add 10 µl 4-fold concentrated kinase in Reaction Buffer to each well
7) Incubate 1 hr at room temperature
8) Add 10 µl 50 mM EDTA in $H_2O$ to each well except to C— wells
9) Prepare MAPH plates by adding 200 µl 0.75% $H_3PO_4$ to each well
10) Exhaust 0.75% $H_3PO_4$ using Millipore vacuum station
11) Add 60 µl 0.75% $H_3PO_4$ to each well of MAPH filter plate
12) Transfer 30 µl sample per well from assay plate to corresponding well of MAPH filter plate
13) Incubate 30 min at room temperature
14) Wash each well of MAPH filter plates 3× with 200 µl 0.75% $H_3PO_4$ using Millipore vacuum station
15) Add 20 µl scintillation liquid to each well of MAPH filter plate
16) Seal MAPH filter plate
17) Store MAPH filter plate 30 min in darkness
18) Quantify radioactivity using scintillation counter (MicroBeta, Perkin-Elmer)

b) C-Raf (IMAP Assay)

| | |
|---|---|
| Kinase: | C-Raf Raf-1 (truncated), active (Upstate; cat. no. 14-352) |
| IMAP Assay: | |
| Reaction Volume: | 8.0108 µl |
| Reaction Time: | 60 min |
| Reaction Temperature: | room temperature |
| IMAP Incubation Time: | 60 min |
| Assay Plate: | 384 well U bottom, PP, black, low volume (Corning, 3676) |
| Compound Plate: | 384 well U bottom, PS (Falcon, 3995) |
| IMAP Binding Buffer A: | Molecular Devices, R7282 |
| IMAP Binding Buffer B: | Molecular Devices, R7283 |
| IMAP Binding Reagent: | Molecular Devices, R7207 |
| Controls: | |
| Negative Control (C−): | no kinase, no inhibitor |
| Positive Control (C+): | no inhibitor |
| Reaction buffer: | 20 mM Hepes, pH 7.5 |
| | 1 mM DTT |
| | 10 mM $MnCl_2$ |
| | 0.01% Brij35 |
| Final Assay Concentrations: | |
| Kinase: | Kinase conc. yielding 50% substrate turnover as determined in titration experiment c-Raf (Upstate 14-352) |

-continued

| | |
|---|---|
| ATP: | 4.87 μM |
| Substrate: | 5Fl-SGQLIDSMANSFV-NH$_2$ 400 nM (jpt Peptide Technologies GmbH, Berlin, Germany) |
| IMAP Binding Solution: | 75% IMAP Binding Buffer A 25% IMAP Binding Buffer B IMAP Binding Reagent 1:800 |

Pipetting Sequence:
1) Add 6 μl 1.33-fold concentrated substrate+1.33-fold concentrated ATP in 1-fold concentrated reaction buffer to each well of assay plate
2) Add 10.8 nl 740-fold concentrated inhibitor in 100% DMSO to each well except to C− and C+ wells using pintool (CyBio, Jena, Germany) (starting point: final inhibitor concentration 10 μM; IC$_{50}$ determination based on dilution series)
3) Add 10.8 nl 100% DMSO to C− and C+ wells using pintool
4) Add 2 μl reaction buffer to C− wells
5) Add 2 μl 4-fold concentrated kinase in reaction buffer to each well except C− wells
6) Incubate according to reaction time at room temperature
7) Add 15 μl IMAP binding solution to each well
8) Incubate according to IMAP incubation time at room temperature
9) Measure fluorescence polarization (Analyst GT, Molecular Devices)

c) B-Raf

| | |
|---|---|
| Kinase: | B-Raf delta1-415 (e.g., Upstate Cat. No. 14-530) |
| Reaction Volume: | 40 μl |
| Reaction Time: | 60 min |
| Reaction Temperature: | room temperature |
| Assay Plate: | 96 well U bottom plate (Greiner, 650161) |
| MultiScreen-PH Plate: | 96 well MAPH Filter Plates (Millipore, MAPHNOB50) |
| Filter Washing Solution: | 0.75% H$_3$PO$_4$ |
| Szintilation Liquid: | Supermix Liquid Szintillator (PerkinElmer, 1200-439) |
| Controls: | |
| Negative Control (C−): | 100 mM EDTA, no Inhibitor |
| Positive Control (C+): | no Inhibitor |
| Reaction Buffer: | 20 mM Mops, pH 7.0 10 mM MgCl$_2$ 0.4 mM MnCl$_2$ 100 mM NaCl 1 mM DTT 0.01% NP40 |
| Final Assay Concentrations: | |
| Kinase: | Kinase conc. yielding 50% substrate turnover as determined in titration experiment. |
| ATP: | 27.15 μM |
| Adenosine 5'-[γ-$^{33}$P]triphosphate: | 12.5 μCi/ml (Amersham Biosciences, BF1000) |
| Substrate: | MEK1 inactive 2 μM (Upstate 14-420) |

Pipetting Sequence:
1) Add 10 μl 4-fold concentrated substrate in 3-fold concentrated reaction buffer to each well of assay plate
2) Add 10 μl 4-fold concentrated inhibitor in 4% DMSO in H$_2$O to each well except to C− and C+ wells (starting point: final inhibitor concentration 10 μM; IC$_{50}$ determination based on dilution series)
3) Add 10 μl 4% DMSO in H$_2$O to C− and C+ wells
4) Add 10 μl 500 mM EDTA in H$_2$O to C− wells
5) Add 10 μl 50 μCi/ml adenosine 5'[γ-$^{33}$P]-triphosphate in H$_2$O+4-fold cold ATP to each well
6) Add 10 μl 4-fold concentrated kinase in reaction buffer to each well
7) Incubate 1 hr at room temperature
8) Add 10 μl 50 mM EDTA in H$_2$O to each well except to C− wells
9) Prepare MAPH plates by adding 200 μl 0.75% H$_3$PO$_4$ to each well
10) Exhaust 0.75% H$_3$PO$_4$ using Millipore vacuum station
11) Add 60 μl 0.75% H$_3$PO$_4$ to each well of MAPH filter plate
12) Transfer 30 μl sample per well from assay plate to corresponding well of MAPH filter plate
13) Incubate 30 min at room temperature
14) Wash each well of MAPH filter plates 3× with 200 μl 0.75% H$_3$PO$_4$ using Millipore vacuum station
15) Add 20 μl scintillation liquid to each well of MAPH filter plate
16) Seal MAPH filter plate
17) Store MAPH filter plate 30 min in darkness
18) Quantify radioactivity using scintillation counter (MicroBeta, Perkin-Elmer)

d) B-Raf/B-Raf (V600E) (SelectScreen™ Assay)

Selected compound of the present invention were tested in the Select Screen™ Kinase Profiling Service (Invitrogen Corporation, Madison, Wis. 53719, USA) against B-Raf and the B-Raf (V600E) ["V599E" in terminology used by Invitrogen], under conditions of non-disclosure, non-dissemination and non-use.

In brief, compounds 11 and 39 (see Table 1) were tested at Invitrogen against B-Raf and the B-Raf (V600E), either with or without preincubation of kinase/test compound for 5 hours. Table 9(d) shows the IC$_{50}$ values that were observed in these experiments. Surprisingly, the compounds of the present invention inhibit the B-Raf (V600E) mutant more strongly than wild-type B-Raf. Furthermore, a much lower IC$_{50}$ value was observed after 5 hours of preincubation, suggesting that the compounds of the present invention bind preferentially to a conformational variant of the B-Raf kinases that is slowly formed in an equilibrium reaction.

TABLE 9(d)

| | IC$_{50}$ [nM] B-Raf | | IC$_{50}$ [nM] B-Raf (V600E) | |
|---|---|---|---|---|
| Compound | w/o preincub.. | 5 h preincub. | w/o preincub. | 5 h preincub. |
| 11 | <250 | <250 | <100 | <100 |
| 39 | <10 | <10 | <5 | <5 | e) Other Kinases

Compounds of the present invention can be shown to be inhibitors of other kinases, including p38 and KDR, as well by using standard kinase inhibition assays.

Compounds of the present invention are tested for inhibitory activity against other kinases, including tyrosine kinases and serine-threonine kinases, using assays known in the art, such as those described in WO 06/002119. Selectivity of specific compounds or compound-classes between various kinase enzymes or kinase families are investigated by comparison of the $IC_{50}$ values obtained from such assays.

For example, selected compound of the present invention were tested in a standard selectivity panel including c-Raf, p38, and 22 other kinases (Proteros biostructures GmbH, Martinsried/Munich, Germany), under conditions of non-disclosure, non-dissemination and non-use.

In brief, selected compounds of the present invention were tested at 1 mM in triplicates against c-Raf, p38 as well as against Ab1, Akt1, Aur A, c-Kit, c-Raf, Cdk1/CycB, Chk1, FGFR3, Flt3, Fyn, IGF1-R, INSR, Lyn, MAPK-ERK1, PAK-4, PKCalpha, Plk1, Ret, ROCK2, RSK 1, c-Src, TIE2, and VEGF-R2. All test compounds inhibited c-Raf and p38 from about 70% to about 100%. c-Kit was inhibited by almost all compounds as well, though with lower inhibition values (from about 50% to about 90%. Compounds with $R^4$=—NH—C(=O)—$R^6$ exhibited strong to medium inhibitory activity against Fyn, Lyn, Src, and medium inhibitory activity against Abl and Ret. Compounds with $R^4$=—NH—C(=O)—NH—$R^6$ exhibited medium inhibitory activity against Lyn, and low inhibitory activity against all other kinases. About 13 kinases were inhibited by less than about 30% in every case.

Example 10

Improved Affinity of Compounds of the Invention to B-Raf

Surprisingly, we find that compounds of the invention show improved binding affinity to B-Raf protein in an in-vitro assay, even compared to structurally-related compounds that do not have a substituent $R^3$ or $R^4$ in Formula (I) being: —NH—C(=O)—(NH)$_x$—(CH$_2$)$_y$—$R^6$ (wherein x any y are independently selected from 0 and 1; and $R^6$ is selected from substituted or unsubstituted aryl, and substituted or unsubstituted heteroaryl). Such structurally related compounds without such a substitution are described in earlier filed patent applications: EP 06122344.2, PCT/US2007/013299 and PCTAB2007/054209.

Binding affinity ($K_i$) of compounds of the invention is estimated using a modified FRET-, based (Fluorescence resonance energy transfer) HTRF (homogeneous time resolved fluorescence) competition assay. Briefly, 7 nM of an N-terminal fusion of GST and the kinase domain of B-Raf ("GST-B-Raf delta1-415") is incubated for 120 min with 15 nM of Europium-labeled anti-GST antibody (61GSTKLB; CisBio) to form an antibody/kinase complex labeled with the Europium donor moiety. After addition of 1 mM "Compound X" labeled with Cy5 as receptor moiety, various concentrations of test compounds of the invention are added, and the decay of the FRET signal brought about by competition of the Compound X/B-Raf interaction by test compound is recorded using the HTRF detection-mode of an Analyst® GT Multimode Reader (Molecular Devices), with excitation at 340 nm and detection at 665 nm wavelengths.

The GST-B-Raf delta1-415 fusion protein is expressed and purified using standard procedures from an appropriately constructed protein expression eukaryotic vector.

Compound X is synthesized by standard procedures, and is labeled with Cy5 briefly as described below.

Compound X

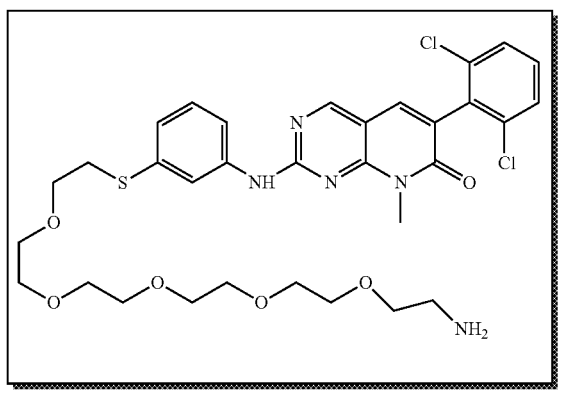

Approximately 400 nmol of Compound X in DMSO (50 μl) is added to 250-350 nmol Cy5 mono-reactive dye pack (PA25001; Amersham Biosciences) in the presence of a molar-equivalent (to Cy5) of DIEA (di-isopropyl-ethylamine; Hünig Base), and is incubated overnight at room temperature in the dark. The resulting Cy5-labeled Compound X is purified by HPLC with a reverse phase column (C18, 5 μm) using a gradient of aqueous TFA and MeCN (acentonitrile), and its purity is determined by mass spectrometry.

The test-compound concentration- and time-dependent decrease in FRET signal resulting from HTFR of the Compound X/B-Raf complex is used to estimate the $K_{obs}$ for each concentration of test compound (Excel Fit, IDBS using the model $y=y^\infty+y^0*\exp(-K_{obs})t$), and a subsequent plot of the $K_{obs}$ values against test-compound concentration enables estimated of $K_{on}$ and $K_{off}$ from linear regression of such data using the model $K_{obs}=K_{on}$ [test-compound]+$K_{off}$. $K_i$ is then determined for each test compound of the invention as $K_i=K_{on}/K_{off}$.

Using this methodology (or analogous other methodologies to determine affinity, such as fluorescence cross-correlation spectroscopy), compounds of the invention are found to generally show improved binding affinity to B-Raf compared to structurally-related compounds that do not have a substitution at $R^3$ or $R^4$ of Formula (I) being: —NH—C(=O)—(NH)$_x$—(CH$_2$)$_y$—$R^6$ (wherein x any y are independently selected from 0 and 1; and $R^6$ is selected from substituted or unsubstituted aryl, and substituted or unsubstituted heteroaryl). For example, compounds of the invention generally show $K_i$ values below 100 nM (such as between 20 and 50 nM) and the structurally-related compounds generally show $K_i$ values of greater than 100 nM (such as 150 to 500 nM).

Example 11

In Vitro Anti-Proliferative Activity of Compounds of the Present Invention Against Proliferation of Cancer Cell Lines Carrying BRAF V600E Mutations We observed the surprising finding that compounds of the invention were useful in inhibiting proliferation of HT-29 tumor cells (see Table 3).

Cells were exposed to the test compounds at various concentrations appropriate to determine an $IC_{50}$, for 72 hours, and cell proliferation was measured using the SRB assay according to Shekan et al (J Natl Cancer Inst (1990) 82, 1107-112) in order to estimate the $IC_{50}$ values shown in Table 3.

Briefly, cells were plated in 96 well dishes 24 hours prior to compound addition at the densities specified in Table 11.1.

TABLE 11.1

| ATCC Name | ATCC Order No. | BRAF Status | Cells/well |
|---|---|---|---|
| A-375 | CRL-1619 | V600E | 3500 |
| SK-MEL-28 | HTB-72 | V600E | 9000 |
| HT-29 | HTB-38 | V600E | 9000 |
| A-431 | CRL-1555 | wildtype | 9000 |
| PC-3 | CRL-1435 | wildtype | 4000 |
| IMR-90 | CCL-186 | wildtype | 8000 |

The assay was terminated with the addition of ice cold 10% TCA after growth medium has been removed and the plates were incubated over night at 4° C. The plates were then washed 5 times with water and 100 µl of a Sulforhodamine B solution (4%) was added to each well. The plates were then incubated for 10 minutes at room temperature before removal of unbound dye by washing with 1% acetic acid. The bound dye was solubilized with 10 mM Trizma base and the absorbance read at OD520.

Inhibitory activity of the compounds was calculated as % inhibition of cell proliferation compared to cells treated with the solvent (DMSO). Table 3 represents the $IC_{50}$ values for inhibition of cell proliferation for certain compounds of the invention showing that the compounds demonstrated a clear and pronounced anti-proliferative activity specifically towards cancer cell lines carrying the BRAF V600E mutation.

Example 12

Activity of Compounds in Xenograft Tumor Models

With this assay we demonstrate the activity of compounds of the present invention against tumor cells in an in-vivo xenograft model.

Methods:
Compound Preparation

Compounds of the present invention (see Table 1) are prepared for i.p. administration in a biocompatible vehicle (e.g. in 10% DMA/50% PEG300/water; or in 5% Cremophor EL/5% ethanol/90% saline). All preparations are made freshly and injection volumes are adjusted to body weight (resulting in compound dosages of, for example, between 40 and 80 mg/kg mouse).

Mice/Husbandry.

Mice are obtained from Charles River Laboratory (CRL), housed in static microisolators, and provided ad libitum with water and an irradiated standard rodent diet (Purina Pico-Lab Rodent Diet 20).

Standard Protocol.
Experiments in Athymic mice.

Athymic nu/nu female mice (6-8 weeks old) from CRL are allowed to acclimate for at least 4 days. Human HT-29 cells (ATCC) colon carcinoma cell line are cultured in McCoy's medium (ATCC) supplied with 10% FCS and 1% Pen/Strep. The 2nd passage of cells with approximately 80% confluence is used in the study. Briefly, on Day 0, mice are inoculated with 0.1 ml (total $5 \times 10^6$ cells) of HT-29 cell suspension ($50 \times 10^6$ cells/ml in McCoy's medium without supplements mixed 1:1 with Matrigel) by a subcutaneous injection into the lower right flank under light anesthesia. When the average tumor weights reaches above 100 mg, animals with an appropriate tumor size are selected and are randomly divided into treatment groups (10 animals each).

Tumor growth and body weight are monitored and recorded twice a week. Tumors are measured by determining the length and width of the tumor with a digital caliper. Tumor weight is estimated using the following formula: Tumor Weight (mg)=$(w^2 \times l)/2$ where w=width and l=length in mm of the tumor.

Tumor Growth Inhibition (TGI) % is calculated as follows: % TGI=$100(1-T/C)$ where T is the mean tumor size of a compound treated group on a given day, and C is the mean tumor size of the vehicle control group on the same day.

Toxic deaths are defined as deaths caused by compound treatment and not by advanced disease state. A death is considered toxic if the animal dies within 1 week after the final compound treatment and the tumor size has not reached 1000 mg non-tumor related deaths after this point are recorded, but not considered toxic deaths.

One group is treated with vehicle only (e.g. 10% DMA/50% PEG300/40% ddwater, po), and three groups of mice per compound and treatment schedule are treated with the respective compound in increasing amounts (e.g. with 40, 60 and 80 mg/kg doses dosed for five or ten days).

Mice are sacrificed when their tumors reach the 1000 mm³ endpoint volume. Treatment efficacy is determined as Log Cell Kill (LCK). LCK is a calculation that determines the percentage of tumor cells that are presumably killed after the initiation of treatment and can be used as a quantitative measure of efficacy: LCK=$(T-C)/(3.32)(Td)$ where T=is the mean time required for the treatment group of mice to reach 1000 mg in size, C=the mean time for the control group tumors to reach 1000 mg in size, Td=is the Tumor Doubling time estimated from the linear regression analysis from a semi-log growth plot of the control group tumors during exponential growth and 3.32=the number of doublings required for a population to increase 1–log10 unit. Each LCK unit represents 1-log10 unit of cell killing (e.g., 1 LCK=90% kill, 2 LCK=99% kill, etc.).

C: Selection and Development of Drug Candidates

Example 13

In order to select the most appropriate compound to enter further experiments and to assess its suitability for use in a therapeutic composition for the treatment of disorders and diseases, such as cancers, additional data are collected. Such data can include the in vitro inhibition of the target molecule, such as a kinase, as measured by $IC_{50}$, or inhibition of proliferation across a panel of tumor cell lines, and tumor growth inhibition or reduction data and survival data from in vivo animal models. Furthermore, such experiments may also include the elucidation and/or determination of the mechanism of action of the subject compound, the target or target profile of the subject compound, and other characteristics of the subject compound, such as the binding affinity of the compound to the target(s) or the binding site of the compound on the target(s) and pharmacokinetic properties. Such experiments may also include molecular modelling of the drug-target interaction and the identification of metabolites formed after administration.

The compound that shows the most appropriate results for IC$_{50}$ for target inhibition, inhibition of cell proliferation, spectrum across various tumor cell lines, inhibition of tumour growth or tumour reduction data and/or animal-survival data, and/or other features, including ADME, pharmacokinetic and pharmacodynamic properties, may be chosen to enter further experiments. Such experiments may include, for example, therapeutic profiling and toxicology in animals, phase I clinical trials in humans and other clinical trails.

One skilled in the art readily appreciates that the present invention is well adapted to carry out the objects and obtain the ends and advantages mentioned, as well as those inherent therein. The methods and reagents described herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Those skilled in the art will recognize, or be able to ascertain using no more than routine experimentation, many equivalents to the specific embodiments of the invention described herein. Such equivalents are intended to be encompassed by the following claims. Those skilled in the art will also recognize that all combinations of embodiments, combination of aspects or features of the claims described herein are within the scope of the invention.

TABLE 1

Exemplary compounds of the present invention

| No. | Compound Structure | Compound Name |
|---|---|---|
| 3 | 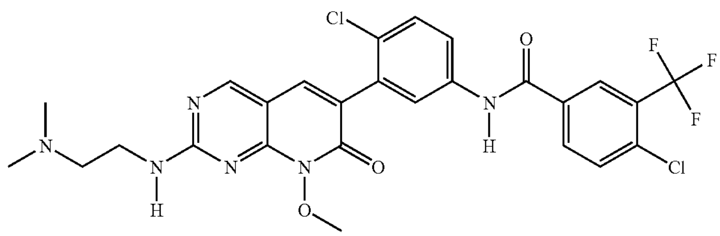 | 4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-3-trifluoromethyl-benzamide |
| 9 | 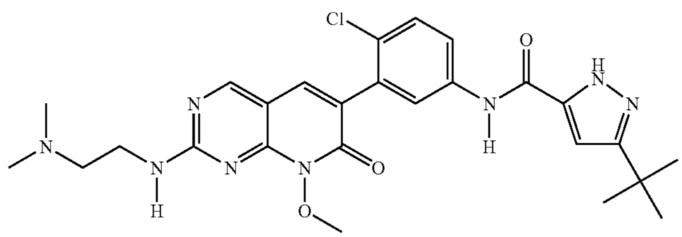 | 5-tert-Butyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide |
| 10 | 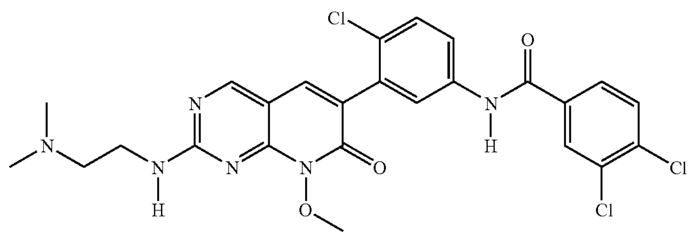 | 3,4-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide |
| 11 | 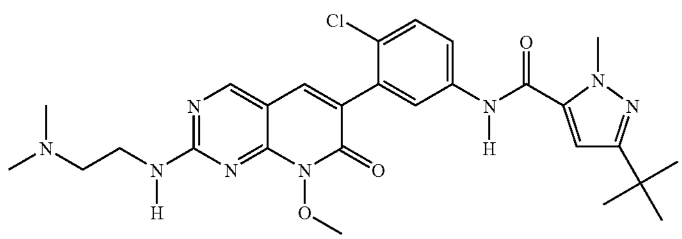 | 5-tert-Butyl-2-methyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide |
| 12 | 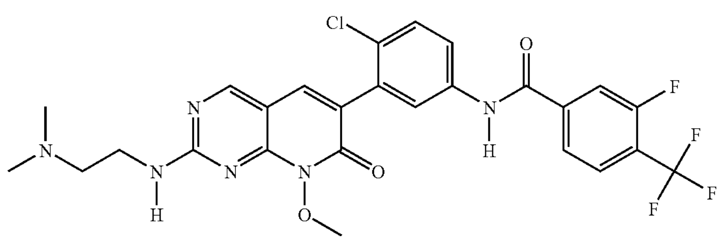 | N-{4-Chloro-3-[2-(2-dimethylamino-ethylamino)-8-methoxy-7-oxo-7,8-dihydro-pyrido[2,3-d]pyrimidin-6-yl]-phenyl}-3-fluoro-4-trifluoromethyl-benzamide |

TABLE 1-continued

Exemplary compounds of the present invention

| No. | Compound Structure | Compound Name |
|---|---|---|
| 13 | 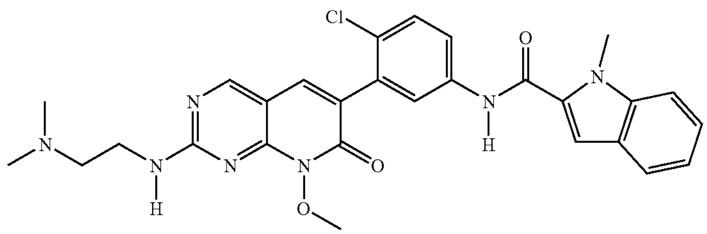 | 1-Methyl-1H-indole-2-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide |
| 14 | 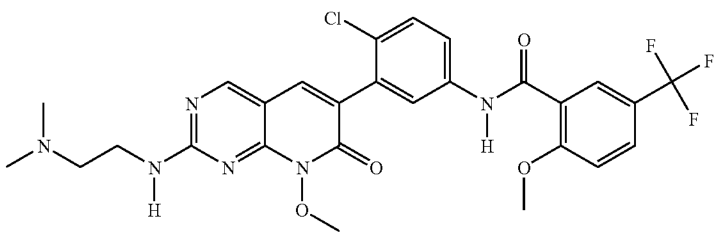 | N-{4-Chloro-3-[2-(2-dimethylamino-ethylamino)-8-methoxy-7-oxo-7,8-dihydro-pyrido[2,3-d]pyrimidin-6-yl]-phenyl}-2-methoxy-5-trifluoromethyl-benzamide |
| 15 | 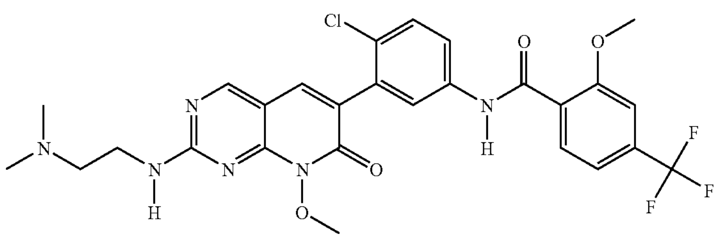 | N-{4-Chloro-3-[2-(2-dimethylamino-ethylamino)-8-methoxy-7-oxo-7,8-dihydro-pyrido[2,3-d]pyrimidin-6-yl]-phenyl}-2-methoxy-4-trifluoromethyl-benzamide |
| 16 | 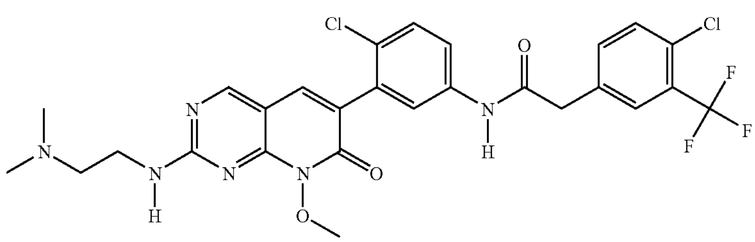 | N-{4-Chloro-3-[2-(2-dimethylamino-ethylamino)-8-methoxy-7-oxo-7,8-dihydro-pyrido[2,3-d]pyrimidin-6-yl]-phenyl}-2-(4-chloro-3-trifluoromethyl-phenyl)-acetamide |
| 17 | 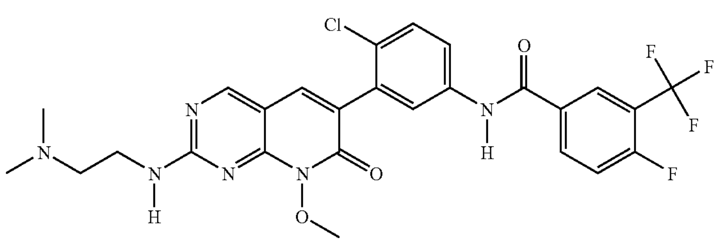 | N-{4-Chloro-3-[2-(2-dimethylamino-ethylamino)-8-methoxy-7-oxo-7,8-dihydro-pyrido[2,3-d]pyrimidin-6-yl]-phenyl)-4-fluoro-3-trifluoromethyl-benzamide |
| 18 | 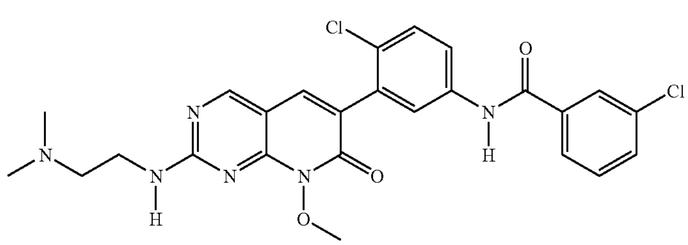 | 3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide |

TABLE 1-continued

Exemplary compounds of the present invention

| No. | Compound Structure | Compound Name |
|---|---|---|
| 19 | 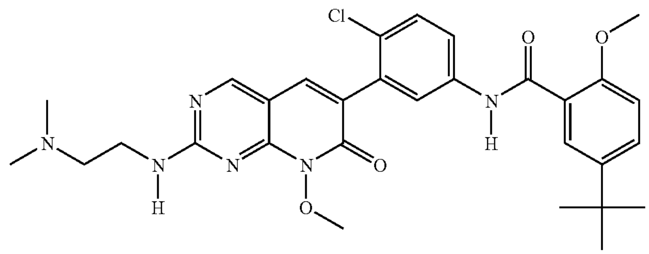 | 5-tert-Butyl-N-{4-chloro-3-[2-(2-dimethylamino-ethylamino)-8-methoxy-7-oxo-7,8-dihydro-pyrido[2,3-d]pyrimidin-6-yl]-phenyl}-2-methoxy-benzamide |
| 20 | 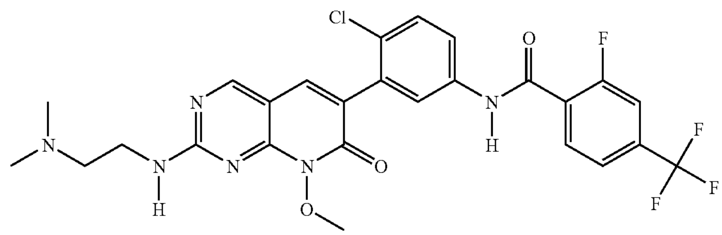 | N-{4-Chloro-3-[2-(2-dimethylamino-ethylamino)-8-methoxy-7-oxo-7,8-dihydro-pyrido[2,3-d]pyrimidin-6-yl]-phenyl}-2-fluoro-4-trifluoromethyl-benzamide |
| 21 | 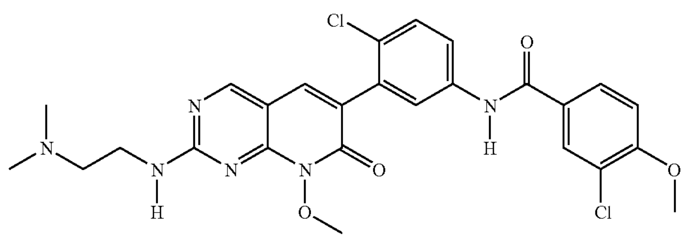 | 3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-4-methoxy-benzamide |
| 22 | 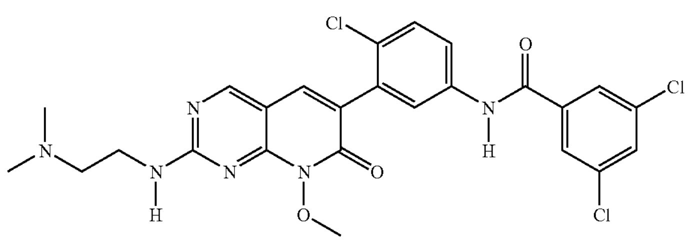 | 3,5-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide |
| 23 | 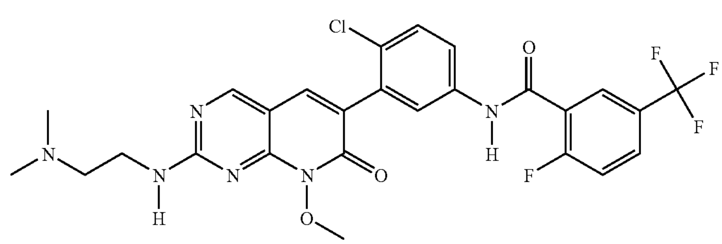 | N-{4-Chloro-3-[2-(2-dimethylamino-ethylamino)-8-methoxy-7-oxo-7,8-dihydro-pyrido[2,3-d]pyrimidin-6-yl]-phenyl]-2-fluoro-5-trifluoromethyl-benzamide |
| 24 | 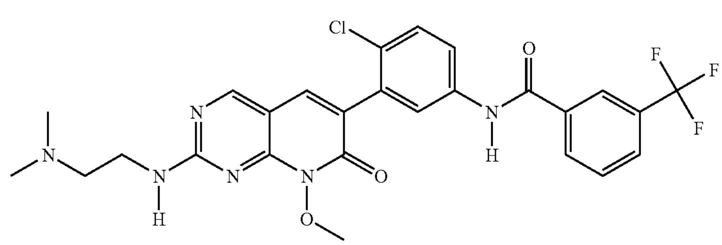 | N-{4-Chloro-3-[2-(2-dimethylamino-ethylamino)-8-methoxy-7-oxo-7,8-dihydro-pyrido[2,3-d]pyrimidin-6-yl]-phenyl}-3-trifluoromethyl-benzamide |

TABLE 1-continued

Exemplary compounds of the present invention

| No. | Compound Structure | Compound Name |
|---|---|---|
| 25 | 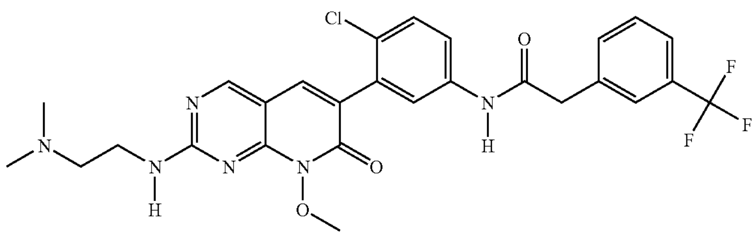 | N-{4-Chloro-3-[2-(2-dimethylamino-ethylamino)-8-methoxy-7-oxo-7,8-dihydro-pyrido[2,3-d]pyrimidin-6-yl]-phenyl}-2-(3-trifluoromethyl-phenyl)-acetamide |
| 26 | 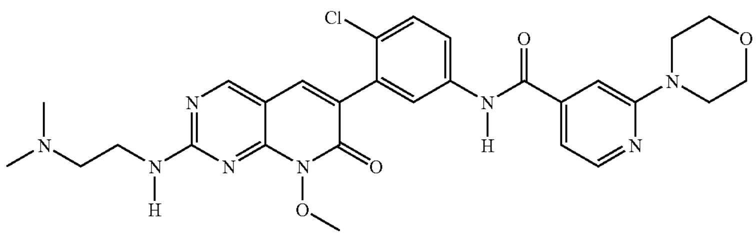 | N-{4-Chloro-3-[2-(2-dimethylamino-ethylamino)-8-methoxy-7-oxo-7,8-dihydro-pyrido[2,3-d]pyrimidin-6-yl]-phenyl}-2-morpholin-4-yl-isonicotinamide |
| 27 | 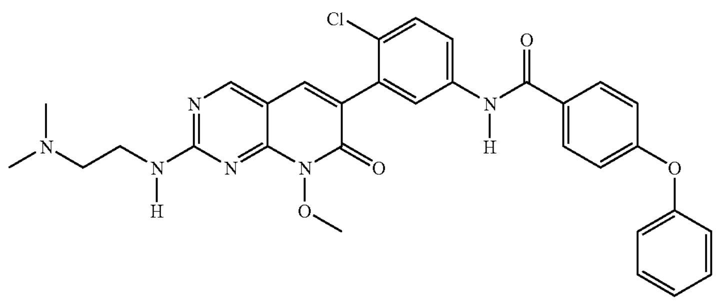 | N-{4-Chloro-3-[2-(2-dimethylamino-ethylamino)-8-methoxy-7-oxo-7,8-dihydro-pyrido[2,3-d]pyrimidin-6-yl]-phenyl}-4-phenoxy-benzamide |
| 28 | 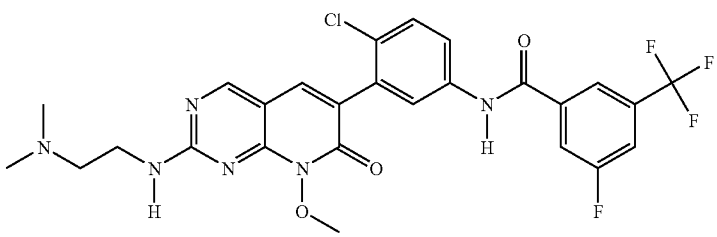 | N-{4-Chloro-3-[2-(2-dimethylamino-ethylamino)-8-methoxy-7-oxo-7,8-dihydro-pyrido[2,3-d]pyrimidin-6-yl]-phenyl-3-fluoro-5-trifluoromethyl-benzamide |
| 29 | 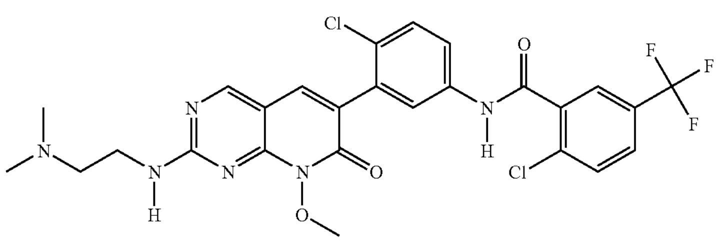 | 2-Chloro-N-{4-chloro-3-[2-(2-dimethylamino-ethylamino)-8-methoxy-7-oxo-7,8-dihydro-pyrido[2,3,-d]pyrimidin-6-yl]-phenyl}-5-trifluoromethyl-benzamide |
| 30 | 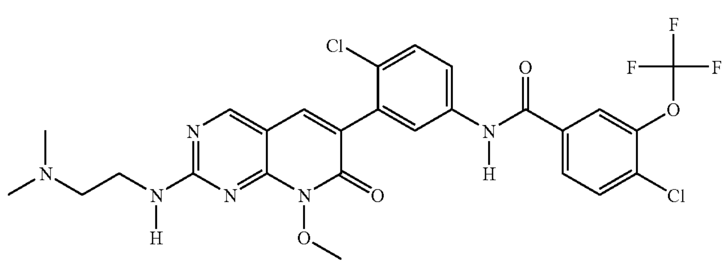 | 4-Chloro-N-(4-chloro-3-[2-(2-dimethylamino-ethylamino)-8-methoxy-7-oxo-7,8-dihydro-pyrido[2,3-d]pyrimidin-6-yl]-phenyl}-3-trifluoromethoxy-benzamide |

TABLE 1-continued

Exemplary compounds of the present invention

| No. | Compound Structure | Compound Name |
|---|---|---|
| 31 | 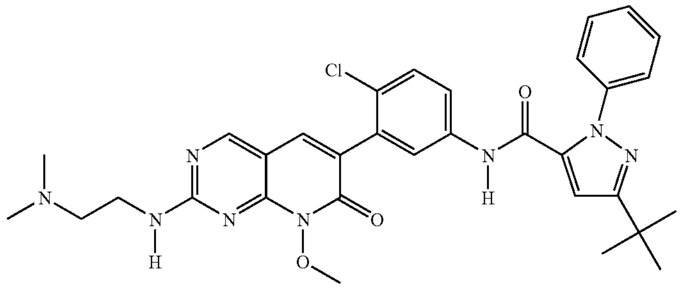 | 5-tert-Butyl-2-phenyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide |
| 32 | 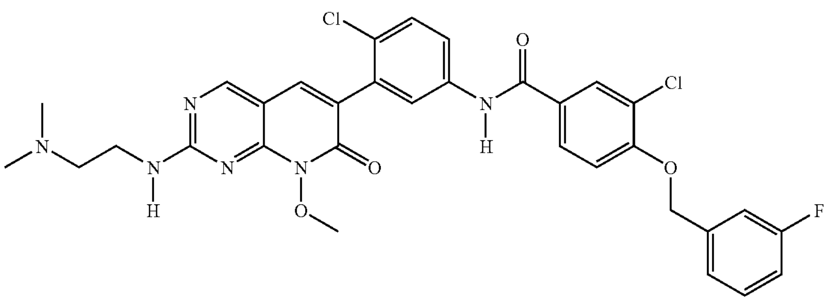 | 3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-4-(3-fluoro-benzyloxy)-benzamide |
| 33 | 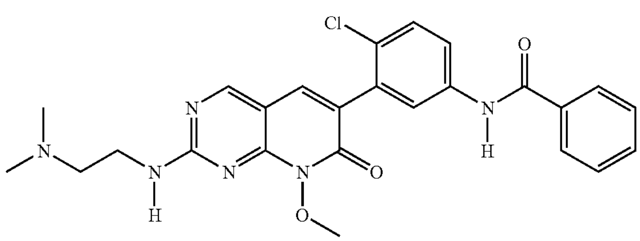 | N-{4-Chloro-3-[2-(2-dimethylamino-ethylamino)-8-methoxy-7-oxo-7,8-dihydro-pyrido[2,3-d]pyrimidin-6-yl]-phenyl}-benzamide |
| 34 | 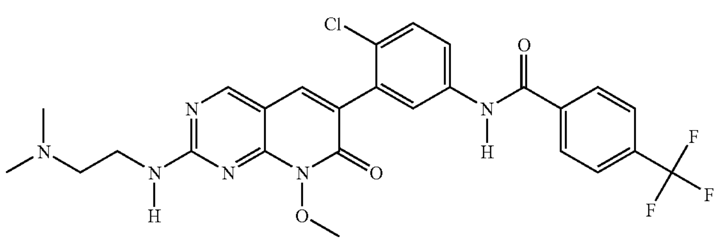 | N-{4-Chloro-3-[2-(2-dimethylamino-ethylamino)-8-methoxy-7-oxo-7,8-dihydro-pyrido[2,3-d]pyrimidin-6-yl]-phenyl}-4-trifluoromethyl-benzamide |
| 35 | 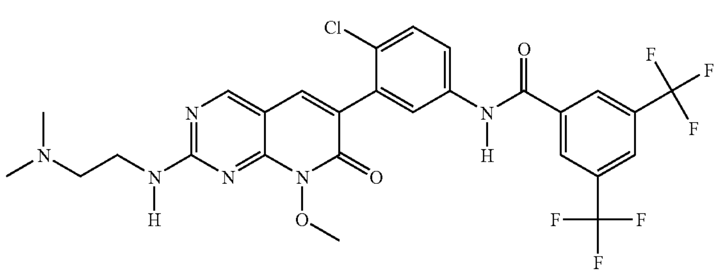 | N-{4-Chloro-3-[2-(2-dimethylamino-ethylamino)-8-methoxy-7-oxo-7,8-dihydro-pyrido[2,3-d]pyrimidin-6-yl]-phenyl}-3,5-bis-trifluoromethyl-benzamide |

TABLE 1-continued

Exemplary compounds of the present invention

| No. | Compound Structure | Compound Name |
|---|---|---|
| 36 | 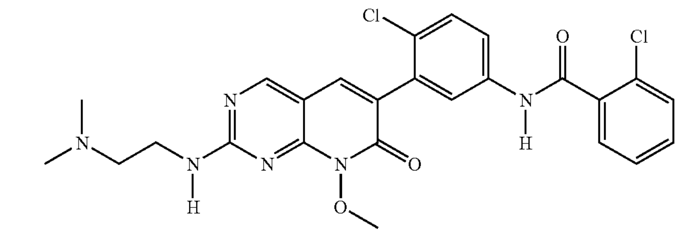 | 2-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide |
| 37 | 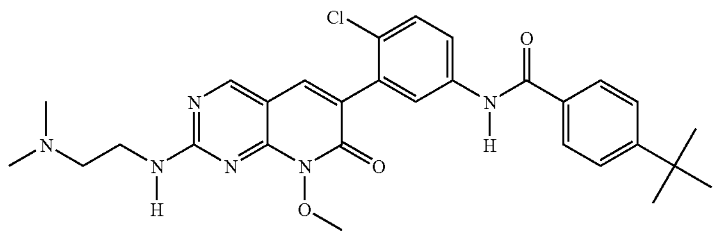 | 4-tert-Butyl-N-{4-chloro-3-[2-(2-dimethylamino-ethylamino)-8-methoxy-7-oxo-7,8-dihydro-pyrido[2,3-d]pyrimidin-6-yl]-phenyl)-benzamide |
| 38 | 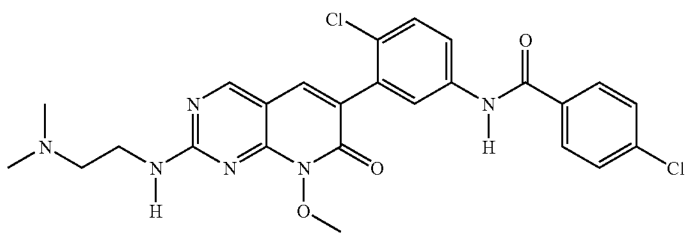 | 4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide |
| 39 | 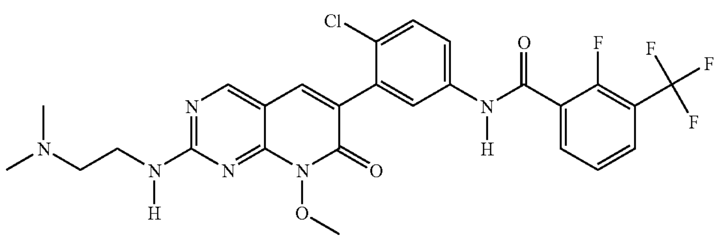 | N-{4-Chloro-3-[2-(2-dimethylamino-ethylamino)-8-methoxy-7-oxo-7,8-dihydro-pyrido[2,3-d]pyrimidin-6-yl]-phenyl}-2-fluoro-3-trifluoromethyl-benzamide |
| 40 | 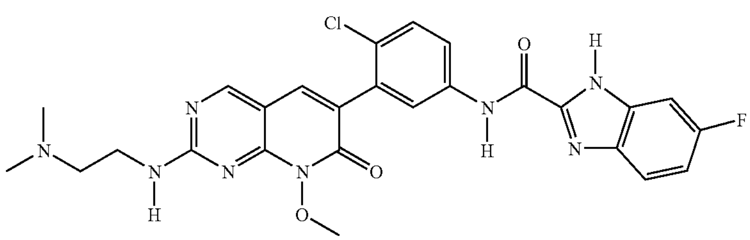 | 6-Fluoro-1H-benzoimidazole-2-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide |
| 4 | 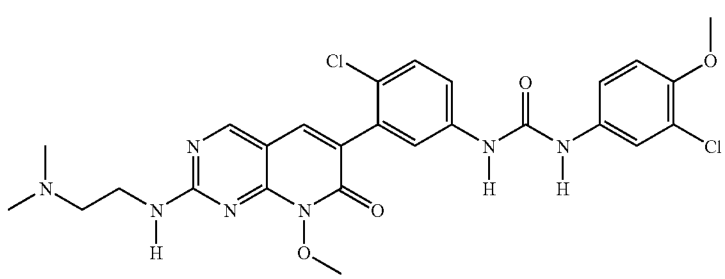 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(3-chloro-4-methoxy-phenyl)-urea |

TABLE 1-continued

Exemplary compounds of the present invention

| No. | Compound Structure | Compound Name |
| --- | --- | --- |
| 41 | 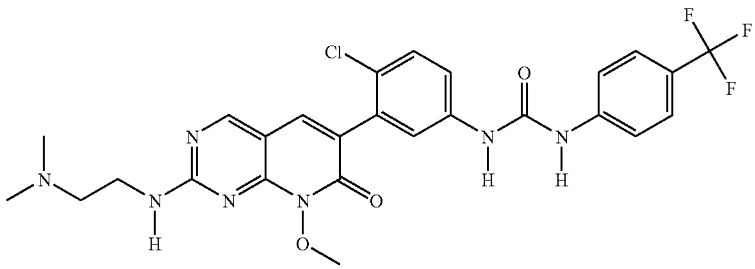 | 1-{ 4-Chloro-3-[2-(2-dimethylamino-ethylamino)-8-methoxy-7-oxo-7,8-dihydro-pyrido[2,3-d]pyrimidin-6-yl]-phenyl}-3-(4-trifluoromethyl-phenyl)-urea |
| 42 | 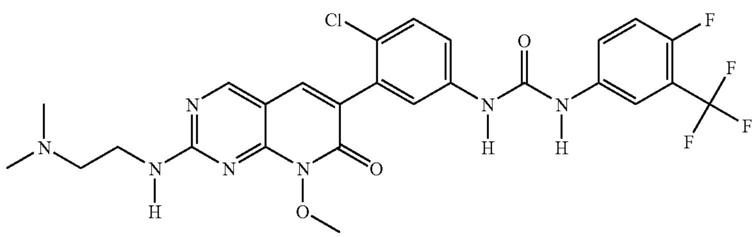 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(4-fluoro-3-trifluoromethyl-phenyl)-urea |
| 43 | 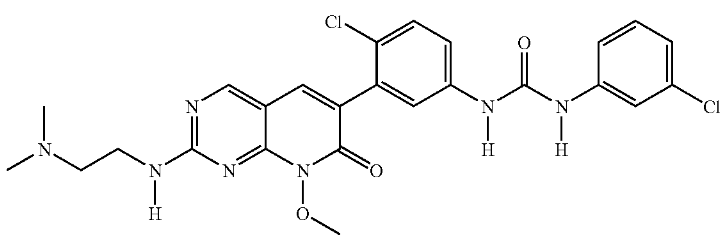 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(3-chloro-phenyl)-urea |
| 44 | 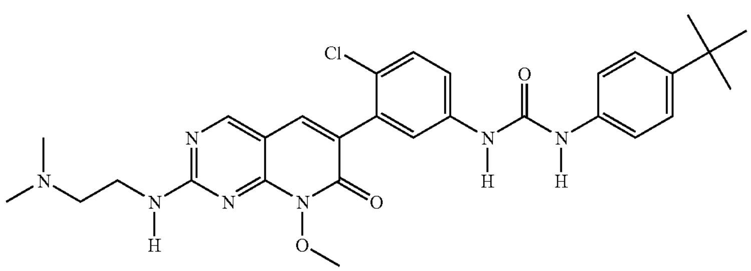 | 1-(4-tert-Butyl-phenyl)-3-{4-chloro-3-[2-(2-dimethylamino-ethylamino)-8-methoxy-7-oxo-7,8-dihydro-pyrido[2,3-d]pyrimidin-6-yl]-phenyl}-urea |
| 45 | 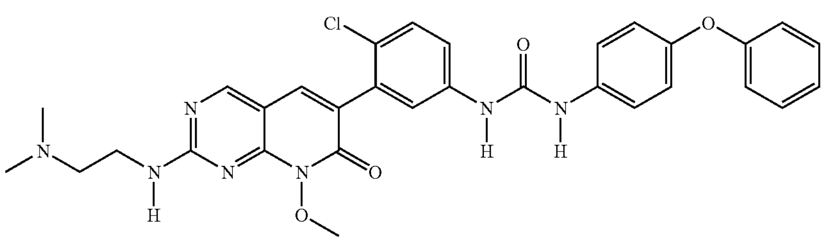 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(4-phenoxy-phenyl)-urea |
| 46 | 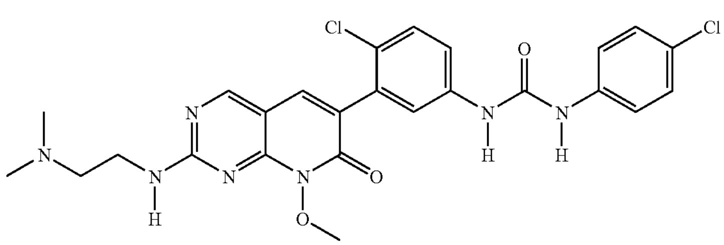 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(4-chloro-phenyl)-urea |

TABLE 1-continued

Exemplary compounds of the present invention

| No. | Compound Structure | Compound Name |
| --- | --- | --- |
| 47 | 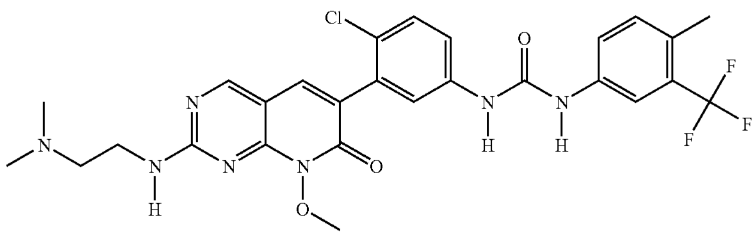 | 1-{4-Chloro-3-[2-(2-dimethylamino-ethylamino)-8-methoxy-7-oxo-7,8-dihydro-pyrido[2,3-d]pyrimidin-6-yl]-phenyl}-3-(4-methyl-3-trifluoromethyl-phenyl)-urea |
| 48 | 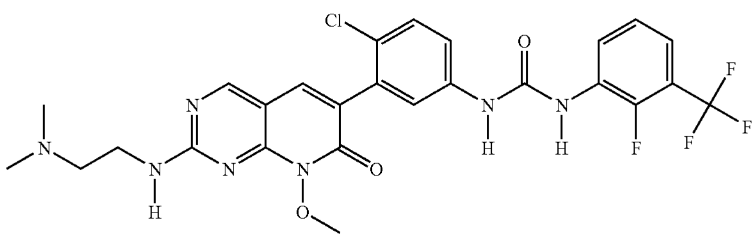 | 1-{4-Chloro-3-[2-(2-dimethylamino-ethylamino)8-methoxy-7-oxo-7,8-dihydro-pyrido[2,3-d]pyrimidin-6-yl]-phenyl}-3-(2-fluoro-3-trifluoromethyl-phenyl)-urea |
| 49 | 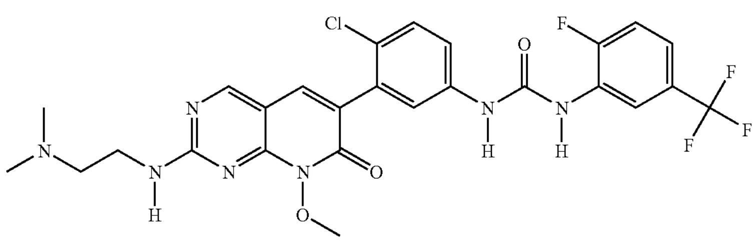 | 1-{4-Chloro-3-[2-(2-dimethylamino-ethylamino)-8-methoxy-7-oxo-7,8-dihydro-pyrido[2,3-d]pynmidin-6-yl]-phenyl}-3-(2-fluoro-5-trifluoromethyl-phenyl)-urea |
| 50 | 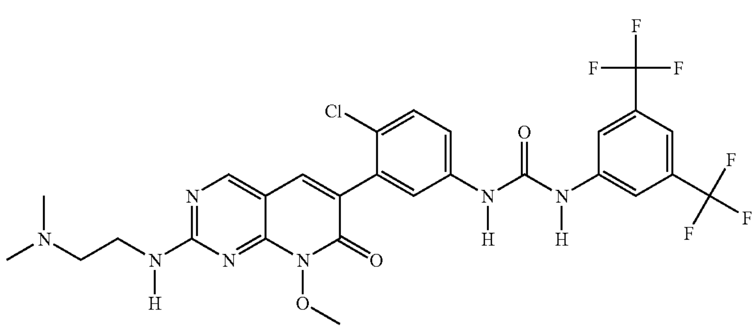 | 1-(3,5-Bis-trifluoromethyl-phenyl)-3-{4-chloro-3-[2-(2-dimethylamino-ethylamino)-8-methoxy-7-oxo-7,8-dihydro-pyrido[2,3-d]pyrimidin-6-yl]-phenyl}-urea |
| 6 | 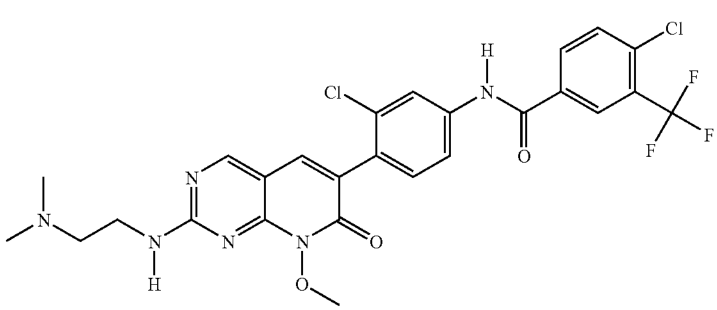 | 4-Chloro-N-{3-chloro-4-[2-(2-dimethylamino-ethylamino)-8-methoxy-7-oxo-7,8-dihydro-pyrido[2,3-d]pyrimidin-6-yl]-phenyl}-3-trifluoromethyl-benzamide |

TABLE 1-continued

Exemplary compounds of the present invention

| No. | Compound Structure | Compound Name |
|---|---|---|
| 51 | 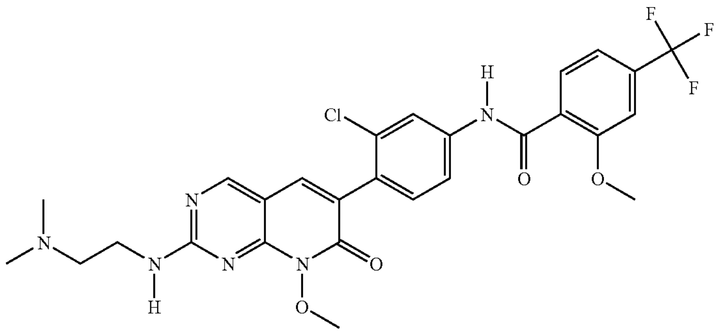 | N-{3-Chloro-4-[2-(2-dimethylamino-ethylamino)-8-methoxy-7-oxo-7,8-dihydro-pyrido[2,3-d]pyrimidin-6-yl]-phenyl}-2-methoxy-4-trifluoromethyl-benzamide |
| 52 | 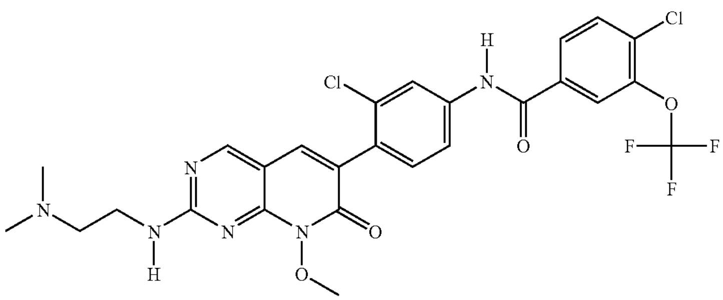 | 4-Chloro-N-{3-chloro-4-[2-(2-dimethylamino-ethylamino)-8-methoxy-7-oxo-7,8-dihydro-pyrido[2,3-d]pyrimidin-6-yl]-phenyl}-3-trifluoromethoxy-benzamide |
| 53 | 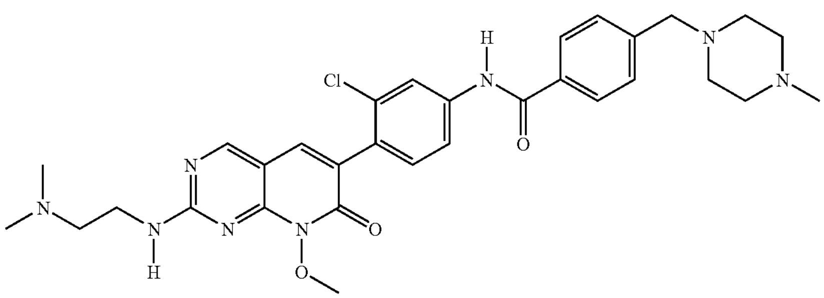 | N-{3-Chloro-4-[2-(2-dimethylamino-ethylamino)-8-methoxy-7-oxo-7,8-dihydro-pyrido[2,3-d]pyrimidin-6-yl]-phenyl }-4-(4-methyl-piperazin-1-ylmethyl)-benzamide |
| 54 | 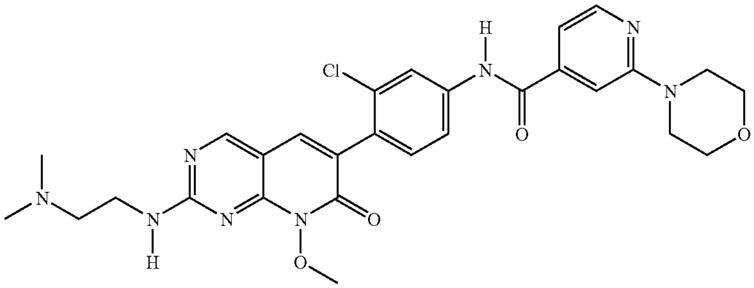 | N-{3-Chloro-4-[2-(2-dimethylamino-ethylamino)-8-methoxy-7-oxo-7,8-dihydro-pyrido[2,3-d]pymidin-6-yl]-phenyl}-2-morpholin-4-yl-isonicotinamide |

TABLE 1-continued

Exemplary compounds of the present invention

| No. | Compound Structure | Compound Name |
|---|---|---|
| 55 | 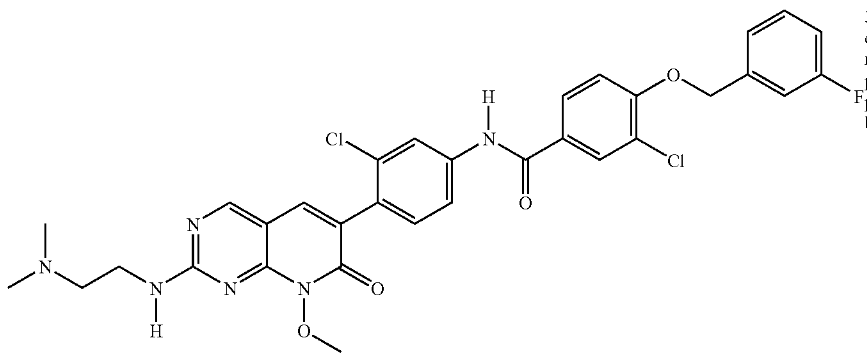 | 3-Chloro-N-{3-chloro-4-[2-(2-dimethylamino-ethylamino)-8-methoxy-7-oxo-7,8-dihydro-pyrido[2,3-d]pyrimidin-6-yl]-phenyl}-4-(3-fluoro-benzyloxy)-benzamide |
| 56 | 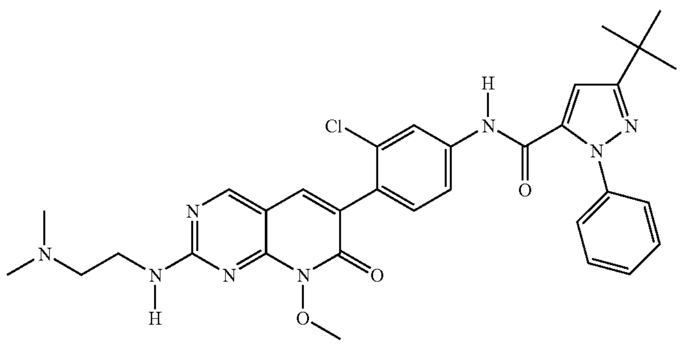 | 5-tert-Butyl-2-phenyl-2H-pyrazole-3-carboxylic acid {3-chloro-4-[2-(2-dimethylamino-ethylamino)-8-methoxy-7-oxo-7,8-dihydro-pyrido[2,3-d]pyrimidin-6-yl]-phenyl}-amide |
| 57 | 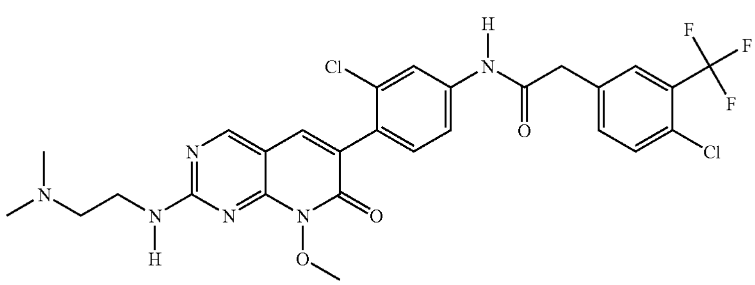 | N-{3-Chloro-4-[2-(2-dimethylamino-ethylamino)-8-methoxy-7-oxo-7,8-dihydro-pyrido[2,3-d]pyrimidin-6-yl]-phenyl}-2-(4-chloro-3-trifluoromethyl-phenyl)-acetamide |
| 7 | 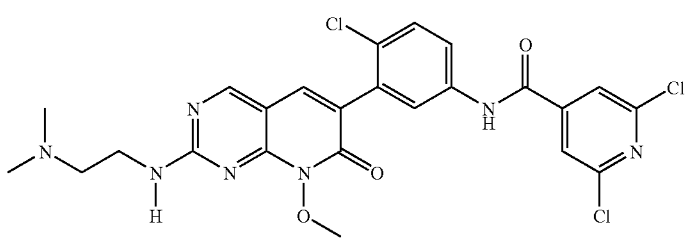 | 2,6-Dichloro-N-(4-chloro-3-(2-(2-(dimethylamino)ethylamino)-8-methoxy-7-oxo-7,8-dihydropyrido[2,3-d]pyrimidin-6-yl)phenyl)-isonicotinamide |
| 58 | 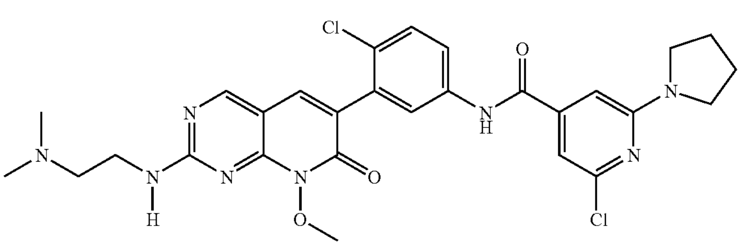 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-pyrrolidin-1-yl-isonicotinamide |

TABLE 1-continued

Exemplary compounds of the present invention

| No. | Compound Structure | Compound Name |
|---|---|---|
| 59 | 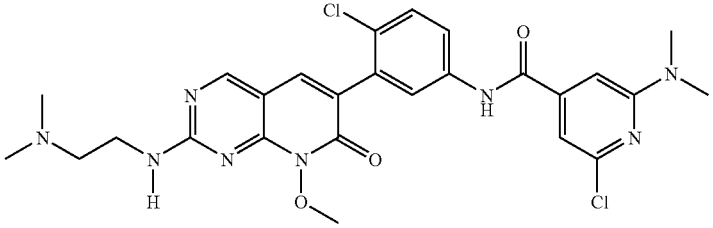 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-dimethylamino-isonicotinamide |
| 60 | 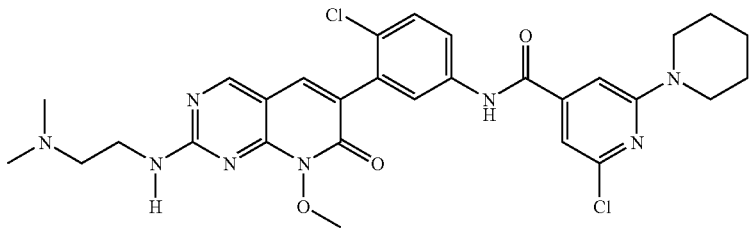 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-pyperidin-1-yl-isonicotinamide |
| 61 | 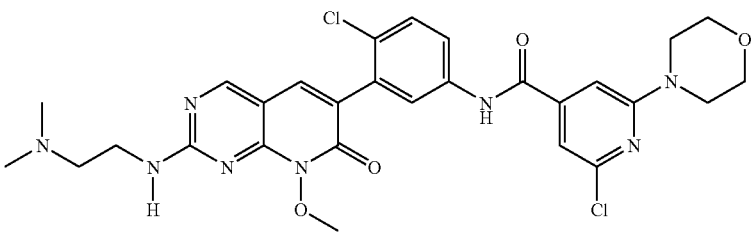 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-morpholin-4-yl-isonicotinamide |
| 62 | 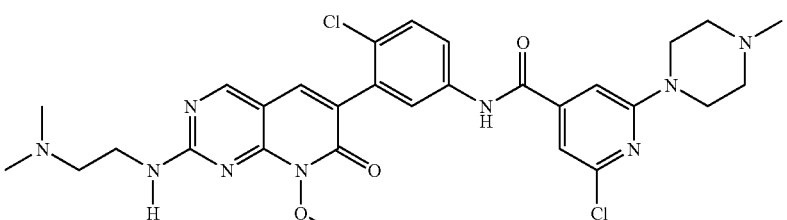 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(4-methyl-piperazin-1-yl)-isonicotinamide |
| 8 | 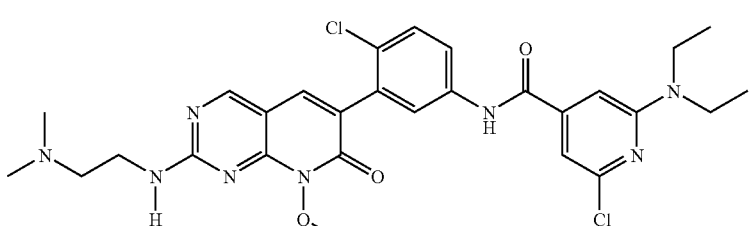 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-diethylamino-isonicotinamide |
| 63 | 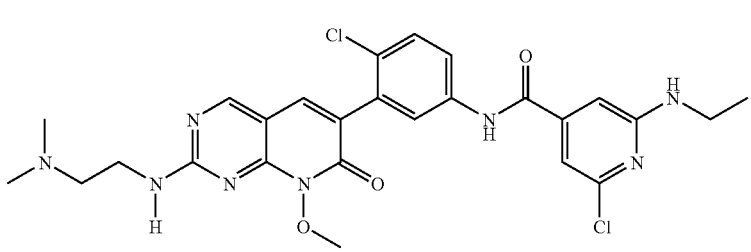 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-ethylamino-isonicotinamide |

TABLE 1-continued

Exemplary compounds of the present invention

| No. | Compound Structure | Compound Name |
|---|---|---|
| 64 | 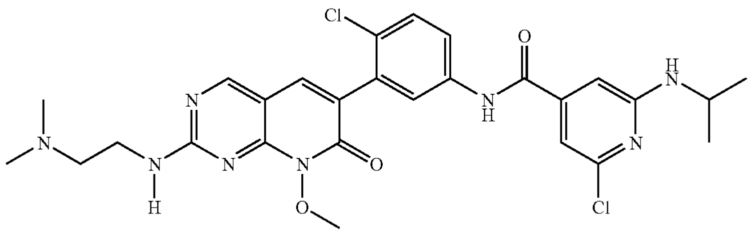 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-isopropylamino-isonicotinamide |
| 65 | 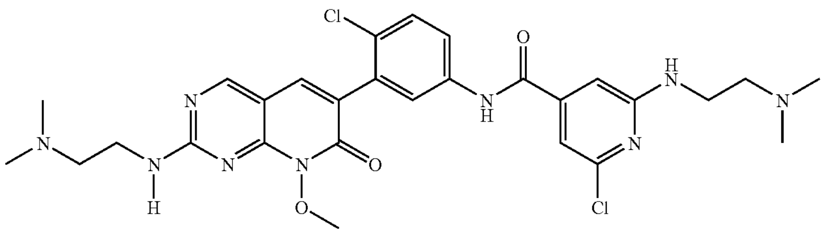 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(2-dimethylaminoethylamino)-isonicotinamide |
| 66 | 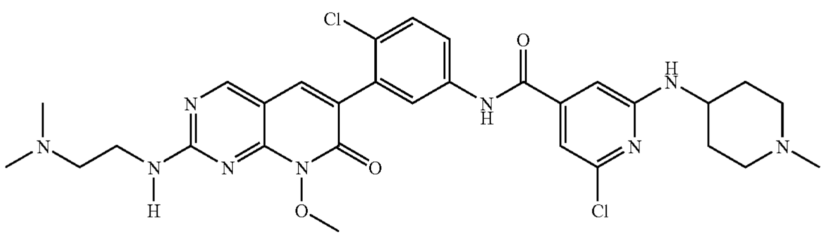 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-1-methyl-piperidine-4-ylamino)-isonicotinamide |
| 67 | 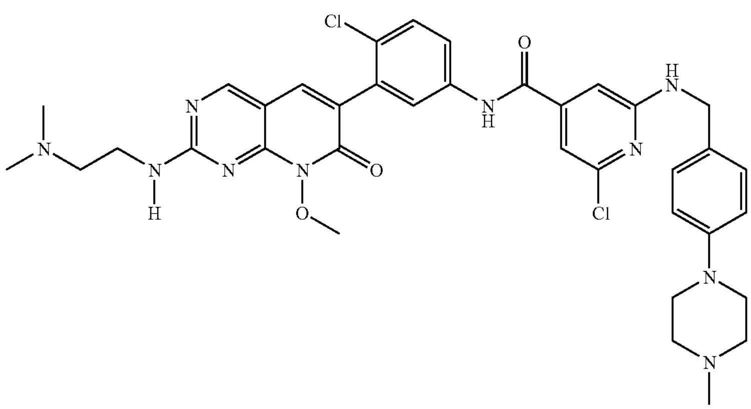 | 2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-(4-(4-methylpiperazin-1-yl)-benzylamino)-isonicotinamide |

TABLE 2

Characterization of exemplary compounds

| Compound Number | HPLC retention time [Method: min] | Mass $[M + H]^+$ ($[M + 2H]^{2+}$) | UV [nm] |
|---|---|---|---|
| 3 | B: 6.81 | 595 | 240, 290, 340 |
| 9 | B: 6.38 | 539 | 230, 290, 345 |
| 10 | B: 6.72 | 561 | 235, 295, 345 |
| 11 | B: 6.52 | 553 | 235, 280, 340 |
| 12 | B: 6.70 | 579 | 235, 290, 345 |
| 13 | B: 6.63 | 546 | 230, 330 |
| 14 | B: 6.65 | 591 | 230, 290, 350 |
| 15 | B: 6.66 | 591 | 230, 295, 345 |
| 16 | B: 6.77 | 609 | 230, 345 |
| 17 | B: 6.68 | 579 | 225, 290, 350 |
| 18 | B: 6.49 | 527 | 230, 290, 350 |
| 19 | B: 6.85 | 579 | 225, 295, 345 |
| 20 | B: 6.58 | 579 | 235, 290, 340 |
| 21 | B: 6.49 | 557 | 230, 290, 345 |
| 22 | B: 6.76 | 561 | 230, 285, 345 |
| 23 | B: 6.56 | 579 | 230, 290, 340 |
| 24 | B: 6.60 | 561 | 230, 295, 345 |
| 25 | B: 6.60 | 575 | 225, 250, 290, 350 |

TABLE 2-continued

Characterization of exemplary compounds

| Compound Number | HPLC retention time [Method: min] | Mass $[M + H]^+$ $([M + 2H])^{2+}$ | UV [nm] |
|---|---|---|---|
| 26 | B: 5.93 | 579 | 225, 250, 295, 345 |
| 27 | B: 6.80 | 585 | 225, 285, 350 |
| 28 | B: 6.70 | 579 | 230, 290, 345 |
| 29 | B: 6.62 | 595 | 230, 295, 345 |
| 30 | B: 6.85 | 611 | 235, 295, 340 |
| 31 | B: 6.85 | 615 | 225, 290, 345 |
| 32 | B: 7.03 | 651 | 225, 295, 345 |
| 33 | B: 6.21 | 493 | 230, 290, 345 |
| 34 | B: 6.61 | 561 | 230, 290, 345 |
| 35 | B: 6.92 | 629 | 230, 290, 350 |
| 36 | B: 6.28 | 527 | 225, 290, 350 |
| 37 | B: 6.80 | 549 | 230, 285, 345 |
| 38 | B: 6.49 | 527 | 235, 340 |
| 39 | B: 6.57 | 579 | 230, 290, 345 |
| 40 | B: 6.42 | 551 | 230, 310, 340 |
| 4 | B: 6.56 | 572 | 230, 260, 345 |
| 41 | B: 6.85 | 576 | 220, 270, 345 |
| 42 | B: 6.85 | 594 | 220, 260, 340 |
| 43 | B: 6.65 | 542 | 225, 265, 350 |
| 44 | B: 6.97 | 564 | 265, 345 |
| 45 | B: 6.94 | 600 | 225, 265, 345 |
| 46 | B: 6.69 | 542 | 220, 265, 345 |
| 47 | B: 6.93 | 590 | 220, 260, 340 |
| 48 | B: 6.88 | 594 | 220, 255, 290, 345 |
| 49 | B: 6.91 | 594 | 225, 260, 345 |
| 50 | B: 7.09 | 644 | 220, 260, 345 |
| 6 | B: 6.86 | 595 | 235, 300, 350 |
| 51 | B: 6.70 | 591 | 230, 300, 350 |
| 52 | B: 6.90 | 611 | 230, 300, 350 |
| 53 | B: 5.43 | 605 (303) | 225, 295, 350 |
| 54 | B: 5.94 | 579 | 225, 250, 300, 350 |
| 55 | B: 7.08 | 651 | 225, 300, 350 |
| 56 | B: 6.92 | 615 | 235, 270, 300, 340 |
| 57 | B: 6.82 | 609 | 230, 255, 295, 345 |
| 7 | C: 2.49 | 562 | 231, 292, 341 |
| 58 | C: 2.67 | 597 | 227, 268, 345 |
| 59 | C: 2.58 | 571 | 225, 266, 347 |
| 60 | C: 2.85 | 611 | 228, 270, 344 |
| 61 | C: 2.51 | 613 | 265, 335 |
| 62 | C: 1.88 | 626 (314) | 255, 335 |
| 8 | C: 2.83 | 599 | 232, 272, 341 |
| 63 | D: 5.41 | 571 | 227, 254, 343 |
| 64 | D: 5.70 | 585 | 198, 256, 344 |
| 65 | D: 4.25 | 614 (307) | 194, 251, 292, 343 |
| 66 | D: 4.37 | 640 (321) | 194, 253, 343 |
| 67 | D: 4.82 | 731 (366) | 198, 253 343 |

TABLE 3

Inhibition values of exemplary compounds (columns 2 and 3); and inhibition of tumor cell growth (columns 4 and 5)

| Compound number | Biochemical inhibition [%] C-Raf | Biochemical inhibition [%] p38 | CELLULAR IC$_{50}$ [μM] HT-29 [B-Raf V600E mutant] | CELLULAR IC$_{50}$ [μM] A-431 [B-Raf wildtype] |
|---|---|---|---|---|
| 3 | nd | nd | <5 | >10 |
| 9 | nd | nd | >10 | >10 |
| 10 | >70% | >70% | <5 | >10 |
| 11 | nd | nd | <10 | >10 |
| 12 | nd | nd | <10 | >10 |
| 13 | nd | nd | <10 | >10 |
| 14 | nd | nd | <5 | >10 |
| 15 | nd | nd | <5 | >10 |
| 16 | >70% | >70% | <5 | >10 |
| 17 | >70% | >70% | <5 | >10 |
| 18 | >70% | >70% | <10 | >10 |
| 19 | nd | nd | ? | ? |
| 20 | nd | nd | >10 | >10 |
| 21 | nd | nd | <5 | >10 |
| 22 | nd | nd | <5 | >10 |
| 23 | >70% | >70% | <5 | >10 |
| 24 | >70% | >70% | <5 | >10 |
| 25 | nd | nd | <5 | >10 |
| 26 | >70% | >70% | <10 | >10 |
| 27 | >70% | >70% | <5 | <10 |
| 28 | >70% | >70% | <5 | >10 |
| 29 | nd | nd | <10 | >10 |
| 30 | >70% | >70% | <5 | >10 |
| 31 | ~70% | >70% | <5 | <10 |
| 32 | >70% | >70% | <5 | >10 |
| 33 | nd | nd | >10 | >10 |
| 34 | nd | nd | <10 | >10 |
| 35 | nd | nd | <5 | >10 |
| 36 | nd | nd | >10 | >10 |
| 37 | >70% | >70% | <5 | <10 |
| 38 | nd | nd | >10 | >10 |
| 39 | >70% | >70% | <5 | >10 |
| 40 | nd | nd | >10 | >10 |
| 4 | >70% | >70% | <10 | >10 |
| 41 | >70% | >70% | <5 | <10 |
| 42 | >70% | >70% | <5 | <10 |
| 43 | >70% | >70% | <5 | >10 |
| 44 | >70% | >70% | <5 | <5 |
| 45 | nd | nd | <5 | <10 |
| 46 | nd | nd | <5 | >10 |
| 47 | >70% | >70% | <5 | >5 |
| 48 | nd | nd | <5 | >10 |
| 49 | nd | nd | <5 | >10 |
| 50 | >70% | >70% | <5 | <10 |
| 6 | | | <5 | <10 |
| 51 | nd | nd | <5 | <10 |
| 52 | nd | nd | <5 | <10 |
| 53 | nd | nd | >10 | >10 |
| 54 | nd | nd | >10 | >10 |
| 55 | nd | nd | <5 | wildtype |
| 56 | nd | nd | <5 | <10 |
| 57 | nd | nd | <10 | <10 |
| 7 | nd | nd | <10 | >10 |
| 58 | nd | nd | <5 | <10 |
| 59 | nd | nd | <5 | >10 |
| 60 | nd | nd | <5 | <10 |
| 61 | >70% | >70% | <5 | >10 |
| 62 | nd | nd | <5 | >10 |
| 8 | >70% | >70% | <5 | <10 |
| 63 | nd | nd | <5 | >10 |
| 64 | >70% | >70% | <5 | >10 |
| 65 | nd | nd | <10 | >10 |
| 66 | nd | nd | <10 | >10 |
| 67 | nd | nd | <5 | <10 |

TABLE 4

Substitution pattern at $R^6$ for exemplary compounds:
Compound 32:
Substituent $R^6$: substituted aryl

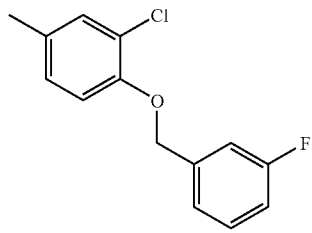

aryl = phenyl
Substituent A (m-Cl) = —[$(R^{Sm})_n$] with n = 1: $R^{S1}$ = —Cl
Substituent B (p-OR) = —[$(R^{Sm})_n$] with n = 3: $R^{S1}$ = —O—$R^a$; $R^{S2}$ =-aryl; $R^{S3}$ = —F
Compound 52:
Substituent $R^6$: substituted aryl

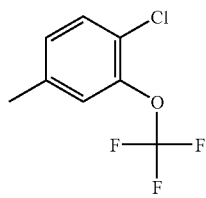

aryl = phenyl
Substituent A (p-Cl) = —[$(R^{Sm})_n$] with n = 1: $R^{S1}$ = —Cl
Substituent B (m-OCF$_3$) = —[$(R^{Sm})_n$] with n = 4: $R^{S1}$ = —O—$R^a$; $R^{S2}$, $R^{S3}$, $R^{S4}$ = —F
Compound 67:
Substituent $R^6$: substituted heteroaryl

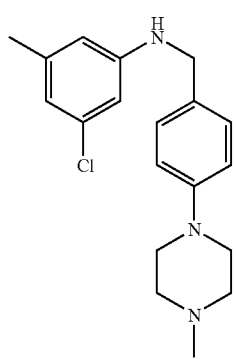

heteroaryl = pyridyl
Substituent A (2-Cl) = —[$(R^{Sm})_n$] with n = 1: $R^{S1}$ = —Cl
Substituent B (6-NHR) = —[$(R^{Sm})_n$] with n =4: $R^{S1}$ = —N$(R^a)_2$; $R^{S2}$= —aryl; $R^{S3}$= —heterocycloalkyl; $R^{S4}$ = —alkyl

EQUIVALENTS

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference.

The invention claimed is:

1. A compound having a structure represented by formula (I)

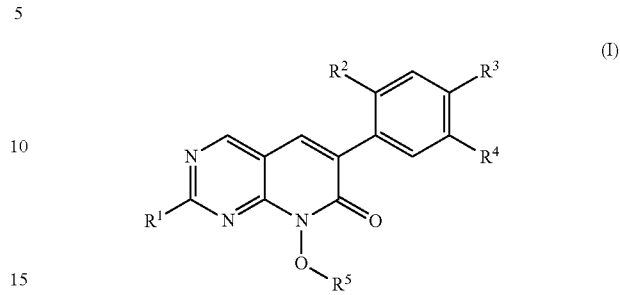

or any tautomeric form thereof, wherein $R^1$ is selected from hydrogen, —NH$_2$, and substituted or unsubstituted: —NH—C$_{1-6}$-alkyl, —NH-cycloalkyl, —NH-heterocycloalkyl, —NH—C$_{1-6}$-alkylene-OR$^7$, and —NH—C$_{1-6}$-alkylene-NR$^7_2$;

$R^2$ is selected from hydrogen, -halogen, -methyl, —CH$_2$F, —CHF$_2$, —CF$_3$, —O—methyl, —O—CH$_2$F, —O—CHF$_2$, and —O—CF$_3$;

one of $R^3$ and $R^4$ is hydrogen, and the other is —NH—C(=O)—(NH)$_x$—(CH$_2$)$_y$—R$^6$, wherein x and y are independently selected from 0 and 1;

$R^5$ is selected from hydrogen, and substituted or unsubstituted: -alkyl, -alkenyl, -alkynyl, -cycloalkyl, -cycloalkenyl, —(C-linked-heterocycloalkyl), —(C-linked-heterocycloalkenyl), -aryl, and -heteroaryl;

$R^6$ is selected from substituted or unsubstituted aryl, and substituted or unsubstituted heteroaryl;

$R^7$ is independently selected from hydrogen and —C$_{1-6}$-alkyl;

or any pharmaceutically acceptable salt or N-oxide thereof; provided, however, that compound (A) is excluded:

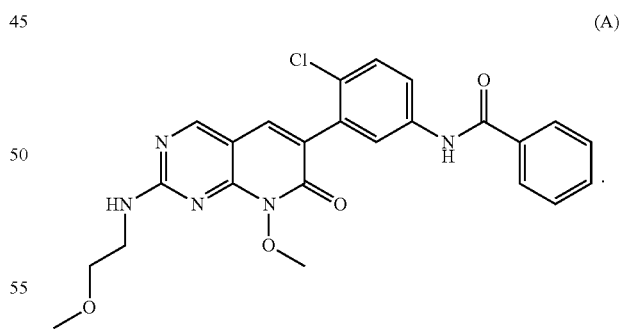

2. The compound of claim 1, wherein $R^1$ is substituted or unsubstituted —NH—C$_{1-6}$-alkylene-N$(R^7)_2$.

3. The compound of claim 1, wherein $R^2$ is selected from hydrogen and chlorine.

4. The compound of claim 1, wherein $R^5$ is selected from substituted or unsubstituted -alkyl, and substituted or unsubstituted -cycloalkyl.

5. The compound of claim 4, wherein $R^5$ is -methyl.

6. The compound of claim 1 having a structure represented by formula (Ia)

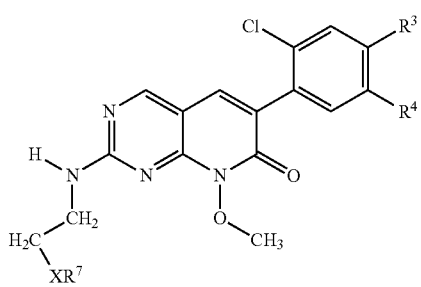

or any tautomeric or stereoisomeric form thereof, wherein X is selected from —O— and —NR$^7$.

7. The compound of claim 6, wherein X is —NR$^7$.

8. The compound of claim 1, wherein the compound is selected from:

4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-3-trifluoromethyl-benzamide;

5-tert-Butyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide;

3,4-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide;

5-tert-Butyl-2-methyl-2H-pyrazole-3-carboxylic acid {4-chloro-3-[2-(2-dimethylamino-ethylamino)-8-methoxy-7-oxo-7,8-dihydro-pyrido[2,3-d]pyrimidin-6-yl]-phenyl}-amide;

N-{4-Chloro-3-[2-(2-dimethylamino-ethylamino)-8-methoxy-7-oxo-7,8-dihydro-pyrido [2,3-d]pyrimidin-6-yl]-phenyl}-3-fluoro-4-trifluoromethyl-benzamide;

1-Methyl-1H-indole-2-carboxylic acid {4-chloro-3-[2-(2-dimethylamino-ethylamino) -8-methoxy-7-oxo-7,8-dihydro-pyrido[2,3-d]pyrimidin-6-yl]-phenyl}-amide;

N-{4-Chloro-3-[2-(2-dimethylamino-ethylamino)-8-methoxy-7-oxo-7,8-dihydro-pyrido [2,3-d]pyrimidin-6-yl]-phenyl}-2-methoxy-5-trifluoromethyl-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-methoxy-4-trifluoromethyl-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-(4-chloro-3-trifluoromethyl-phenyl)-acetamide;

N-{4-Chloro-3-[2-(2-dimethylamino-ethylamino)-8-methoxy-7-oxo-7,8-dihydro-pyrido [2,3-d]pyrimidin-6-yl]-phenyl}-4-fluoro-3-trifluoromethyl-benzamide;

3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide;

5-tert-Butyl-N-{4-chloro-3-[2-(2-dimethylamino-ethylamino)-8-methoxy-7-oxo-7,8-dihydro-pyrido[2,3-d]pyrimidin-6-yl]-phenyl}-2-methoxy-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-4-trifluoromethyl-benzamide;

3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-4-methoxy-benzamide;

3,5-Dichloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-5-trifluoromethyl-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-3-trifluoromethyl-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-(3-trifluoromethyl-phenyl)-acetamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-morpholin-4-yl-isonicotinamide;

N-{4-Chloro-3-[2-(2-dimethylamino-ethylamino)-8-methoxy-7-oxo-7,8-dihydro-pyrido [2,3-d]pyrimidin-6-yl]-phenyl}-4-phenoxy-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-3-fluoro-5-trifluoromethyl-benzamide;

2-Chloro-N-{4-chloro-3-[2-(2-dimethylamino-ethylamino)-8-methoxy-7-oxo-7,8-dihydro-pyrido[2,3-d]pyrimidin-6-yl]-phenyl}-5-trifluoromethyl-benzamide;

4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-3-trifluoromethoxy-benzamide;

5-tert-Butyl-2-phenyl-2H-pyrazole-3-carboxylic acid {4-chloro-3-[2-(2-dimethylamino-ethylamino)-8-methoxy-7-oxo-7,8-dihydro-pyrido[2,3-d]pyrimidin -6-yl]-phenyl-amide;

3-Chloro-N-{4-chloro-3-[2-(2-dimethylamino-ethylamino)-8-methoxy-7-oxo-7,8-dihydro-pyrido[2,3-d]pyrimidin-6-yl]-phenyl}-4-(3-fluoro-benzyloxy)-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-4-trifluoromethyl-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-3,5-bis-trifluoromethyl-benzamide, 2-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide;

4-tert-Butyl-N-{4-chloro-3-[2-(2-dimethylamino-ethylamino)-8-methoxy-7-oxo-7,8-dihydro-pyrido[2,3-d]pyriniidin-6-yl]-phenyl}-benzamide;

4-Chloro-N-{4-chloro-3-[2-(2-dimethylamino-ethylamino)-8-methoxy-7-oxo-7,8-dihydro-pyrido[2,3-d]pyrimidin-6-yl]-phenyl}-benzamide;

N-{4-Chloro-3-[2-(2-dimethylamino-ethylamino)-8-methoxy-7-oxo-7,8-dihydro-pyrido [2,3-d]pyrimidin-6-yl]-phenyl}-2-fluoro-3-trifluoromethyl-benzamide;

6-Fluoro-1H-benzoimidazole-2-carboxylic acid {4-chloro-3-[2-(2-dimethylamino-ethylamino)-8-methoxy-7-oxo-7,8-dihydro-pyrido[2,3-d]pyrimidin -6-yl]-phenyl}-amide;

1-{4-Chloro-3-[2-(2-dimethylamino-ethylamino)-8-methoxy-7-oxo-7,8-dihydro-pyrido [2,3-d]pyrimidin-6-yl]-phenyl}-3-(3-chloro-4-methoxy-phenyl)-urea;

1-{4-Chloro-3-[2-(2-dimethylamino-ethylamino)-8-methoxy-7-oxo-7,8-dihydro-pyrido [2,3-d]pyrimidin-6-yl]-phenyl}-3-(4-trifluoromethyl-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-fluoro-3-trifluoromethyl-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(3-chloro-phenyl)-urea;
1-(4-tert-Butyl-phenyl)-3-{4-chloro-3-[2-(2-dimethylamino-ethylamino) -8-methoxy-7-oxo-7,8-dihydro-pyrido[2,3-d]pyrimidin-6-yl]-phenyl}-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-phenoxy-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-chloro-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(4-methyl-3-trifluoromethyl-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(2-fluoro-3-trifluoromethyl-phenyl)-urea;
1-{4-Chloro-3-[2-(2-dimethylamino-ethylamino)-8-methoxy-7-oxo-7,8-dihydro-pyrido [2,3-d]pyrimidin-6-yl]-phenyl}-3-(2-fluoro-5-trifluoromethyl-phenyl)-urea;
1-(3,5-Bis-trifluoromethyl-phenyl)-3-{4-chloro-3-[2-(2-dimethylamino-ethylamino) -8-methoxy-7-oxo-7,8-dihydro-pyrido[2,3-d]pyrimidin-6-yl]-phenyl}-urea;
4-Chloro-N-{3-chloro-4-[2-(2-dimethylamino-ethylamino)-8-methoxy-7-oxo-7,8-dihydro-pyrido[2,3-d]pyrimidin-6-yl]-phenyl}-3-trifluoromethyl-benzamide;
N-{3-Chloro-4-[2-(2-dimethylamino-ethylamino)-8-methoxy-7-oxo-7,8-dihydro-pyrido [2,3-d]pyrimidin-6-yl]-phenyl}-2-methoxy-4-trifluoromethyl-benzamide;
4-Chloro-N-{3-chloro-4-[2-(2-dimethylamino-ethylamino)-8-methoxy-7-oxo-7,8-dihydro-pyrido[2,3-d]pyrimidin-6-yl]]-phenyl}-3-trifluoromethoxy-benzamide;
N-{3-Chloro-4-[2-(2-dimethylamino-ethylamino)-8-methoxy-7-oxo-7,8-dihydro-pyrido [2,3-d]pyrimidin-6-yl]-phenyl}-4-(4-methyl-piperazin-1-ylmethyl)-benzamide;
N-{3-Chloro-4-[2-(2-dimethylamino-ethylamino)-8-methoxy-7-oxo-7,8-dihydro-pyrido [2,3-d]pyrimidin-6-yl]-phenyl}-2-morpholin-4-yl-isonicotinamide;
3-Chloro-N-{3-chloro-4-[2-(2-dimethylamino-ethylamino)-8-methoxy-7-oxo-7,8-dihydro-pyrido[2,3-d]pyrimidin-6-yl]-phenyl}-4-(3-fluoro-benzyloxy)-benzamide;
5-tert-Butyl-2-phenyl-2H-pyrazole-3-carboxylic acid {3-chloro-4-[2-(2-dimethylamino-ethylamino)-8-methoxy-7-oxo-7,8-dihydro-pyrido[2,3-d]pyrimidin-6-yl]-phenyl}-amide;
N-{3-Chloro-4-[2-(2-dimethylamino-ethylamino)-8-methoxy-7-oxo-7,8-dihydro-pyrido [2,3-d]pyrimidin-6-yl]-phenyl}-2-(4-chloro-3-trifluoromethyl-phenyl)-acetamide;
2,6-Dichloro-N-(4-chloro-3-(2-(2-(dimethylamino)ethylamino)-8-methoxy-7-oxo-7,8-dihydropyrido[2,3-d]pyrimidin-6-yl]-phenyl]-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)phenyl)-6-pyrrolidin-1-yl-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-dimethylamino-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-pyperidin-1-yl-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-morpholin-4-yl-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-(4-methyl-piperazin-1-yl)-isonicotinamide;
2-Chloro-N-(4-chloro-3-(2-(2-(dimethylamino)ethylamino)-8-methoxy-7-oxo-7,8-dihydropyrido[2,3-(i]pyrimidin-6-yl)-phenyl)-6-diethylamino-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-ethylamino-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-isopropylamino-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-(2-dimethylaminoethylamino)-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-1-methyl-piperdine-4-ylamino)-isonicotinamide;
2-Chloro-N-(4-chloro-3-(2-(2-(dimethylamino)ethylamino)-8-methoxy-7-oxo-7,8-dihydropyrido[2,3-d]pyrimidin-6-yl)-phenyl)-6-(4-(4-methylpiperazin-1-yl)-benzylamino)-isonicotinamide;
N-(4-chloro-3-(8-methoxy-2-(2-methoxy-ethylamino)-7-oxo-7,8-dihydropyrido[2,3-d]pyrimidin-6-yl)-phenyl)-benzamide;
N-(4-chloro-3-(2-ethylamino-8-methoxy-7-oxo-7,8-dihydropyrido[2,3-d]pyrimidin-6- yl)phenyl)-3-trifluormethyl-benzamide;
N-(3-(2-amino-8-methoxy-7-oxo-7,8-dihydropyrido[2,3-d]pyrimidin-6-yl)-4-chloro-phenyl)-3-trifluormethyl-benzamide;
N-(4-chloro-3-(8-methoxy-7-oxo-7,8-dihydropyrido[2,3-d ]pyrimidin-6-yl)-phenyl) -3-trifluormethyl-benzamide; and
N-{4-Chloro-3-[2-(3-dimethylamino-propylamino)-8-methoxy-7-oxo-7,8-dihydro-pyrido[2,3-d]pyrimidin-6-yl]-phenyl}-3-trifluoromethyl-benzamide.

9. A method for inhibiting cellular proliferation of colon cancer cell lines or colon tumor growth in an individual, said method comprising administering a therapeutically effective amount of the compound of claim 1.

10. The method of claim 9, wherein said individual is a mammal selected from: domestic mammal, cat, dog, horse, sheep, cow, rodent, and human.

11. The method of claim 10, wherein said mammal is a human.

* * * * *